United States Patent
Weber et al.

(10) Patent No.: US 11,597,937 B2
(45) Date of Patent: Mar. 7, 2023

(54) SYSTEM AND METHOD OF MODULAR CLONING

(71) Applicant: Icon Genetics GmbH, Halle (DE)

(72) Inventors: Ernst Weber, Halle/Saale (DE); Stefan Werner, Halle/Saale (DE); Carola Engler, Halle/Saale (DE); Ramona Grutzner, Halle/Saale (DE); Sylvestre Marillonnet, Halle/Saale (DE)

(73) Assignee: Icon Genetics GmbH, Halle (DE)

( * ) Notice: Subject to any disclaimer, the term of this patent is extended or adjusted under 35 U.S.C. 154(b) by 244 days.

(21) Appl. No.: 15/634,803

(22) Filed: Jun. 27, 2017

(65) Prior Publication Data
US 2017/0369889 A1 Dec. 28, 2017

Related U.S. Application Data

(62) Division of application No. 13/703,123, filed as application No. PCT/EP2011/002843 on Jun. 9, 2011, now abandoned.

(30) Foreign Application Priority Data

Jun. 11, 2010 (EP) .................................... 10006090
Jul. 6, 2010 (EP) .................................... 10006955

(51) Int. Cl.
*C40B 50/06* (2006.01)
*C12N 15/66* (2006.01)
(Continued)

(52) U.S. Cl.
CPC ......... *C12N 15/66* (2013.01); *C12N 15/1093* (2013.01); *C40B 40/10* (2013.01)

(58) Field of Classification Search
None
See application file for complete search history.

(56) References Cited

U.S. PATENT DOCUMENTS

2002/0025561 A1  2/2002 Hodgson
2010/0291633 A1  11/2010 Selmer et al.

FOREIGN PATENT DOCUMENTS

WO    03025169 A2    3/2003

OTHER PUBLICATIONS

Engler, C., et al., "A One Pot, One Step, Precision Cloning Method with High Thoughput Capabilty.," PLos One, 2008, vol. 3 (11), p. e3647.

(Continued)

*Primary Examiner* — Christian C Boesen
(74) *Attorney, Agent, or Firm* — Williams Mullen; David M. Saravitz

(57) ABSTRACT

System for producing a nucleic acid construct of interest, said system comprising:
  a set of n entry DNAs numbered 1 to n, n being an integer of at least 2,
  each of said n entry DNAs comprising in this order:
  (i) a type IIs restriction endonuclease recognition site followed by the cleavage site thereof;
  (ii) a sequence portion linking the cleavage site of said recognition site of item (i) with the cleavage site of the recognition site of the following item (iii), and
  (iii) a cleavage site of a further type IIs restriction endonuclease recognition site followed by the recognition site of said cleavage site;

(Continued)

the cleavage sites of the type IIs restriction endonuclease recognition sites of item (iii) of entry DNAs 1 to n−1 are complementary to the cleavage sites of the type IIs restriction endonuclease recognition sites of item (i) of entry DNAs 2 to n, respectively;

the cleavage site of the type IIs restriction endonuclease recognition site of item (iii) of entry DNA n is complementary to the cleavage site of the type IIs restriction endonuclease recognition site of item (i) of entry DNA 1 for allowing annealing of complementary single-stranded overhangs formed by restriction at recognition site (i) of entry DNA 1 and at recognition site (iii) of entry DNA n;

said system further comprising a destination vector comprising in this order:

(I) a type IIs restriction endonuclease recognition site followed by the cleavage site thereof;

(II) a vector backbone preferably comprising a selectable marker gene, said vector backbone linking the cleavage sites of said recognition sites of items (I) and the following item (III);

(III) a further cleavage site of a type IIs restriction endonuclease recognition site followed by the recognition site of said cleavage site, and (IV) optionally, an insert between the recognition sites of item (III) and item (I);

said cleavage sites of items (I) and (III) being different and non-complementary, said recognition sites of items (I) and (III) being preferably recognitions sites of the same endonuclease.

12 Claims, 47 Drawing Sheets

Specification includes a Sequence Listing.

(51) Int. Cl.
*C12N 15/10* (2006.01)
*C40B 40/10* (2006.01)

(56) References Cited

OTHER PUBLICATIONS

Engler, C., et al., Golder Gate Shuffling: A One-Pot DNA Shuffling Method Based on Type IIs Restriction Enzymes, PLoS ONE, 2008, vol. 4(5), p. e5553.

Peisajovich, S., et al., "BioBricks Foundation Request for Comments—BBF RFC 28: A method for combinatorial multi-part assembly based on the Type IIs restriction enzyme AarI," 2009, 5 pages.

Rebatchouk, D., et al., "NOMAD: A versatile strategy for in vitro DNA manipulation applied to promoter analysis and vector design," Proc. Natl. Acad. Sci. USA, vol. 93(20), pp. 10891-10896.

Written Opinion of the International Searching Authority for PCT/EP2011/002843, dated Nov. 15, 2011.

International Search Report for PCT/EP2011/002843, dated Nov. 15, 2011.

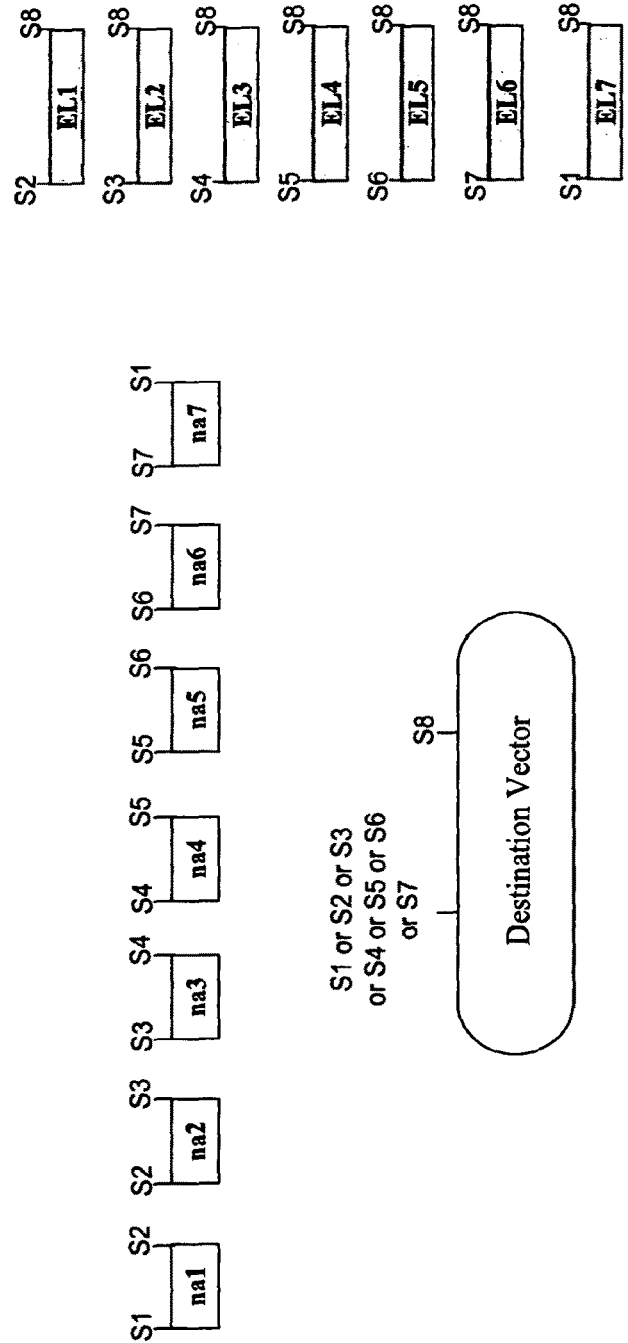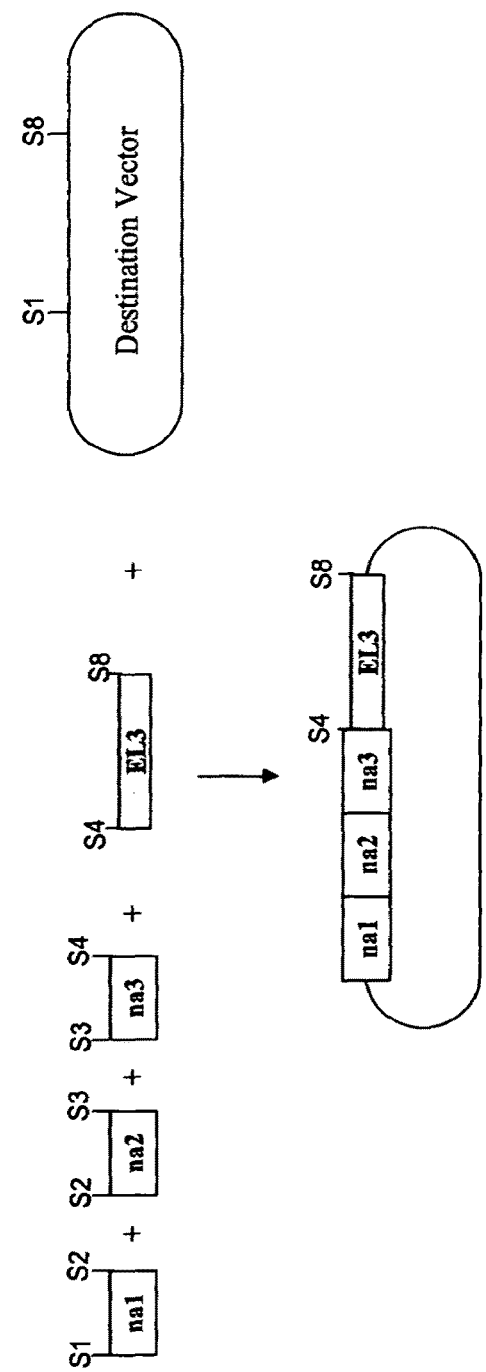
Fig. 1A
Fig. 1B

Fig. 10

| Group | Plasmid | Expected color-other | Miniprep correct | Plasmid size (kb) |
|---|---|---|---|---|
| level 2-2 blue to white | pICH51811* | 2685-0 | 6/6 | 33.4 |
| | pICH51811 | 159-3 | 0/6 | 33.4 |
| | pICH51802 | 893-20 | 4/6 | 31.5 |
| | pICH51792 | 693-6 | 4/6 | 29.4 |
| | pICH51781 | 13440-5 | 6/6 | 26.8 |
| | pICH51771 | 45000-0 | 6/6 | 25.5 |
| | pICH51761 | 45000-7 | 6/6 | 23.7 |
| level 2i-1 red to blue | pICH51226 | 75-25 | 2/6 | 24.3 |
| | pICH51212 | 330-45/60/10 | 6/6 | 20.4 |
| level 2-1 red to white | pICH51201 | 150-15 | 6/6 | 23.7 |
| | pICH51191 | 965-100 | 6/6 | 19.9 |
| | pICH51181 | 3910-95 | 6/6 | 17.0 |
| | pICH51171 | 10650-30 | 6/6 | 14.2 |
| | pICH51161 | 32640-5 | 6/6 | 10.0 |
| level 1 blue to white | pICH50711 | 38933-0 | 2/2 | 7.2 |
| | pICH50721 | 103466-0 | 2/2 | 6.6 |
| | pICH49722 | 32800-0 | 2/2 | 8.5 |
| | pICH49733 | 28933-0 | 2/2 | 7.1 |
| | pICH50731 | 65733-0 | 2/2 | 7.2 |
| | pICH50741 | 16400-0 | 2/2 | 8.2 |
| | pICH50751 | 184000-0 | 2/2 | 6.1 |
| | pICH50761 | 26933-200 | 2/2 | 5.7 |
| | pICH50771 | 85600-0 | 2/2 | 6.9 |
| | pICH50781 | 140000-166 | 2/2 | 6.4 |
| | pICH50791 | 81066-0 | 2/2 | 6.3 |

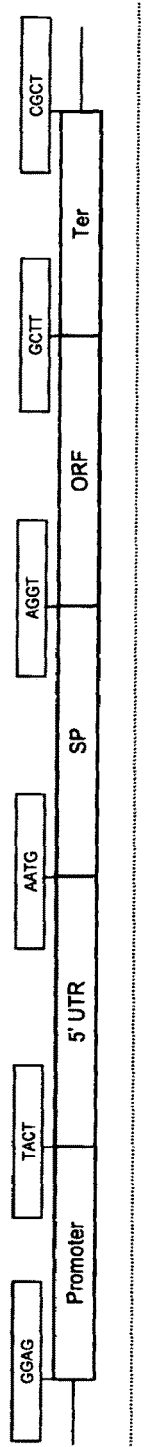
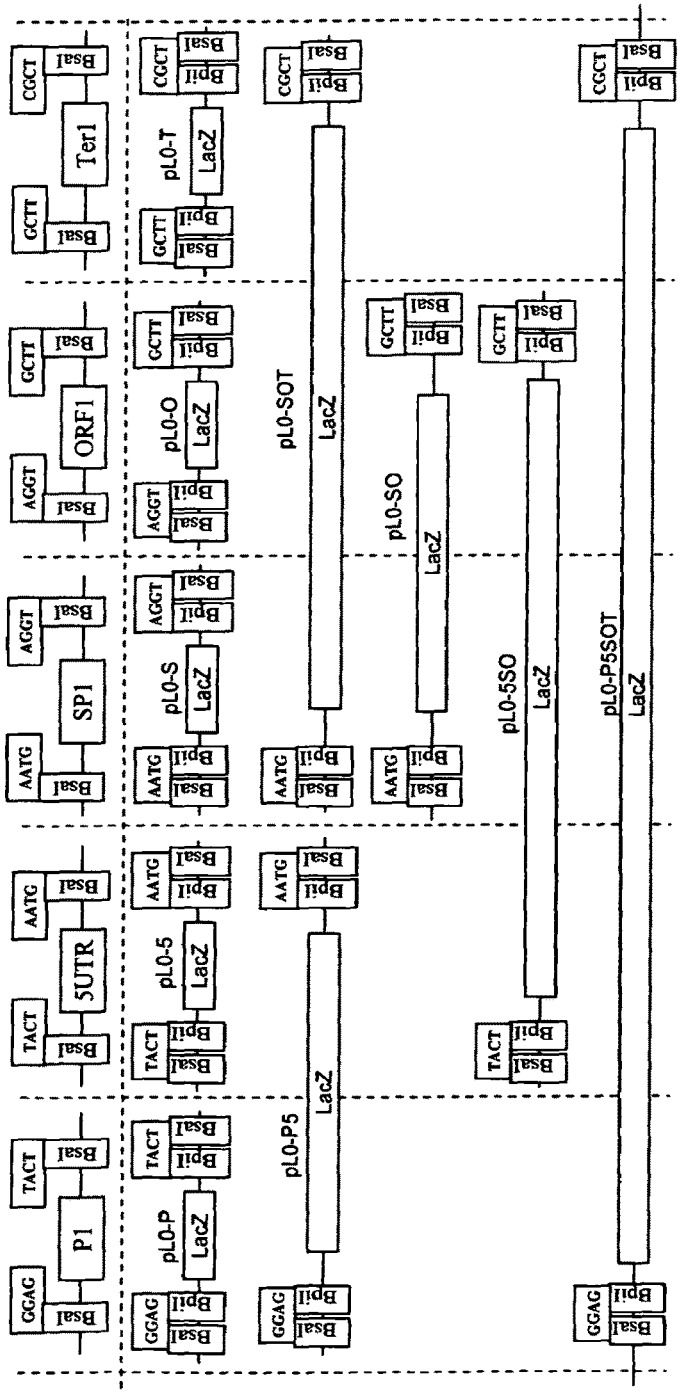
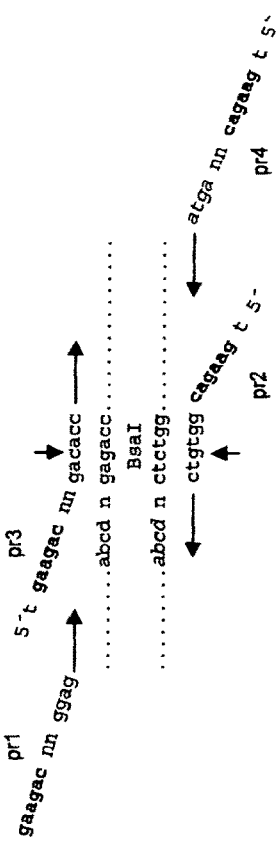
Fig. 18A
Fig. 18B
Fig. 18C

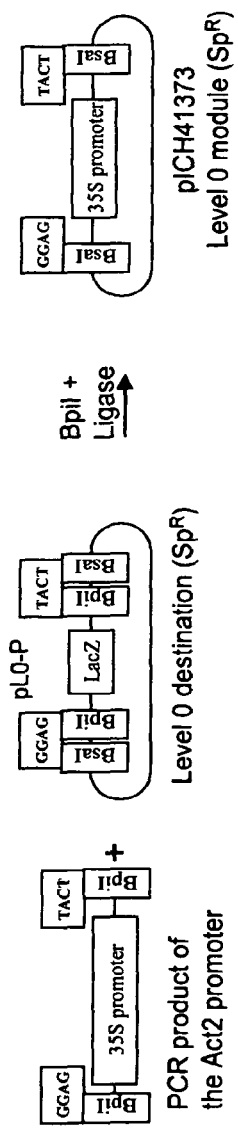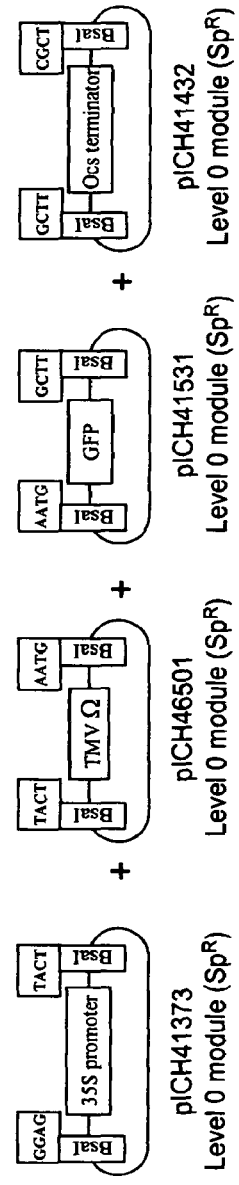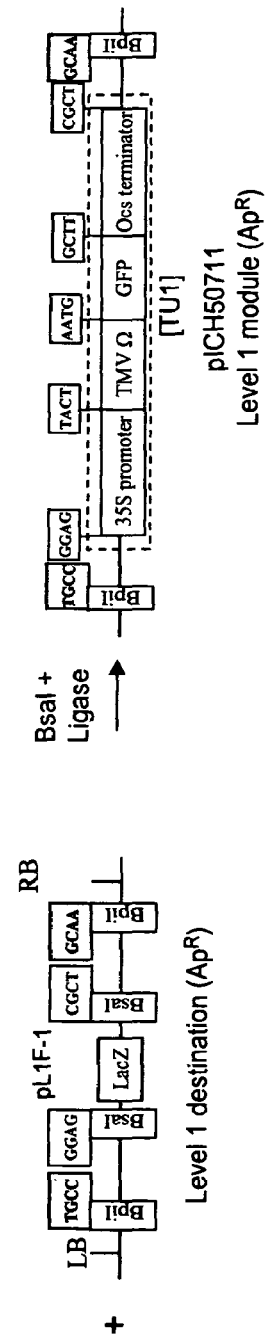
Fig. 19A
Fig. 19B

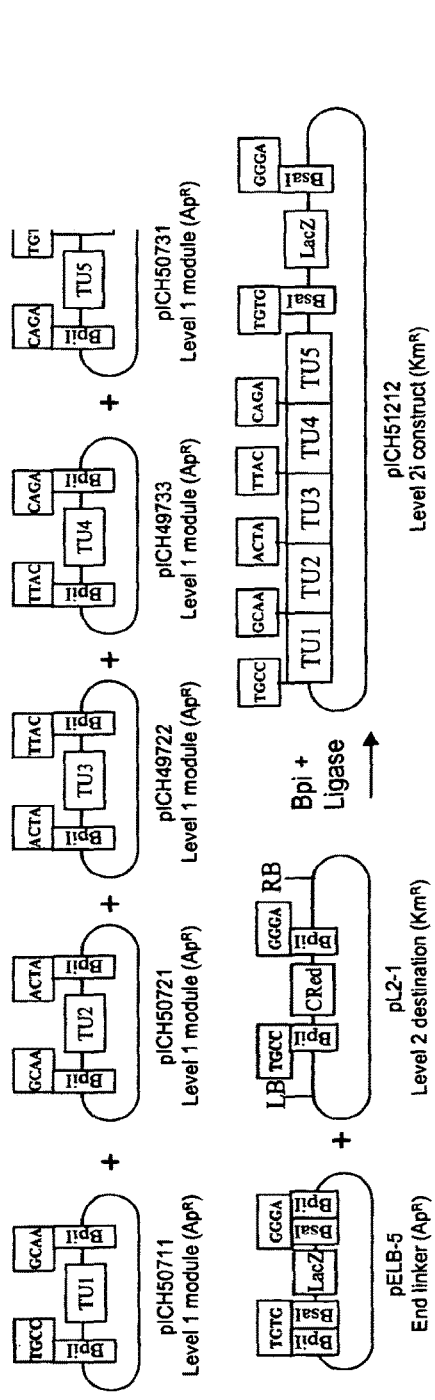
Fig. 19C  Cloning of the level 2i construct pICH51212
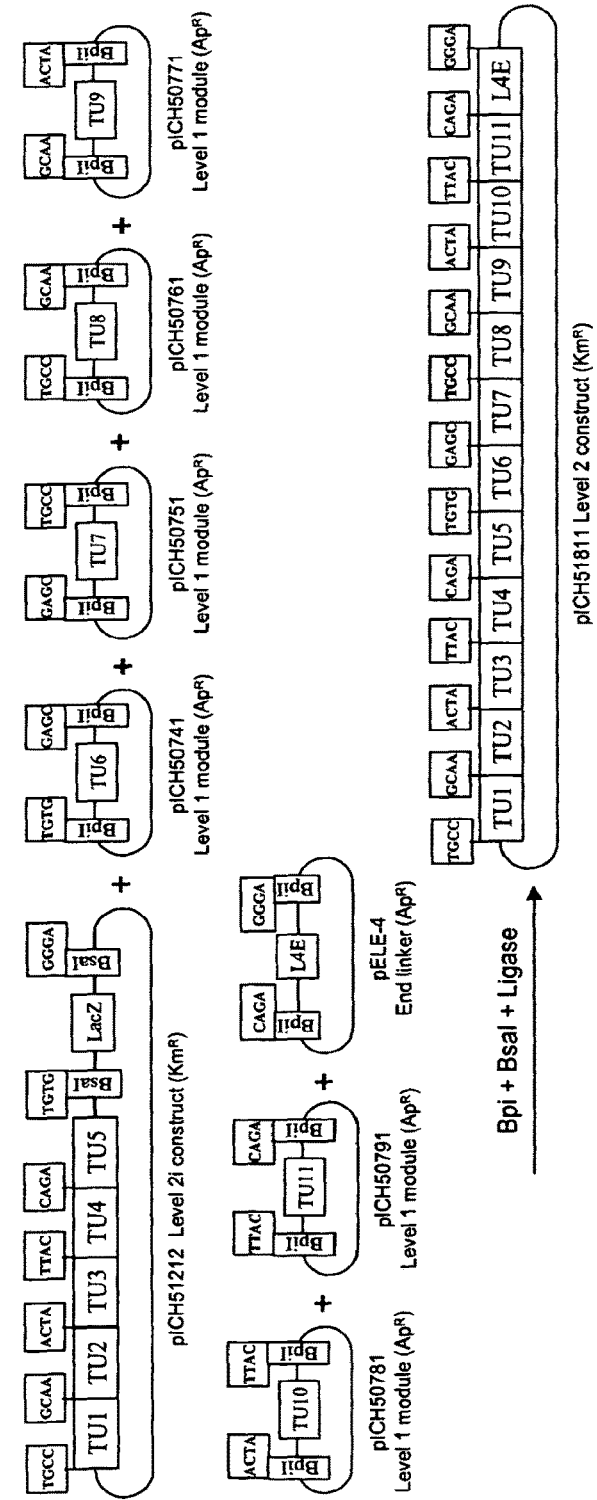
Fig. 19D  Cloning of the level 2-2 construct pICH51811

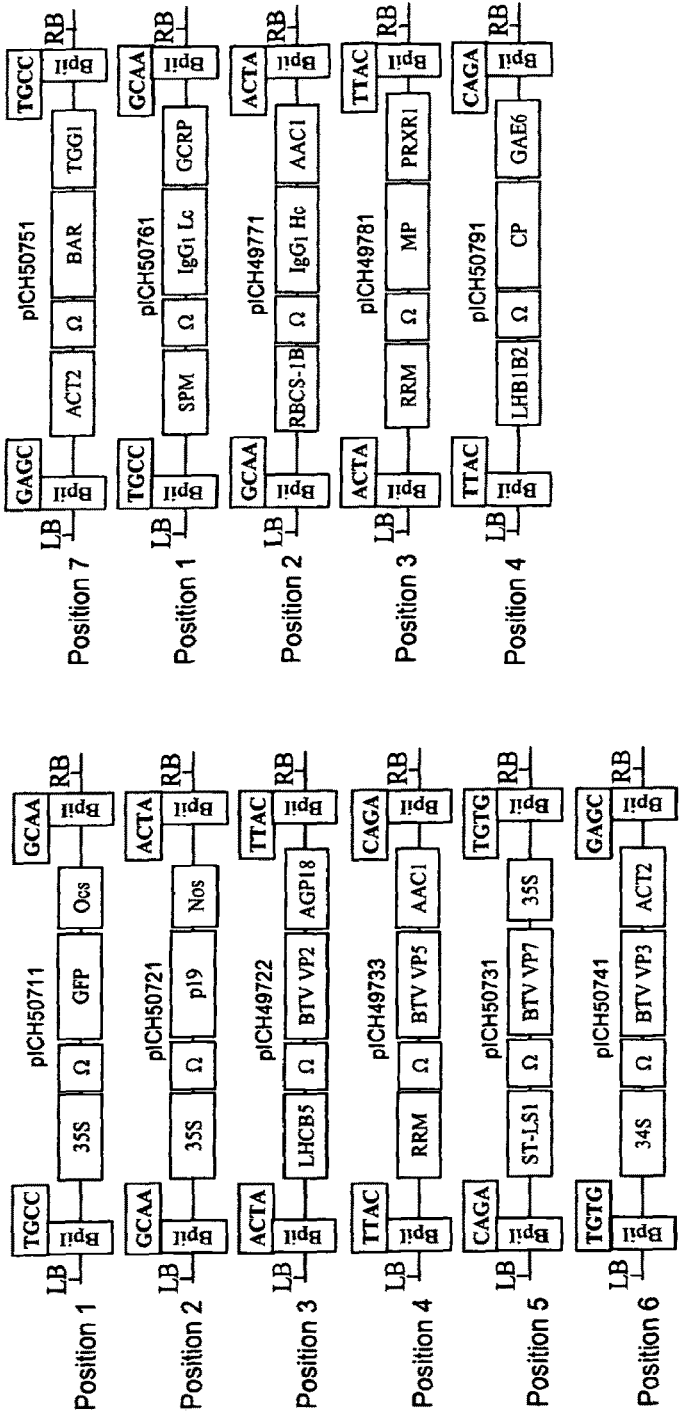
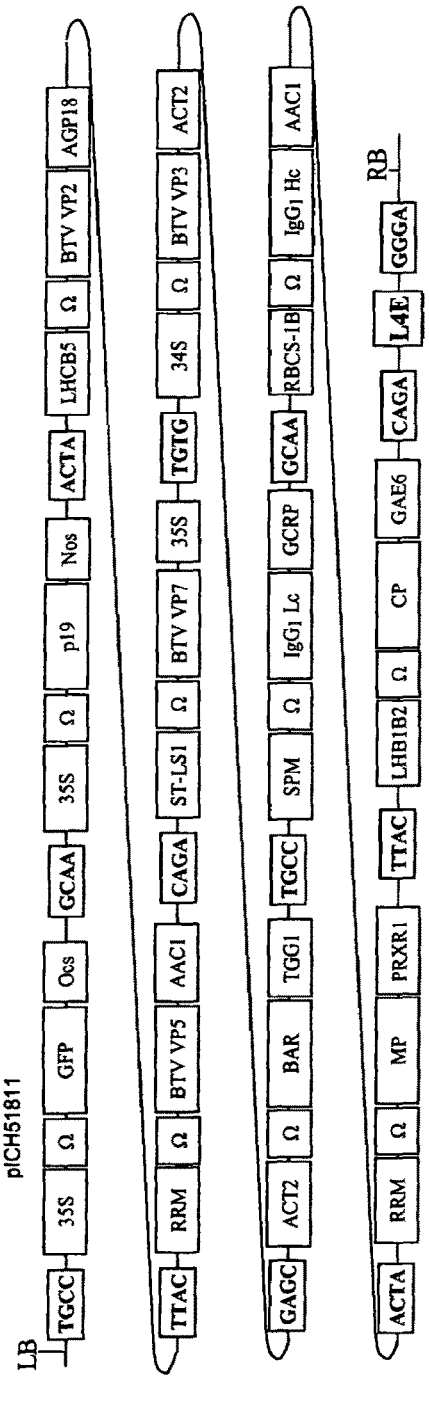
Fig 20A
Fig. 20B

Fig. 22
Level 0: Prokaryotic ORFs
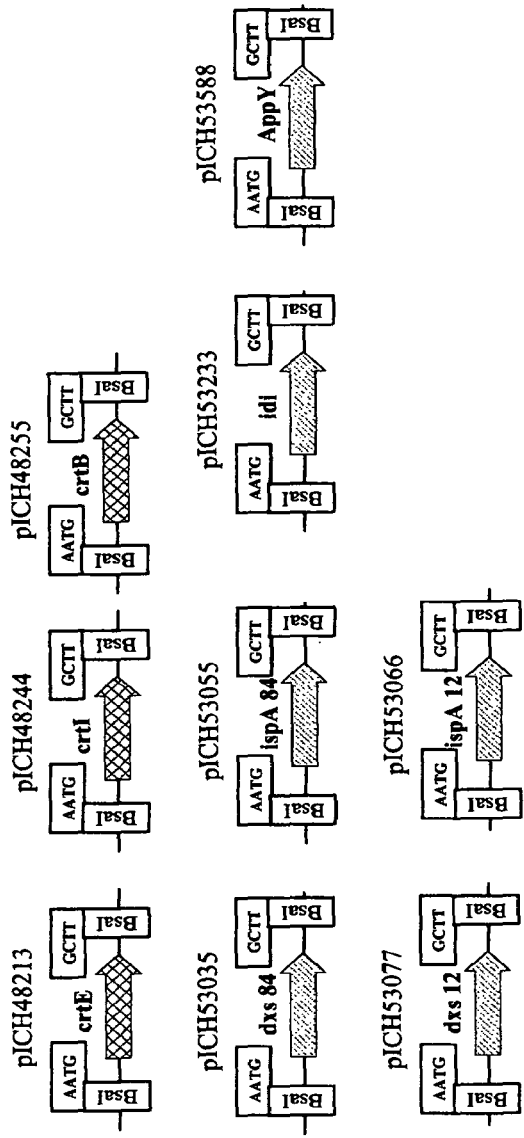
Level 0: Prokaryotic promoters
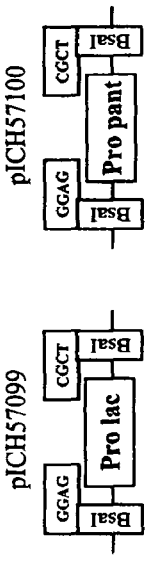

Fig. 26 A
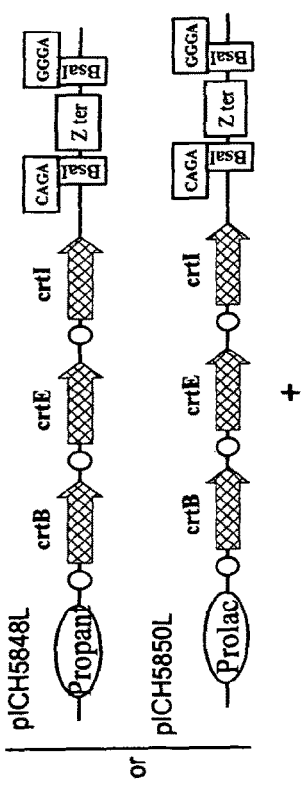
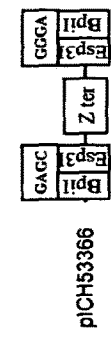
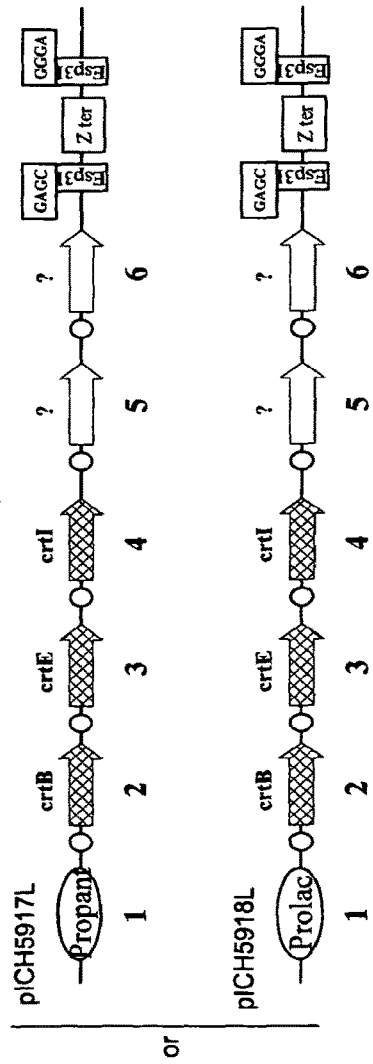

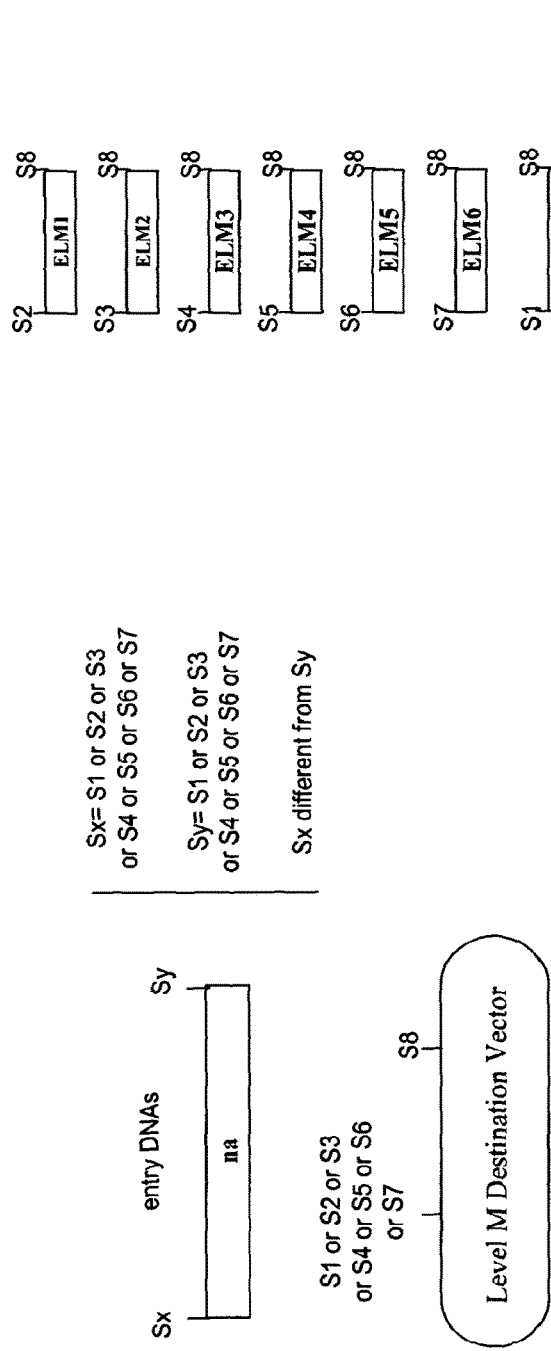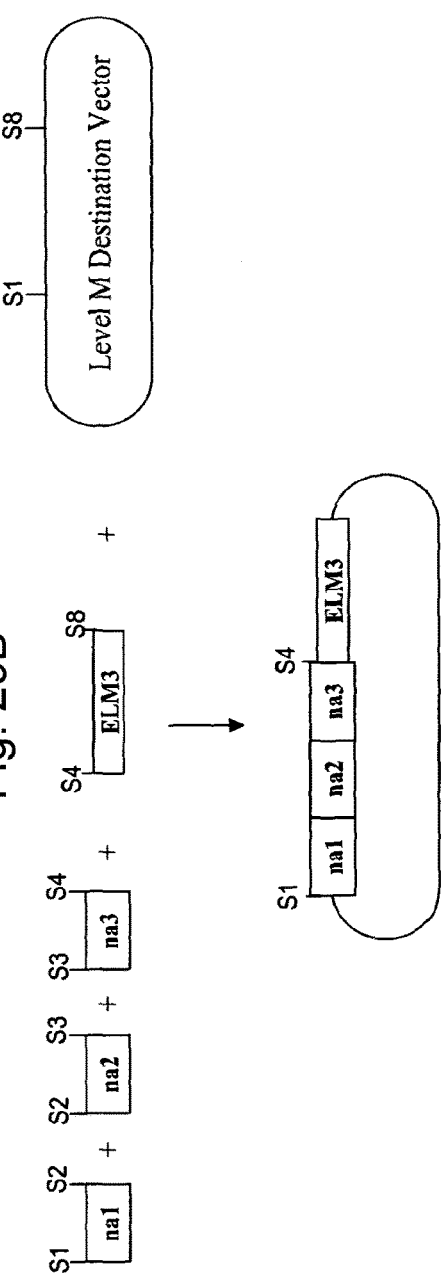

SEQUENCE LISTING

<160> NUMBER OF SEQ ID NOS: 56

<210> SEQ ID NO 1
<211> LENGTH: 20
<212> TYPE: DNA
<213> ORGANISM: Artificial Sequence
<220> FEATURE:
<223> OTHER INFORMATION: PCR primer

<400> SEQUENCE: 1
agcgaggaag cggaagagcg                                          20

<210> SEQ ID NO 2
<211> LENGTH: 22

<212> TYPE: DNA
<213> ORGANISM: Artificial Sequence
<220> FEATURE:
<223> OTHER INFORMATION: PCR primer

<400> SEQUENCE: 2
gccacctgac gtctaagaaa cc                                              22

<210> SEQ ID NO 3
<211> LENGTH: 34
<212> TYPE: DNA
<213> ORGANISM: Artificial Sequence
<220> FEATURE:
<223> OTHER INFORMATION: PCR primer

<400> SEQUENCE: 3
tttggtctca ggagggtacc gcacggtctg ccaa                                 34

<210> SEQ ID NO 4
<211> LENGTH: 37
<212> TYPE: DNA
<213> ORGANISM: Artificial Sequence
<220> FEATURE:
<223> OTHER INFORMATION: PCR primer

<400> SEQUENCE: 4
tttggtctca tcatgcagca tccttaactg acggcag                              37

<210> SEQ ID NO 5
<211> LENGTH: 30
<212> TYPE: DNA
<213> ORGANISM: Artificial Sequence
<220> FEATURE:
<223> OTHER INFORMATION: PCR primer

<400> SEQUENCE: 5
tttggtctca atgagcgcac atgccctgcc                                      30

<210> SEQ ID NO 6
<211> LENGTH: 35
<212> TYPE: DNA
<213> ORGANISM: Artificial Sequence
<220> FEATURE:
<223> OTHER INFORMATION: PCR primer

<400> SEQUENCE: 6
tttggtctca tcactcatgc ggtgtccccc ttggt                                35

<210> SEQ ID NO 7
<211> LENGTH: 34
<212> TYPE: DNA
<213> ORGANISM: Artificial Sequence
<220> FEATURE:
<223> OTHER INFORMATION: PCR primer

<400> SEQUENCE: 7
tttggtctca gtgacttaag tgggagcggc tatg                                 34

<210> SEQ ID NO 8
<211> LENGTH: 34
<212> TYPE: DNA
<213> ORGANISM: Artificial Sequence
<220> FEATURE:
<223> OTHER INFORMATION: PCR primer

<400> SEQUENCE: 8
tttggtctca atgtagtcgc tctttaacga tgag           34

<210> SEQ ID NO 9
<211> LENGTH: 15
<212> TYPE: DNA
<213> ORGANISM: Artificial Sequence
<220> FEATURE:
<223> OTHER INFORMATION: part of forward primer

<400> SEQUENCE: 9
tttgaagaca aggag                                15

<210> SEQ ID NO 10
<211> LENGTH: 15
<212> TYPE: DNA
<213> ORGANISM: Artificial Sequence
<220> FEATURE:
<223> OTHER INFORMATION: part of reverse primer

<400> SEQUENCE: 10
tttgaagaca aagta                                15

<210> SEQ ID NO 11
<211> LENGTH: 44
<212> TYPE: DNA
<213> ORGANISM: Artificial Sequence
<220> FEATURE:
<223> OTHER INFORMATION: liner pELE-1

<400> SEQUENCE: 11
gaagacaagc aagaggatgc acatgtgacc gagggattgt cttc           44

<210> SEQ ID NO 12
<211> LENGTH: 19
<212> TYPE: DNA
<213> ORGANISM: Artificial Sequence
<220> FEATURE:
<223> OTHER INFORMATION: pELB-1

<400> SEQUENCE: 12
gaagacaatg cctgagacc                            19

<210> SEQ ID NO 13
<211> LENGTH: 578
<212> TYPE: DNA
<213> ORGANISM: Artificial Sequence
<220> FEATURE:
<223> OTHER INFORMATION: LacZ alpha fragment

<400> SEQUENCE: 13
gcagctggca cgacaggttt cccgactgga aagcgggcag tgagcgcaac gcaattaatg     60
tgagttagct cactcattag gcaccccagg ctttacactt tatgcttccg gctcgtatgt    120
tgtgtggaat tgtgagcgga taacaatttc acacaggaaa cagctatgac catgattacg    180
ccaagcttgc atgcctgcag gtcgactcta gaggatcccc gggtaccgag ctcgaattca    240
ctggccgtcg ttttacaacg tcgtgactgg gaaaaccctg gcgttaccca acttaatcgc    300
cttgcagcac atccccccttt cgccagctgg cgtaatagcg aagaggcccg caccgatcgc    360
ccttcccaac agttgcgcag cctgaatggc gaatggcgcc tgatgcggta ttttctcctt    420
acgcatctgt gcggtatttc acaccgcata tggtgcactc tcagtacaat ctgctctgat    480
gccgcatagt taagccagcc ccgacacccg ccaacacccg ctgacgcgcc ctgacgggct    540
tgtctgctcc cggcatccgc ttacagacaa gctgtgac                           578

```
<210> SEQ ID NO 14
<211> LENGTH: 20
<212> TYPE: DNA
<213> ORGANISM: Artificial Sequence
<220> FEATURE:
<223> OTHER INFORMATION: part of pELB-1

<400> SEQUENCE: 14
ggtctcaggg attgtcttca                                                 20

<210> SEQ ID NO 15
<211> LENGTH: 73
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: (27)..(27)
<223> OTHER INFORMATION: any base
<220> FEATURE:
<221> NAME/KEY: misc_feature
<222> LOCATION: (28)..(28)
<223> OTHER INFORMATION: a,c or g
<220> FEATURE:
<221> NAME/KEY: misc_feature
<222> LOCATION: (33)..(33)
<223> OTHER INFORMATION: a, t or g
<220> FEATURE:
<221> NAME/KEY: misc_feature
<222> LOCATION: (34)..(39)
<223> OTHER INFORMATION: any base

<400> SEQUENCE: 15
tttcgtctca ttcagaagac attgccnvag gadnnnnnna atgggagacc ttatgaccat      60
gattacgcca agc                                                        73

<210> SEQ ID NO 16
<211> LENGTH: 61
<212> TYPE: DNA
<213> ORGANISM: Artificial Sequence
<220> FEATURE:
<223> OTHER INFORMATION: PCR primer

<400> SEQUENCE: 16
tttcgtctca cttagaagac aattgcaagc tgagacctta tgcggcatca gagcagattg      60
t                                                                     61

<210> SEQ ID NO 17
<211> LENGTH: 11
<212> TYPE: DNA
<213> ORGANISM: Artificial Sequence
<220> FEATURE:
<223> OTHER INFORMATION: recognition and cleavage site
<220> FEATURE:
<221> NAME/KEY: misc_feature
<222> LOCATION: (7)..(7)
<223> OTHER INFORMATION: n is a, c, g, or t

<400> SEQUENCE: 17
ggtctcnggt a                                                          11

<210> SEQ ID NO 18
<211> LENGTH: 11
<212> TYPE: DNA
<213> ORGANISM: Artificial Sequence
<220> FEATURE:
```

```
<223> OTHER INFORMATION: recognition and cleavage site
<220> FEATURE:
<221> NAME/KEY: misc_feature
<222> LOCATION: (5)..(5)
<223> OTHER INFORMATION: n is a, c, g, or t

<400> SEQUENCE: 18
aggtngagac c                                                          11

<210> SEQ ID NO 19
<211> LENGTH: 12
<212> TYPE: DNA
<213> ORGANISM: Artificial Sequence
<220> FEATURE:
<223> OTHER INFORMATION: recognition and cleavage site
<220> FEATURE:
<221> NAME/KEY: misc_feature
<222> LOCATION: (7)..(8)
<223> OTHER INFORMATION: n is a, c, g, or t

<400> SEQUENCE: 19
gaagacnntt ac                                                         12

<210> SEQ ID NO 20
<211> LENGTH: 12
<212> TYPE: DNA
<213> ORGANISM: Artificial Sequence
<220> FEATURE:
<223> OTHER INFORMATION: recognition and cleavage site
<220> FEATURE:
<221> NAME/KEY: misc_feature
<222> LOCATION: (5)..(6)
<223> OTHER INFORMATION: n is a, c, g, or t

<400> SEQUENCE: 20
tgccnngtct tc                                                         12

<210> SEQ ID NO 21
<211> LENGTH: 12
<212> TYPE: DNA
<213> ORGANISM: Artificial Sequence
<220> FEATURE:
<223> OTHER INFORMATION: recognition and cleavage site
<220> FEATURE:
<221> NAME/KEY: misc_feature
<222> LOCATION: (7)..(8)
<223> OTHER INFORMATION: n is a, c, g, or t

<400> SEQUENCE: 21
gaagacnnac ta                                                         12

<210> SEQ ID NO 22
<211> LENGTH: 11
<212> TYPE: DNA
<213> ORGANISM: Artificial Sequence
<220> FEATURE:
<223> OTHER INFORMATION: recognition and cleavage site
<220> FEATURE:
<221> NAME/KEY: misc_feature
<222> LOCATION: (5)..(5)
<223> OTHER INFORMATION: n is a, c, g, or t

<400> SEQUENCE: 22
ggagngagac c                                                          11

<210> SEQ ID NO 23
<211> LENGTH: 11
<212> TYPE: DNA
<213> ORGANISM: Artificial Sequence
```

```
<220> FEATURE:
<223> OTHER INFORMATION: recognition and cleavage site
<220> FEATURE:
<221> NAME/KEY: misc_feature
<222> LOCATION: (7)..(7)
<223> OTHER INFORMATION: n is a, c, g, or t

<400> SEQUENCE: 23
ggtctcncgc t                                                              11

<210> SEQ ID NO 24
<211> LENGTH: 12
<212> TYPE: DNA
<213> ORGANISM: Artificial Sequence
<220> FEATURE:
<223> OTHER INFORMATION: recognition and cleavage site
<220> FEATURE:
<221> NAME/KEY: misc_feature
<222> LOCATION: (5)..(6)
<223> OTHER INFORMATION: n is a, c, g, or t

<400> SEQUENCE: 24
ttacnngtct tc                                                             12

<210> SEQ ID NO 25
<211> LENGTH: 19
<212> TYPE: DNA
<213> ORGANISM: Artificial Sequence
<220> FEATURE:
<223> OTHER INFORMATION: recognition and cleavage site
<220> FEATURE:
<221> NAME/KEY: misc_feature
<222> LOCATION: (7)..(8)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t

<400> SEQUENCE: 25
gaagacnngc aangagacc                                                      19

<210> SEQ ID NO 26
<211> LENGTH: 18
<212> TYPE: DNA
<213> ORGANISM: Artificial Sequence
<220> FEATURE:
<223> OTHER INFORMATION: recognition and cleavage site
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t

<400> SEQUENCE: 26
ggtctcnact angtcttc                                                       18

<210> SEQ ID NO 27
<211> LENGTH: 13
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: (8)..(9)
<223> OTHER INFORMATION: n is a, c, g, or t
```

```
<400> SEQUENCE: 27
tgaagacnng gag                                                          13

<210> SEQ ID NO 28
<211> LENGTH: 13
<212> TYPE: DNA
<213> ORGANISM: Artificial Sequence
<220> FEATURE:
<223> OTHER INFORMATION: PCR primer

<400> SEQUENCE: 28
tgaagacggt gtc                                                          13

<210> SEQ ID NO 29
<211> LENGTH: 15
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: (8)..(9)
<223> OTHER INFORMATION: n is a, c, g, or t

<400> SEQUENCE: 29
tgaagacnng acacc                                                        15

<210> SEQ ID NO 30
<211> LENGTH: 13
<212> TYPE: DNA
<213> ORGANISM: Artificial Sequence
<220> FEATURE:
<223> OTHER INFORMATION: PCR primer
<220> FEATURE:
<221> NAME/KEY: misc_feature
<222> LOCATION: (8)..(9)
<223> OTHER INFORMATION: n is a, c, g, or t

<400> SEQUENCE: 30
tgaagacnna gta                                                          13

<210> SEQ ID NO 31
<211> LENGTH: 12
<212> TYPE: DNA
<213> ORGANISM: Artificial Sequence
<220> FEATURE:
<223> OTHER INFORMATION: sequence stretch
<220> FEATURE:
<221> NAME/KEY: misc_feature
<222> LOCATION: (7)..(8)
<223> OTHER INFORMATION: n is a, c, g, or t

<400> SEQUENCE: 31
gaagacnngg ag                                                           12

<210> SEQ ID NO 32
<211> LENGTH: 12
<212> TYPE: DNA
<213> ORGANISM: Artificial Sequence
<220> FEATURE:
<223> OTHER INFORMATION: sequence stretch
<220> FEATURE:
<221> NAME/KEY: misc_feature
<222> LOCATION: (5)..(6)
<223> OTHER INFORMATION: n is a, c, g, or t

<400> SEQUENCE: 32
tactnngtct tc                                                           12
```

```
<210> SEQ ID NO 33
<211> LENGTH: 12
<212> TYPE: DNA
<213> ORGANISM: Artificial Sequence
<220> FEATURE:
<223> OTHER INFORMATION: sequence stretch
<220> FEATURE:
<221> NAME/KEY: misc_feature
<222> LOCATION: (5)..(6)
<223> OTHER INFORMATION: n is a, c, g, or t

<400> SEQUENCE: 33
ctccnngtct tc                                                              12

<210> SEQ ID NO 34
<211> LENGTH: 12
<212> TYPE: DNA
<213> ORGANISM: Artificial Sequence
<220> FEATURE:
<223> OTHER INFORMATION: sequence stretch
<220> FEATURE:
<221> NAME/KEY: misc_feature
<222> LOCATION: (7)..(8)
<223> OTHER INFORMATION: n is a, c, g, or t

<400> SEQUENCE: 34
gaagacnnag ta                                                              12

<210> SEQ ID NO 35
<211> LENGTH: 19
<212> TYPE: DNA
<213> ORGANISM: Artificial Sequence
<220> FEATURE:
<223> OTHER INFORMATION: sequence stretch
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (12)..(13)
<223> OTHER INFORMATION: n is a, c, g, or t

<400> SEQUENCE: 35
ggtctcngga gnngtcttc                                                       19

<210> SEQ ID NO 36
<211> LENGTH: 19
<212> TYPE: DNA
<213> ORGANISM: Artificial Sequence
<220> FEATURE:
<223> OTHER INFORMATION: sequence stretch
<220> FEATURE:
<221> NAME/KEY: misc_feature
<222> LOCATION: (7)..(8)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t

<400> SEQUENCE: 36
gaagtcnnta ctngagacc                                                       19

<210> SEQ ID NO 37
<211> LENGTH: 19
<212> TYPE: DNA
<213> ORGANISM: Artificial Sequence
<220> FEATURE:
```

<223> OTHER INFORMATION: sequence stretch
<220> FEATURE:
<221> NAME/KEY: misc_feature
<222> LOCATION: (7)..(8)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t

<400> SEQUENCE: 37
gaagacnnct ccngagacc                                              19

<210> SEQ ID NO 38
<211> LENGTH: 19
<212> TYPE: DNA
<213> ORGANISM: Artificial Sequence
<220> FEATURE:
<223> OTHER INFORMATION: sequence stretch
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (12)..(13)
<223> OTHER INFORMATION: n is a, c, g, or t

<400> SEQUENCE: 38
ggtctcnagt anngtcttc                                              19

<210> SEQ ID NO 39
<211> LENGTH: 11
<212> TYPE: DNA
<213> ORGANISM: Artificial Sequence
<220> FEATURE:
<223> OTHER INFORMATION: sequence stretch
<220> FEATURE:
<221> NAME/KEY: misc_feature
<222> LOCATION: (7)..(7)
<223> OTHER INFORMATION: n is a, c, g, or t

<400> SEQUENCE: 39
ggtctcngga g                                                      11

<210> SEQ ID NO 40
<211> LENGTH: 11
<212> TYPE: DNA
<213> ORGANISM: Artificial Sequence
<220> FEATURE:
<223> OTHER INFORMATION: sequence stretch
<220> FEATURE:
<221> NAME/KEY: misc_feature
<222> LOCATION: (5)..(5)
<223> OTHER INFORMATION: n is a, c, g, or t

<400> SEQUENCE: 40
tactngagac c                                                      11

<210> SEQ ID NO 41
<211> LENGTH: 11
<212> TYPE: DNA
<213> ORGANISM: Artificial Sequence
<220> FEATURE:
<223> OTHER INFORMATION: sequence stretch
<220> FEATURE:
<221> NAME/KEY: misc_feature
<222> LOCATION: (5)..(5)
<223> OTHER INFORMATION: n is a, c, g, or t

<400> SEQUENCE: 41
ctccngagac c                                                          11

<210> SEQ ID NO 42
<211> LENGTH: 11
<212> TYPE: DNA
<213> ORGANISM: Artificial Sequence
<220> FEATURE:
<223> OTHER INFORMATION: sequence stretch
<220> FEATURE:
<221> NAME/KEY: misc_feature
<222> LOCATION: (7)..(7)
<223> OTHER INFORMATION: n is a, c, g, or t

<400> SEQUENCE: 42
ggtctcnagt a                                                          11

<210> SEQ ID NO 43
<211> LENGTH: 12
<212> TYPE: DNA
<213> ORGANISM: Artificial Sequence
<220> FEATURE:
<223> OTHER INFORMATION: sequence stretch
<220> FEATURE:
<221> NAME/KEY: misc_feature
<222> LOCATION: (7)..(8)
<223> OTHER INFORMATION: n is a, c, g, or t

<400> SEQUENCE: 43
gaagacnntg cc                                                         12

<210> SEQ ID NO 44
<211> LENGTH: 11
<212> TYPE: DNA
<213> ORGANISM: Artificial Sequence
<220> FEATURE:
<223> OTHER INFORMATION: sequence stretch
<220> FEATURE:
<221> NAME/KEY: misc_feature
<222> LOCATION: (5)..(5)
<223> OTHER INFORMATION: n is a, c, g, or t

<400> SEQUENCE: 44
ggagngagac c                                                          11

<210> SEQ ID NO 45
<211> LENGTH: 23
<212> TYPE: DNA
<213> ORGANISM: Artificial Sequence
<220> FEATURE:
<223> OTHER INFORMATION: sequence stretch
<220> FEATURE:
<221> NAME/KEY: misc_feature
<222> LOCATION: (7)..(7)
<223> OTHER INFORMATION: n is a, c, g, or t
<220> FEATURE:
<221> NAME/KEY: misc_feature
<222> LOCATION: (16)..(17)
<223> OTHER INFORMATION: n is a, c, g, or t

<400> SEQUENCE: 45
ggtctcncgc tgcaanngtc ttc                                             23

<210> SEQ ID NO 46
<211> LENGTH: 12
<212> TYPE: DNA
<213> ORGANISM: Artificial Sequence
<220> FEATURE:
<223> OTHER INFORMATION: sequence stretch
<220> FEATURE:

```
<221> NAME/KEY: misc_feature
<222> LOCATION: (5)..(6)
<223> OTHER INFORMATION: n is a, c, g, or t

<400> SEQUENCE: 46
ggcanngtct tc                                                           12

<210> SEQ ID NO 47
<211> LENGTH: 11
<212> TYPE: DNA
<213> ORGANISM: Artificial Sequence
<220> FEATURE:
<223> OTHER INFORMATION: sequence stretch
<220> FEATURE:
<221> NAME/KEY: misc_feature
<222> LOCATION: (7)..(7)
<223> OTHER INFORMATION: n is a, c, g, or t

<400> SEQUENCE: 47
ggtctcnctc c                                                            11

<210> SEQ ID NO 48
<211> LENGTH: 23
<212> TYPE: DNA
<213> ORGANISM: Artificial Sequence
<220> FEATURE:
<223> OTHER INFORMATION: sequence stretch
<220> FEATURE:
<221> NAME/KEY: misc_feature
<222> LOCATION: (7)..(8)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t

<400> SEQUENCE: 48
gaagacnntt gcagcgngag acc                                               23

<210> SEQ ID NO 49
<211> LENGTH: 12
<212> TYPE: DNA
<213> ORGANISM: Artificial Sequence
<220> FEATURE:
<223> OTHER INFORMATION: sequence stretch
<220> FEATURE:
<221> NAME/KEY: misc_feature
<222> LOCATION: (7)..(8)
<223> OTHER INFORMATION: n is a, c, g, or t

<400> SEQUENCE: 49
gaagacnntg cc                                                           12

<210> SEQ ID NO 50
<211> LENGTH: 16
<212> TYPE: DNA
<213> ORGANISM: Artificial Sequence
<220> FEATURE:
<223> OTHER INFORMATION: sequence stretch
<220> FEATURE:
<221> NAME/KEY: misc_feature
<222> LOCATION: (9)..(10)
<223> OTHER INFORMATION: n is a, c, g, or t

<400> SEQUENCE: 50
cgctgcaann gtcttc                                                       16

<210> SEQ ID NO 51
<211> LENGTH: 12
```

```
<212> TYPE: DNA
<213> ORGANISM: Artificial Sequence
<220> FEATURE:
<223> OTHER INFORMATION: sequence stretch
<220> FEATURE:
<221> NAME/KEY: misc_feature
<222> LOCATION: (5)..(6)
<223> OTHER INFORMATION: n is a, c, g, or t

<400> SEQUENCE: 51
ggcanngtct tc                                                            12

<210> SEQ ID NO 52
<211> LENGTH: 16
<212> TYPE: DNA
<213> ORGANISM: Artificial Sequence
<220> FEATURE:
<223> OTHER INFORMATION: sequence stretch
<220> FEATURE:
<221> NAME/KEY: misc_feature
<222> LOCATION: (7)..(8)
<223> OTHER INFORMATION: n is a, c, g, or t

<400> SEQUENCE: 52
gaagacnntt gcagcg                                                        16

<210> SEQ ID NO 53
<211> LENGTH: 15
<212> TYPE: DNA
<213> ORGANISM: Artificial Sequence
<220> FEATURE:
<223> OTHER INFORMATION: sequence stretch

<400> SEQUENCE: 53
ccctgccaag tcttc                                                         15

<210> SEQ ID NO 54
<211> LENGTH: 15
<212> TYPE: DNA
<213> ORGANISM: Artificial Sequence
<220> FEATURE:
<223> OTHER INFORMATION: sequence stretch

<400> SEQUENCE: 54
gaagacttgg gagtt                                                         15

<210> SEQ ID NO 55
<211> LENGTH: 15
<212> TYPE: DNA
<213> ORGANISM: Artificial Sequence
<220> FEATURE:
<223> OTHER INFORMATION: sequence stretch

<400> SEQUENCE: 55
gaagacttgg caggg                                                         15

<210> SEQ ID NO 56
<211> LENGTH: 15
<212> TYPE: DNA
<213> ORGANISM: Artificial Sequence
<220> FEATURE:
<223> OTHER INFORMATION: sequence stretch

<400> SEQUENCE: 56
aactcccaag tcttc                                                         15
```

SYSTEM AND METHOD OF MODULAR CLONING

CROSS-REFERENCE TO RELATED APPLICATIONS

This application is a Division of U.S. patent application Ser. No. 13/703,123, now abandoned, which has a 35 U.S.C. § 371(c) date of May 14, 2013 and which is the U.S. National Stage of International Application PCT/EP2011/002843, filed Jun. 9, 2011, which designates the U.S. and was published by the International Bureau in English on Dec. 15, 2011, and which claims the benefit of European Patent Application Nos. 10006090.4, filed Jun. 11, 2010 and 10006955.8, filed Jul. 6, 2010, all of which are hereby incorporated by reference in their entirety.

REFERENCE TO A SEQUENCE LISTING SUBMITTED AS A TEXT FILE

The official copy of the sequence listing is submitted electronically via EFS-Web as an ASCII formatted sequence listing with a file named 070313-0022SEQLST.TXT, created on Aug. 16, 2021, and having a size of 14.8 kilobytes. The sequence listing contained in this ASCII formatted document is part of the specification and is herein incorporated by reference in its entirety.

FIELD OF THE INVENTION

The present invention relates to a cloning system for producing a nucleic acid construct of interest using type IIs restriction endonucleases. The invention also provides a method of producing a nucleic acid construct of interest from at least three nucleic acid fragment constructs.

BACKGROUND OF THE INVENTION

Synthetic biology promises to revolutionize biotechnology through engineering of life forms with novel phenotypes not normally found in nature. Examples of applications include the microbial production of chemical precursors, novel antibiotics and, induction and fine-tuning of pluripotent stem cells and the engineering of a minimal free living cell. Such applications will require the ability to physically assemble complex DNA molecules containing large numbers of natural or artificial genes in a wide variety of arrangements.

Although much progress has been made in the past few years, construction of recombinant DNA molecules is still a slow and labour-intensive process. Recombinant DNA molecules have traditionally been constructed using type II restriction enzymes and ligase. Although versatile, such approach is slow and tedious and only allows creation of constructs of relatively small size and containing only few genes. In particular, this approach is limited by the fact that designing cloning strategies becomes extremely difficult for large constructs, since all restriction enzymes available will cut many times in such constructs. In the past few years, a number of different approaches have been developed to overcome these limitations. These include recombinase-based cloning, ligation-independent cloning, cloning based of homologous recombination and PCR-based assembly. Recombinase-based cloning eliminates the problems coming from the multiple occurrence of restriction sites in large constructs but is limited by the fact that recombination sites are left in the final construct, preventing the seamless assembly of protein coding sequences. Moreover, recombinase-based cloning is limited by the fact that, so far, only 4 fragments can be assembled in one construct simultaneously. Ligation-independent cloning is also independent of restriction sites since restriction enzymes are not used, but is limited by the fact that it requires PCR and therefore requires sequencing of constructs made with this approach. Methods based on homologous recombination are valuable and allow to assemble extremely large DNA fragments of up to the size of entire bacterial genomes (Gibson et al., Science. 2010 Jul. 2; 329(5987):52-6), but are not well suited for combinatorial assembly of multiple independent basic genetic elements since they, but are not well suited for combinatorial assembly of multiple independent basic genetic elements, since they require a minimum amount of sequence in common between modules.

Recently, cloning methods based on type IIs restriction enzymes have been developed (WO 2008/095927). Engler et al. PLoS ONE 4 (2009) e5553) describe a protocol to assemble in one step and one tube at least nine separate DNA fragments together into an acceptor vector using type IIs restriction enzymes by simply subjecting a mix of 10 undigested input plasmids to a restriction-ligation reaction and transforming the resulting mix into competent cells. This protocol was named "Golden Gate" cloning.

Although methods that allow assembly of multiple DNA fragments in one step (such as Golden Gate cloning) are helpful for construction of recombinant DNA molecules, they still do not solve the problem that construct-specific cloning strategies need to be defined at each step of cloning. What is needed for synthetic biology are methods that eliminate the need for construct-specific cloning strategies. A step toward standardization of cloning strategies has been proposed with the BioBrick system (Knight TF, 2003, Idempotent Vector Design for Standard Assembly of BioBricks. MIT Synthetic Biology Working Group Technical Report). This system is based on hierarchical assembly of basic genetic parts, two parts at a time. Assembly of two basic parts using restriction enzymes and ligase results in a composite part that, has the same structure as the basic part in terms of flanking restriction sites (the parts are therefore called idempotent). Since the structure of the composite parts is the same as the structure of the basic parts, the same assembly procedure can be repeated on composite parts to get increasingly complex constructs. However, because this strategy is based on idempotency of the DNA fragments, the BioBrick system is necessarily limited to assembly of two fragments at a time (addition of a part to a plasmid that already contains another part or composite part). This is a serious limitation since synthetic biology will require assembling very large number of DNA fragments, which will be very costly and impractical if assembly is performed two fragments at a time. Moreover, the ability to assemble a large number of fragments in a single step is useful for making combinatorial libraries, for example for making a construct containing all the genes encoding for a biochemical pathway. Such library can be made by assembling in one step all the genes necessary for a biochemical pathway, with multiple variants for each of the genes of the pathway.

GENERAL DESCRIPTION OF THE INVENTION

Departing from the prior art, it is an object of this invention to provide a system that overcomes the limitations of the prior art. Notably, it is an object to provide a system and method that is not limited to the combination of two fragments per reaction. It is another object to provide a system of DNA molecules that allows assembly of a large or even unlimited number of DNA fragments using a fixed set of cloning vectors. The system should allow assembly of multiple DNA fragments at each cloning step, and should allow as many successive steps of cloning as necessary to be performed, continually reusing the same set of vectors. Repetition of these cloning cycles should allow assembly of increasingly larger numbers of DNA fragments in any desired order, resulting in increasingly larger constructs.

Accordingly, the present invention provides:

(1) System for producing a nucleic acid construct of interest, said system comprising:
 a set of n entry DNAs numbered 1 to n, n being an integer of at least 2,
 each of said n entry DNAs comprising in this order:
 (i) a type IIs restriction endonuclease recognition site followed by the cleavage site thereof;
 (ii) a sequence portion linking the cleavage site of said recognition site of item (i) with the cleavage site of the recognition site of the following item (iii), and
 (iii) a cleavage site of a further type IIs restriction endonuclease recognition site followed by the recognition site of said cleavage site;
  the cleavage sites of the type IIs restriction endonuclease recognition sites of
 item (iii) of entry DNAs 1 to n−1 are complementary to the cleavage sites of the type IIs restriction endonuclease recognition sites of item (i) of entry DNAs 2 to n, respectively;
  the cleavage site of the type IIs restriction endonuclease recognition site of item (iii) of entry DNA n is complementary to the cleavage site of the type IIs restriction endonuclease recognition site of item (i) of entry DNA 1 for allowing annealing of complementary single-stranded overhangs formed by restriction at recognition site (i) of entry DNA 1 and at recognition site (iii) of entry DNA n;
  said system further comprising a destination vector comprising in this order:
 (I) a type IIs restriction endonuclease recognition site followed by the cleavage site thereof;
 (II) a vector backbone preferably comprising a selectable marker gene, said vector backbone linking the cleavage sites of said recognition sites of items (I) and the following item (III);
 (III) a further cleavage site of a type IIs restriction endonuclease recognition site followed by the recognition site of said cleavage site, and
 (IV) optionally, an insert between the recognition sites of item (III) and item (I); said cleavage sites of items (I) and (III) being different and non-complementary, said recognition sites of items (I) and (III) being preferably recognitions sites of the same endonuclease.

(2) The system according to (1), wherein a type IIs restriction endonuclease recognising the recognition site (I) of said destination vector can produce a single-stranded overhang from the cleavage site of item (I) that is complementary to the single-stranded overhang producible by the type IIs restriction endonuclease recognising the recognition site (i) of entry DNA numbered 1 for enabling annealing of said complementary single-stranded overhangs and ligation of said destination vector with the DNA segment of item (ii) from entry DNA numbered 1.

(3) The system according to (1) or (2), said system comprising a nucleic acid linker comprising in the following order:
 (a) a type IIs restriction endonuclease recognition site;
 (b) a cleavage site of said recognition site of item (a);
 (c) a cleavage site of a further type IIs restriction endonuclease recognition site of the following item (d);
 (d) a type IIs restriction endonuclease recognition site defining the cleavage site of item (c) and being a recognition site of a type IIs restriction endonuclease different from that of item (a);
 (e) a type IIs restriction endonuclease recognition site, preferably of the same endonuclease as the recognition site of item (d);
 (f) a cleavage site of said recognition site of item (e);
 (g) a cleavage site of a further type IIs restriction endonuclease recognition site of the following item (h);
 (h) a type IIs restriction endonuclease recognition site defining the cleavage site of item (g), preferably of the same endonuclease as the recognition site of item (a);
  said linker being capable of linking a cleavage site of item (iii) of one of a entry DNA numbered 1 to n, preferably of number 1 to n−1, to a cleavage site of item (III) of said destination vector.

(4) The system according to (3), wherein the cleavage site of item (iii) of one of said entry DNAs is complementary to the cleavage site of item (b) of said linker, and
 the cleavage site of item (g) of said linker is complementary to the cleavage site of item (III) of said destination vector.

(5) The system according to any one of (1) to (4), comprising from 1 to n multiple destination vectors numbered 1 to n, each of said 1 to n destination vectors having segments (I) to (III) as defined in (I) and optionally a segment (IV) as defined in (I),
 wherein the cleavage sites of item (III) of all destination vectors are identical and all cleavage sites of item (I) of all destination vectors are unique among the cleavage sites of item (III).

(6) The system according to (3), comprising a set of n nucleic acid linkers numbered 1 to n, each n-th linker comprising items (a) to (h) as defined in (3),
 the cleavage site of item (iii) of each n-th entry DNA is complementary to the cleavage site of item (b) of the n-th linker;
 the cleavage site of item (g) of each n-th linker being complementary to the cleavage site of item (III) of the n-th destination vector;
 whereby each n-th linker being capable of linking a cleavage site of item (iii) of the n-th entry DNA to a cleavage site of item (III) of each n-th destination vector.

(7) The system according to any one of (3), (4) or (6), said linker(s) comprising a marker gene in between items (d) and (e) for enabling selection of cell clones for the presence or absence of said marker gene.

(8) The system according to any one of (1) to (7), wherein each sequence portion of item (ii) of each entry DNA 1 to n comprises a further pair of two type IIs restriction endonuclease recognition sites oriented such that said further pair of recognition sites can be removed from said entry DNAs by treatment with type IIs restriction endonuclease(s) recognising said further pair of recognition sites, said further pair of recognition sites may flank a marker gene for enabling selection of cell clones for the presence or absence of said marker gene;

wherein said further pair of two type IIs restriction endonuclease recognition sites are recognition sites of endonucleases different from the recognition sites of item (i) and item (iii) of (1).

(9) The system according to any one of (1) to (8), wherein the cleavage sites of the recognition sites of item (i) are unique among the item (i) recognition sites of the set of n entry DNAs, and the cleavage sites of the recognition sites of item (iii) are unique among the item (iii) recognition sites within the set of n entry DNAs.

(10) The system according to any one of (1) to (9), each of said n entry DNAs further comprising in the order defined in (1):
(iv) a vector backbone comprising a selectable marker gene.

(11) The system according to any one of (1) to (10), wherein the type IIs restriction endonuclease recognition sites of items (i) and (iii) are recognition sites of the same type IIs restriction endonuclease.

(12) The system according to any one of (1) to (11), wherein the cleavage sites of the recognition sites of item (III) of all destination vectors are identical, and the cleavage sites of the recognition sites of item (I) of all destination vectors are non-identical.

(13) The system according to (3), wherein the cleavage sites of items (b) and (c) have the same sequence and preferably overlap, and wherein the cleavage sites of items (f) and (g) have the same sequence and preferably overlap.

(14) A method of producing a nucleic acid construct of interest from at least m nucleic acid fragment constructs numbered 1 to m, each nucleic acid construct of interest comprising
a sequence segment numbered 1 to m in the order of occurrence in the nucleic acid construct of interest, m being an integer of at least 3;
said method comprising the following steps (A) to (C):
(A) providing said m nucleic acid fragment constructs, each of said m nucleic acid fragment constructs comprising in this order:
(i') a type IIs restriction endonuclease recognition site of the upstream cleavage site of item (ii');
(ii') a sequence segment of said nucleic acid construct of interest, said sequence segment comprising, in this order, an upstream cleavage site of the recognition site of item (i'), a core portion of the sequence segment, and a downstream cleavage site of the recognition site of the following item (iii'), and
(iii') the type IIs restriction endonuclease recognition site of said downstream cleavage site of item (ii');
the downstream cleavage sites of nucleic acid fragment constructs 1 to m−1 are complementary to the upstream cleavage sites of nucleic acid fragment constructs 2 to m, respectively,
the downstream cleavage site of a nucleic acid fragment construct u, wherein u is an integer that is <m and at least 2 is complementary to the upstream cleavage site of the type IIs restriction endonuclease recognition site of item (ii') of nucleic acid fragment 1;
(B) combining nucleic acid fragment constructs 1 to s, wherein s is an integer <u, a destination vector and a linker in the presence of a type IIs restriction endonuclease recognising said type IIs restriction endonuclease recognition sites of items (i') and (iii') and items (I) and (III) of the destination vector defined below and in the presence a DNA ligase in reaction medium compatible with activity of said type IIs restriction endonuclease and said ligase for recombining and ligating, in the following order, the sequence segment (s) of item (ii') of nucleic acid fragment constructs 1 to s and said linker into said destination vector;
said destination vector comprising in this order:
(I) a type IIs restriction endonuclease recognition site followed by the cleavage site thereof complementary to the upstream cleavage site of item (ii') of nucleic acid fragment construct 1;
(II) a vector backbone comprising a selectable marker gene, said vector backbone linking the cleavage sites of said recognition sites of items (I) and the following item (III);
(III) the further cleavage site of a type IIs restriction endonuclease recognition site followed by the recognition site of said cleavage site,
said linker being as defined in item (3), wherein cleavage site (b) of said linker is complementary to the downstream cleavage site of item (ii') of nucleic acid fragment construct s, and wherein cleavage site (g) of said linker and the cleavage site of item (III) of the destination vector are complementary; and
(C) treating a mixture comprising the recombination product of step (B) and nucleic acid fragment construct (s) s+1 to m with a type IIs restriction endonuclease recognising said type IIs restriction endonuclease recognition sites of items (i') and (iii'), a type IIs restriction endonuclease recognising said type IIs restriction endonuclease recognition sites of items (d) and (e) of the linker and a DNA ligase in a reaction medium compatible with activity of said type IIs restriction endonucleases and said ligase for inserting the sequence segments of item (ii') of nucleic acid fragment constructs s+1 to m and optionally a further linker as defined in item (3) into the cleavage sites provided by items (c) and (f) of the linker used in step (B).

(15) The method according to (14), wherein the recognition sites of all nucleic acid fragment constructs of items (i') and (iii'), the recognition sites of items (a) and (h) of the linker and the recognition sites of item (I) and (III) of the destination vector are recognition sites of the same type IIs restriction endonuclease.

(16) System for producing a nucleic acid construct of interest, said system comprising:
a set of n entry DNAs numbered 1 to n, n being an integer of at least 2, preferably at least 3,
each of said n entry DNAs comprising in this order:
(i) a type IIs restriction endonuclease recognition site followed by the cleavage site thereof;
(ii) a DNA segment linking the cleavage site of said recognition site of item (i) with the cleavage site of the recognition site of the following item (iii), and
(iii) a cleavage site of a further type IIs restriction endonuclease recognition site followed by the recognition site of said cleavage site;
the cleavage sites of the type IIs restriction endonuclease recognition sites of item (iii) of entry DNAs 1 to n−1 are complementary to the cleavage sites of the type IIs restriction endonuclease recognition sites of item (i) of entry DNAs 2 to n, respectively;
all cleavages sites of item (i) are typically unique among said n entry DNAs, and all cleavage sites of item (iii) are typically unique among said n entry DNAs;
said system further comprising a destination vector comprising in this order:

(I) a type IIs restriction endonuclease recognition site followed by the cleavage site thereof;
(II) a vector backbone comprising a selectable marker gene, said vector backbone linking the cleavage sites of said recognition sites of items (I) and the following item (III);
(III) a further cleavage site of a type IIs restriction endonuclease recognition site followed by the recognition site of said cleavage site, and
(IV) optionally, a linker between the recognition sites of item (III) and item (I);
said system further comprising a nucleic acid linker comprising in the following order:
(a) a type IIs restriction endonuclease recognition site;
(b) a cleavage site of said recognition site of item (a);
(c) a cleavage site of a further type IIs restriction endonuclease recognition site of the following item (d);
(d) a type IIs restriction endonuclease recognition site defining the cleavage site of item (c) and being a recognition site of a type IIs restriction endonuclease different from that of item (a);
(e) a type IIs restriction endonuclease recognition site, preferably of the same endonuclease as the recognition site of item (d);
(f) a cleavage site of said recognition site of item (e);
(g) a cleavage site of a further type IIs restriction endonuclease recognition site of the following item (h);
(h) a type IIs restriction endonuclease recognition site defining the cleavage site of item (g), preferably of the same endonuclease as the recognition site of item (a); said linker being capable of linking a cleavage site of item (iii) of one of a entry DNA numbered 1 to n, preferably of number 1 to n−1, to a cleavage site of item (III) of said destination vector.

(17) The system according to (16), comprising the same number n of said linkers as the system comprises entry DNAs, said linkers being numbered 1 to n,
wherein all linkers have the same cleavage site (g) that is complementary to the cleavage site of item (III) of said destination vector for linking each linker to the recognition site of item (III) of said destination vector, and
wherein each of said n linkers has a different cleavage site (b) that is complementary to the cleavage site of item (iii) of one of said n entry DNAs.

(18) The system according to (17), said system further comprising n different destination vectors, each destination vector being defined by items (I) to (IV) and having the same cleavage site of item (III) that is complementary to the cleavage site (g) of all linkers,
each of said destination vectors having a different cleavage site if item (I) that is complementary to the cleavage site of item (i) of one of said n entry DNAs.

(19) System for producing a nucleic acid construct of interest, said system comprising:
a set of m nucleic acid fragment constructs numbered 1 to m, m being an integer of at least 2, preferably at least 3,
each of said m nucleic acid fragment constructs comprising in this order:
(i') a type IIs restriction endonuclease recognition site of the upstream cleavage site of item (ii');
(ii') a sequence segment of said nucleic acid construct of interest, said sequence segment comprising, in this order, an upstream cleavage site of the recognition site of item (i'), a core portion of the sequence segment, and a downstream cleavage site of the recognition site of the following item (iii'), and
(iii') a type IIs restriction endonuclease recognition site of said downstream cleavage site of item (ii');
the downstream cleavage sites of nucleic acid fragment constructs 1 to m−1 are complementary to the upstream cleavage sites of nucleic acid fragment constructs 2 to m, respectively;
said system further comprising a destination vector comprising in this order:
(I) a type IIs restriction endonuclease recognition site followed by the cleavage site thereof;
(II) a vector backbone comprising a selectable marker gene, said vector backbone linking the cleavage sites of said recognition sites of items (I) and the following item (III);
(III) a further cleavage site of a type IIs restriction endonuclease recognition site followed by the recognition site of said cleavage site, and
(IV) optionally, an insert between the recognition sites of item (III) and item (I); said cleavage sites of items (I) and (III) being different and non-complementary, said recognition sites of items (I) and (III) being recognitions sites of the same endonuclease.

(20) The system of item (19), wherein the downstream cleavage site of a nucleic acid fragment construct u, wherein u is an integer that is <m and at least 2 is complementary to the upstream cleavage site of the type IIs restriction endonuclease recognition site of item (ii') of nucleic acid fragment 1.

(21) System for producing a nucleic acid construct of interest, said system comprising:
a set of n destination vectors ("destination vectors M"), n being an integer of at least 2, preferably at least 3,
each of said n destination vectors M comprising in the following order:
(I') a type IIs restriction endonuclease recognition site defining the cleavage site of item (II');
(II') the cleavage site of said recognition site of item (I');
(III') a cleavage site of said recognition site of the following item (IV');
(IV') a further type IIs restriction endonuclease recognition site defining the cleavage site of item (III') and being a different recognition site of a type IIs restriction endonuclease from that of item (I');
(V') a vector backbone comprising a selectable marker gene, said vector backbone linking the cleavage sites of said recognition sites of item and (IV') and the following item (VI');
(VI') a further type IIs restriction endonuclease cleavage site;
(VII') a type IIs restriction endonuclease recognition site of the cleavage site of item (VI'), preferably of the same type IIs restriction endonuclease as the recognition site of item (I') and
(VIII') optionally, an insert between the recognition sites of item (VII') and item (I'); and
a set of n linkers M, n being as defined above, each linker M comprising in the following order:
(a') a type IIs restriction endonuclease recognition site defining the cleavage site of item (b');
(b') the cleavage site of said recognition site of item (a');
(c') a cleavage site of a further type IIs restriction endonuclease recognition site of item (d'), said cleavage site having the same sequence of nucleotides as the cleavage site of item (b');
(d') the type IIs restriction endonuclease recognition site defining the cleavage site of item (c') and being a different recognition site of a type IIs restriction endonuclease different from that of item (a');

(e') a further cleavage site of a type IIs restriction endonuclease recognition site of the following item (f);

(f') the type IIs restriction endonuclease recognition site defining the cleavage site of item (e'), that is preferably a recognition site of the same endonuclease as the recognition site of item (a');

wherein the cleavage sites (VI') of all n destination vectors M are identical;

the cleavage sites (e') of all n linkers M are identical;

the cleavage site of item (VI') of each destination vector M is complementary to the cleavage site of item (e') of each linker M for allowing annealing of single-stranded overhangs produced by the type IIs restriction endonuclease recognising recognition sites (VII') and (f);

the cleavage sites of items (II') and (III') within each destination vector M have the same sequence of nucleotides and may overlap such that one and the same sequence of nucleotides provides the cleavage site of items (II') and that of item (III'); and the cleavage sites of items (b') and (c') within each linker M have the same sequence of nucleotides and may overlap such that one and the same sequence of nucleotides provides the cleavage site of items (b') and that of item (c'); and the cleavage site (II') of each destination vector M is unique among the cleavage sites (II') of the set of n destination vectors M such that there are n different cleavage sites (II'), wherein for each of said n different cleavage sites (II'), there is a linker M having a cleavage site (b') of identical nucleotide sequence among the set of n linkers M.

(22) The system according to item (21), comprising:

a set of z entry DNAs numbered 1 to z, z being an integer of at least 2, preferably an integer of at least 3, each of said z entry DNAs comprising in this order:

(i) a type IIs restriction endonuclease recognition site followed by the cleavage site thereof;

(ii) a sequence portion linking the cleavage site of said recognition site of item (i) with the cleavage site of the recognition site of the following item (iii), and (iii) a cleavage site of a further type IIs restriction endonuclease recognition site followed by the recognition site of said cleavage site;

wherein the cleavage site of item (i) of each entry DNA is complementary to the cleavage site of item (II') of one of the n destination vectors M for allowing annealing of single-stranded overhangs produced by the type IIs restriction endonuclease recognising recognition sites of items (i) and (I'), the recognition sites of item (i) of all z entry DNAs are preferably recognition sites of the same type IIs restriction endonuclease as the recognition sites of item (I') and (VII');

the cleavage site of item (iii) of each entry DNA is complementary to the cleavage sites of item (b') of one of the n linkers M for allowing annealing of single-stranded overhangs produced by the type IIs restriction endonuclease recognising recognition sites of items (iii) and (a'), the recognition sites of item (i) are recognition sites of the same type IIs restriction endonuclease as the recognition sites of item (a') and (f); and the recognition sites of items (i) and (iii) of all z entry DNAs are recognition sites of the same type IIs restriction endonuclease.

(23) The system according to any one of items (21) or (22), further comprising a set of n destination vectors ("destination vectors P"), wherein n is as defined in item (21), each of said n destination vectors P comprising in the following order:

(I") a type IIs restriction endonuclease recognition site defining the cleavage site of item (II");

(II") the cleavage site of said recognition site of item (I");

(III") a cleavage site of said recognition site of the following item (IV");

(IV") a further type IIs restriction endonuclease recognition site defining the cleavage site of item (III") and being a different recognition site of a type IIs restriction endonuclease from that of item (I");

(V") a vector backbone comprising a selectable marker gene, said vector backbone linking the cleavage sites of said recognition sites of item and (IV") and the following item (VI");

(VI") a further type IIs restriction endonuclease cleavage site;

(VII") a type IIs restriction endonuclease recognition site of the cleavage site of item (VI"), preferably of the same endonuclease as the recognition site of item (I") and (VIII") optionally, an insert between the recognition sites of item (VII") and item (I"); and a set of n linkers P, each linker P comprising in the following order:

(a") a type IIs restriction endonuclease recognition site defining the cleavage site of item (b");

(b") the cleavage site of said recognition site of item (a");

(c") a cleavage site of a further type IIs restriction endonuclease recognition site of item (d"), said cleavage site having the same nucleotide sequence as the cleavage site of item (b");

(d") the type IIs restriction endonuclease recognition site defining the cleavage site of item (c") and being a different recognition site of a type IIs restriction endonuclease from that of item (a");

(e") a further cleavage site of a type IIs restriction endonuclease recognition site of the following item (f");

(f") the type IIs restriction endonuclease recognition site defining the cleavage site of item (e"), that is preferably a recognition site of the same endonuclease as the recognition site of item (a");

wherein the cleavage sites (VI") of all n destination vectors P are identical;

the cleavage sites (e") of all n linkers P are identical;

the cleavage site of item (VI") of each destination vector P is complementary to the cleavage site of item (e") of each linker P for allowing annealing of single-stranded overhangs produced by the type IIs restriction endonuclease recognising recognition sites (VII") and (f");

the cleavage sites of items (II") and (III") within each destination vector P have the same sequence of nucleotides and may overlap such that one and the same sequence of nucleotides provides the cleavage site of item (II") and the cleavage site of item (III");

the cleavage sites of items (b") and (c") within each linker P have the same sequence of nucleotides and may overlap such that one and the same sequence of nucleotides provides the cleavage site of items (b") and the cleavage site of item (c"); and for each of said n different cleavage sites (b') or (II'), there is a destination vector P having a cleavage site (II") of identical nucleotide sequence as the nucleotide sequence of cleavage sites (b') or (II'); and for each of said n different cleavage sites (b') or (II'), there is a linker P having a cleavage site (b") of identical nucleotide sequence as the nucleotide sequence of cleavage sites (b') or (II').

BRIEF DESCRIPTION OF THE DRAWINGS

FIG. 1A shows elements of a system that allows re-use of the entry DNAs of the invention (level 1 destination vectors) for different inserted sequence segments.

FIG. 1B provides an example for cloning of three nucleic acid fragment constructs na1, na2, and na3 into a destination vector using end-linker EL3.

FIG. 10 shows the efficiency of cloning for different levels of assembly.

FIGS. 18A-18C show the structure of transcriptional units, level 0 modules, and of destination vectors required for their cloning. FIG. 18A: The transcriptional units contain up of 5 basic modules separated by 4 nucleotides sequences that serve as recombination sites (shown in boxes). FIG. 18B: Level 0 modules shown on the first line are flanked by BsaI sites.

FIG. 18C: Strategy for removing internal type IIS recognition sequences.

FIGS. 19A-19D show an example for cloning of constructs of level 0, 1 and 2. Antibiotic resistances are indicated. FIG. 19A: Illustrates cloning of level 0 promoter modules. FIG. 19B: Illustrates cloning of a level 1 construct containing a transcription unit. FIG. 19C: Illustrates cloning of a level 2i-1 construct containing 5 transcription units, TU1 (containing GFP), TU2 (containing p19), TU3 (containing VP2), TU4 (containing VP5), TU5 (containing VP7) into destination vector pL2-1. FIG. 19D: Illustrates cloning of a level 2-2 construct containing 11 transcription units. In addition to TU1 to TU5, the construct contains TU6 (transcription unit with VP3), TU7 (transcription unit with BAR), TU8 (transcription unit with antibody light chain), TU9 (transcription unit with antibody heavy chain), TU10 (transcription unit with TMV MP), TU11 (transcription unit with TMV CP).

FIG. 20A shows the structure of the 11 level 1 transcription units used in FIG. 19B.

FIG. 20B shows the structure of construct pICH51811 that is obtained by cloning of the 11 transcription units cloned in a level 2-2 construct.

FIG. 22 shows prokaryotic genes cloned as level 0 entry modules.

FIG. 29A shows a set of destination vectors and end-linkers for assembly of several level 1 transcription units (or more generally nucleic acids "na") into a level M destination vector (M stands for multiplication). FIG. 29B illustrates assembly of three transcription units (nucleic acid acids na1 to 3) in a level M destination vector.

DETAILED DESCRIPTION OF THE INVENTION

Figure 1C:
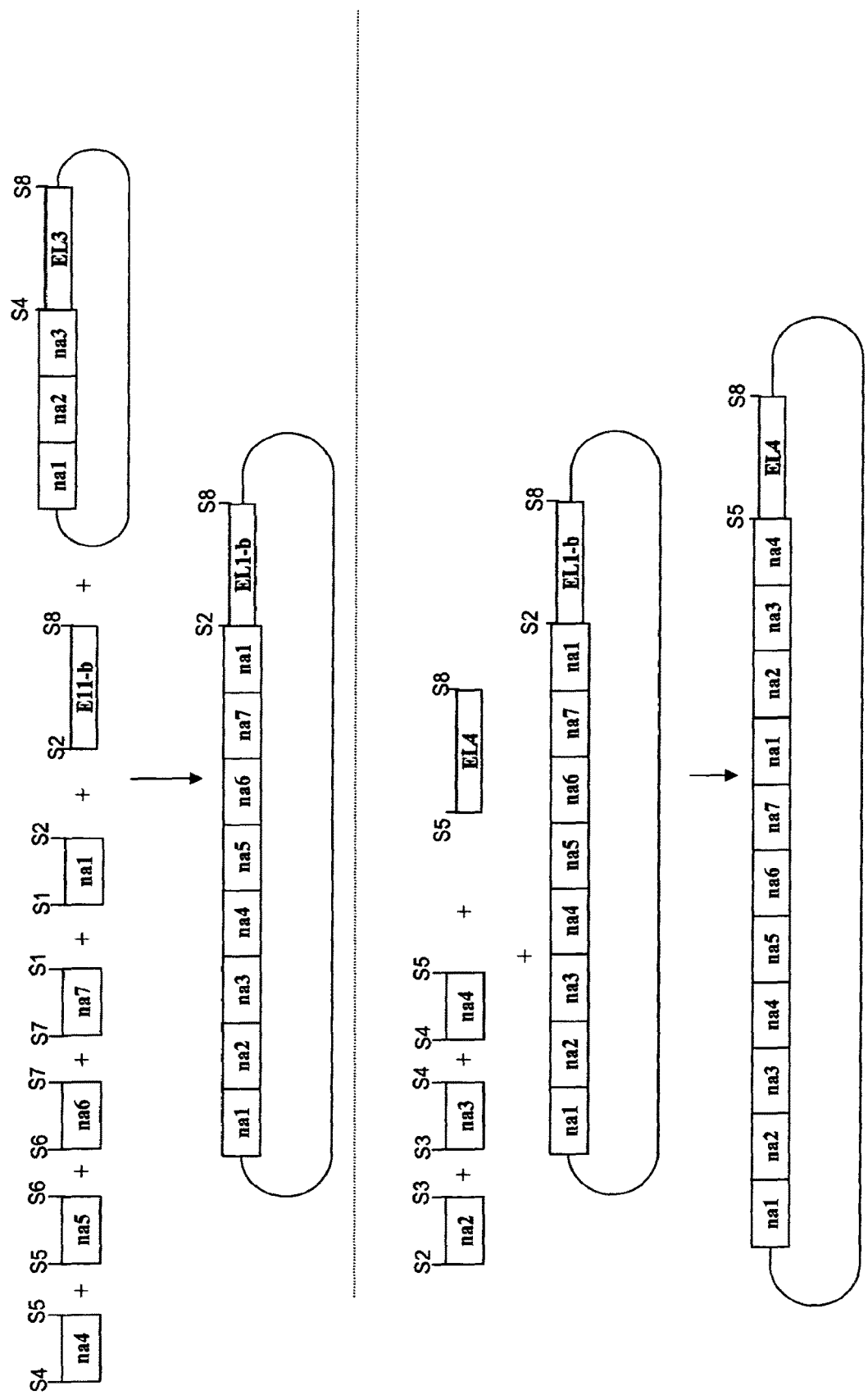
FIG. 1C shows that further nucleic acid fragment constructs na4 to na7 and a further construct na1 that is based on the same entry vector number 1 as na1 ligated in FIG. 1B can be cloned into the product vector obtained in FIG. 1B.

The system of the invention comprises a defined set of components that have a high versatility and flexibility, whereby a given system can be easily applied to many different applications. Notably, a given system can be used for applications comprising different numbers of fragments to be assembled in a nucleic acid construct of interest. It is a great advantage of the invention that many different fragments can be combined with a number of acceptor vectors that is smaller than the number of fragments to be combined. Therefore, the system can be scaled to the combination of many different fragments and fragment numbers with little or no extra cloning work for the adaption of acceptor vectors to a large number of fragments.

This system provides three advantages: (1) the cloning system allows to assemble constructs from multiple DNA fragments at each cloning step (using Golden Gate cloning), (2) the cloning procedure is automatically defined by the number of genetic elements that the user wants to assemble and does not require construct-specific cloning strategies and can therefore easily be automatized, (3) the cloning procedure can be repeated indefinitely using the same set of cloning vectors to make increasingly complex constructs (with an increasingly higher number of multigene and/or genetic elements.

In the invention, a nucleic acid construct of interest is a DNA assembled from m nucleic acid fragment constructs, m being an integer of at least 3. Each nucleic acid fragment construct provides a sequence segment to the nucleic acid construct of interest. Typically, the nucleic acid construct of interest is present in a vector having in its backbone a selectable marker for allowing selection of cells containing the vector. The nucleic acid construct of interest is produced in the invention in a process comprising at least two, typically three, steps of restriction and ligation, for example departing from standardised pre-prepared modules. Restriction is catalysed by a type IIs restriction endonuclease, ligation is catalysed by a ligase.

In a first step of restriction and ligation corresponding to step (A) of the method of the invention (also referred herein as "level 1" or "level 1 reaction"), at least one, preferably at least 2, nucleic acid modules are linked by restriction and ligation and at the same time inserted into an acceptor vector. Acceptor vectors are referred to herein as "destination vectors". Thus, the acceptor vectors of the level 1 reaction are also referred to herein as "level 1 destination vectors" or "level 1 acceptor vector". The level 1 acceptor or destination vectors are also referred to herein as "entry DNAs". The reaction products of the level 1 reaction are referred to as "level 1 constructs" or "nucleic acid fragment constructs", the latter terms being equivalent herein. The term "construct" herein indicates a reaction product of a restriction and ligation reaction. Thus, a level 1 destination vector is a reactant of the level 1 reaction, and the nucleic acid fragment constructs are the products of the level 1 reaction. Multiple level 1 reactions are generally conducted separately to obtain at least two different nucleic acid fragment constructs to be assembled in the second step, referred to herein as "level 2" (see further below). One purpose of the level 1 reaction is to provide the nucleic acid fragment constructs to be assembled in the next step with suitable cleavage sites of a type IIs restriction endonuclease to allow ligation of the constructs obtained on level 1 in the desired order on level 2. In some embodiments, the level 1 reaction further serves the purpose of constructing nucleic acid fragment constructs from 2 or more modules. For example, if the nucleic acid construct of interest comprises several eukaryotic transcription units, multiple individual transcription units can be assembled in separate level 1 reactions from 2 or more modules (such as promoter, 5' UTR, signal peptide sequence etc.). On level 2, two or more transcription units can then be combined. In a further level 2 reaction, one or more further nucleic acid construct each containing a transcription unit can be combined with the reaction product of the first level 2 reaction. It is, however, not compulsory to produce the nucleic acid fragment constructs using such level 1 reaction. It could also be considered to engineer them by other means or to synthesise them artificially de novo.

In the second step of restriction and ligation corresponding to step (B) of the method of the invention (referred herein as "level 2"), at least 2 nucleic acid fragment constructs obtained in the previous level 1 step are combined by restriction and ligation and, in the same reaction, inserted into an acceptor vector. This acceptor vector of the level 2 reaction is referred to as "level 2 destination vector". If the term "destination vector" is used without reference to a particular level, it refers to a level 2 destination vector. The reaction product of the level 2 reaction is referred to as "level 2 construct". In some embodiments, the level 2 construct is the nucleic acid construct of interest. In other embodiments, such as in the method of the invention, the level 2 reaction is followed by a further reaction step (step (C)) that may be referred to as "level 2-2", indicating a second level 2 reaction. In the first level 2 reaction, a nucleic acid linker (also simply referred to as "linker" or "end-linker" herein) is preferably used that links one of the at least two nucleic acid fragment constructs to one of the cleavage sites of the level 2 destination vector. Use of the linker or multiple linkers significantly improves the versatility and flexibility of the systems of the invention in that different nucleic acid fragment constructs can be inserted into a given destination vector, whereby a given destination vector can be used independent of the cleavage site of the nucleic acid fragment construct. Moreover, the linkers allow introduction of a type IIs restriction site for re-opening the level 2 reaction product for insertion of further nucleic acid fragment constructs in a further step of restriction and ligation (step (C)) as will be described below.

The term "module" is used herein to refer to the starting compound of a level 1 reaction other than the level 1 destination vector. Thus, a module is a reactant of a restriction and ligation reaction that reacts with a level 1 destination vector. The modules of a level 1 reaction can be produced in a level 0 reaction (see further below). Thus, the modules of the level 1 reaction can be the products of a level 0 reaction.

Figure 4:
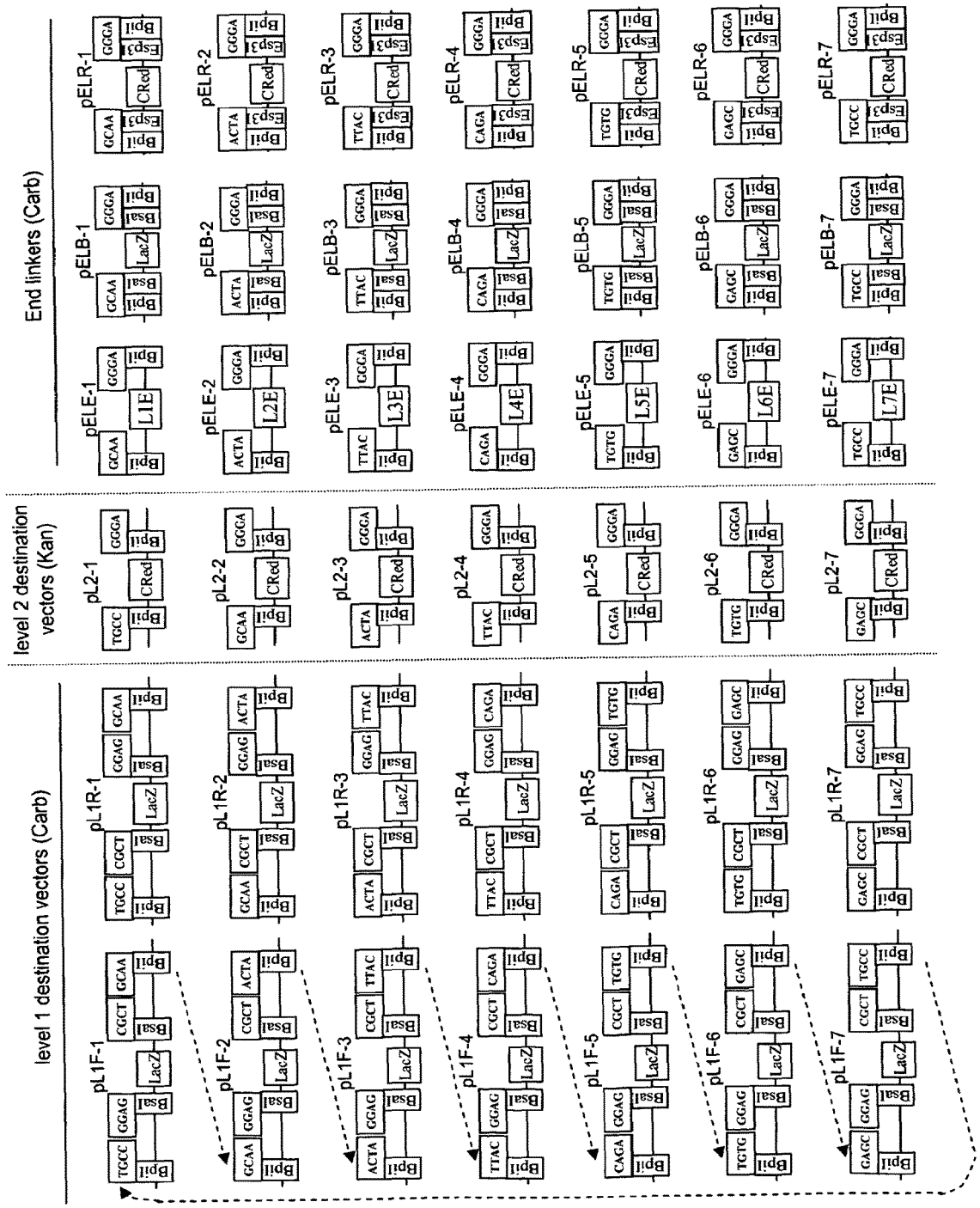
FIG. 4 depicts a set of level 1 destination vectors, level 2 destination vectors, and end-linkers.

The system of the invention comprises a set of n entry DNAs and at least one destination vector. n is an integer of at least 2, in another embodiment of at least 3. Conveniently, n may be between 3 and 10. In the figures, examples with sets of n=7 entry DNAs are presented (FIG. 4). As mentioned above, the term "entry DNA" refers to acceptor vectors of the level 1 reaction. The destination vector is an acceptor vector of the level 2 reaction. Thus, the entry DNAs and the at least one destination vector of the system are key components for performing both the level 1 and the level 2 reaction. The entry DNAs of the system of the invention allow combination of the multiple nucleic acid fragment constructs produced from multiple entry DNAs in a desired order and insertion into the level 2 destination vector in the level 2 reaction. The entry DNAs are numbered consecutively with integers starting from 1 in the order in which inserts inserted into level 1 reaction can be assembled into the nucleic acid construct of interest in a subsequent step. Entry DNAs differing in their numbering by 1 are referred to as contiguous entry DNAs. For allowing combination of entry DNAs and/or fragment constructs derived from the entry DNAs in a desired order in a level 2 reaction, each of said n entry DNAs comprises in this order:

(i) a type IIs restriction endonuclease recognition site followed by the cleavage site thereof;
(ii) a sequence portion linking the cleavage site of said recognition site of item (i) with the cleavage site of the recognition site of the following item (iii), and
(iii) a cleavage site of a further type IIs restriction endonuclease recognition site followed by the recognition site of said cleavage site.

The cleavage sites of the type IIs restriction endonuclease recognition sites of item (iii) of entry DNAs 1 to n−1 are complementary to the cleavage sites of the type IIs restriction endonuclease recognition sites of item (i) of entry DNAs 2 to n, respectively. Being complementary means that single-stranded overhangs produced by restriction with a type IIs restriction endonuclease recognising the recognition sites of the cleavage sites are complementary such that the single stranded overhangs can anneal and be ligated after annealing to form a linear DNA. Thus, the first entry DNA can anneal with its end represented by item (iii) to the end represented by item (i) of the second entry DNA. The second entry DNA can anneal with its end represented by item (iii) to the end represented by item (i) of the third entry DNA etc. This is illustrated by the dashed arrows in FIG. 4 that link the right hand side of the level 1 destination vectors with the left hand side of the level 1 destination vector underneath.

Generally, all item (i) cleavage sites are unique and non-complementary among the n entry DNAs of the system of the invention, and all item (iii) cleavage sites of all entry DNAs are unique and non-complementary among the n entry DNAs of the invention. In a given entry DNA, the cleavage sites of items (i) and (iii) are preferably non complementary in order to avoid ligating multiple identical fragment constructs contiguously. It is also preferred that the recognition sites of items (i) and (iii) among all entry DNAs are recognitions sites of the same endonuclease so that the associated cleavage sites can be cleaved using the same type IIs restriction endonuclease. However, it is also possible that the recognition sites of different entry DNAs are recognition sites of different type IIs restriction endonucleases. In this case, multiple endonucleases will have to be used in a given level 2 reaction to ensure that all required cleavage sites are cleaved. The single-stranded overhangs formed from the cleavage sites by type IIs restriction enzyme cleavage are preferably non-palindromic.

In a preferred embodiment, the cleavage site of the type IIs restriction endonuclease recognition site of item (iii) of entry DNA n is complementary to the cleavage site of the type IIs restriction endonuclease recognition site of item (i) of entry DNA 1 for allowing annealing of complementary single-stranded overhangs formed by restriction at recognition site (i) of entry DNA 1 and at recognition site (iii) of entry DNA n. This feature is illustrated in the long dashed arrow linking the TGCC cleavage site of the level 1 destination vector pL1F-7 with the TGCC cleavage site of the level 1 destination vector pL1F-1 (FIG. 4). As will be described in more detail below, this allows reuse of the first and optionally further entry DNAs in a second level 2 reaction so that more nucleic acid fragment constructs can be combined to produce a nucleic acid construct of interest than the system has entry DNAs.

The entry DNAs may be circular plasmids or vectors, wherein items (i) and (iii) of the entry DNAs are linked by a vector backbone. The vector backbone may contain a selectable marker allowing selection of cell clones containing the entry DNA or the nucleic acid fragment construct obtained therefrom in the level 1 reaction.

The system further comprises a destination vector (level 2 destination vector) comprising in this order:
(I) a type IIs restriction endonuclease recognition site followed by the cleavage site thereof;
(II) a vector backbone comprising a selectable marker gene, said vector backbone linking the cleavage sites of said recognition sites of items (I) and the following item (III);
(III) a further cleavage site of a type IIs restriction endonuclease recognition site followed by the recognition site of said cleavage site, and
(IV) optionally, an insert between the recognition sites of item (III) and item (I);

In the destination vector, the cleavage sites of items (I) and (III) are different and non-complementary. Preferably, the recognition sites of items (I) and (III) are recognition sites of the same endonuclease so that the associated cleavage sites can be cleaved using the same type Its restriction endonuclease. For convenience, the recognition sites of items (I) and (III) are further recognitions sites of the same endonuclease as the recognition sites of items (i) and (iii) of the entry DNAs, so that the level 2 reaction can be performed using one type IIs restriction endonuclease.

For enabling ligation of multiple nucleic acid fragment constructs into the destination vector, the type IIs restriction endonuclease recognising the recognition site (I) of said destination vector can produce a single-stranded overhang from the cleavage site of item (I) that is complementary to the single-stranded overhang producible by the type IIs restriction endonuclease recognising the recognition site (i) of entry DNA numbered 1 for enabling annealing of said complementary single-stranded overhangs and ligation of said destination vector with the DNA segment of item (ii) from entry DNA numbered 1. In the terminology used herein, the cleavage site of item (i) of entry DNA 1 and the cleavage site of item (I) of the destination vector are complementary. Alternatively, the type IIs restriction endonuclease recognising the recognition site (I) of a destination vector can produce a single-stranded overhang from the cleavage site of item (I) that is complementary to the single-stranded overhang producible by the type Its restriction endonuclease recognising the recognition site (i) of an entry DNA other than 1, such as 2 or 3. Such destination vectors are depicted in FIG. 4.

For inserting a ligation product from multiple nucleic acid fragment constructs into the destination vector, the cleavage site of item (III) of the destination vector may be made complementary to the cleavage site of the entry DNA that will be linked to the cleavage site of item (III). However, in the present invention nucleic acid linkers may be used for this purpose, since suitable linkers allow to link any item (iii) cleavage site to the item (III) cleavage site of the destination vector without the need for producing a destination vector for each possible downstream (item (iii)) cleavage site of the entry DNAs. Since the specific item (iii) cleavage site of an entry DNA or nucleic acid fragment construct depends, for a given set of entry DNAs, from the number of fragment constructs to be combined in the level 2 reaction, the linkers provide the system with a broad applicability to many different real life applications. Notably, a given system can be applied to cases with different numbers of fragment constructs to be recombined. An advantageous linker comprise in the following order:

(a) a type IIs restriction endonuclease recognition site;
(b) a cleavage site of said recognition site of item (a);
(c) a cleavage site of a further type IIs restriction endonuclease recognition site of the following item (d);
(d) a type IIs restriction endonuclease recognition site defining the cleavage site of item (c) and being a recognition site of a type IIs restriction endonuclease different from that of item (a);
(e) a type IIs restriction endonuclease recognition site, preferably of the same endonuclease as the recognition site of item (d);
(f) a cleavage site of said recognition site of item (e);
(g) a cleavage site of a further type IIs restriction endonuclease recognition site of the following item (h);
(h) a type IIs restriction endonuclease recognition site defining the cleavage site of item (g), preferably of the same endonuclease as the recognition site of item (a).

The linkers may be linear DNA molecules. Generally, however, the linkers are circular plasmids. The linkers comprise a pair of type IIs restriction endonuclease recognition sites (items (a) and (h)) and associated cleavage sites (items (b) and (g)) at both ends for linking a given item (iii) site with an item (III). This pair of restriction sites is in convergent orientation, which means that the two cleavage sites are oriented toward the center of the linker, while the recognition sites are oriented towards the termini of the linker so that the recognition sites are removed upon restriction. Examples of linkers are linkers pELB-1 to -7 and pELR-1 to -7 shown in FIG. 4.

The linkers preferably comprise a further, different, pair of type IIs restriction sites flanked by the pair formed by items (a), (b), (g) and (h) of the linker. This further pair is formed by items (c) to (f) of the linker and is in divergent orientation, which allows to reopen a level 2 reaction product produced using such linker for insertion of further nucleic acid fragment constructs.

The cleavage site of item (b) is complementary to an item (iii) cleavage site of an entry DNA for being capable of linking a cleavage site of item (iii) of one of a entry DNAs numbered 1 to n, preferably of number 1 to n–1, to a cleavage site of item (III) of said destination vector. The cleavage site of item (g) of the linker is complementary to the cleavage site of item (III) of the linker.

The linkers may be provided as part of a plasmid containing the linker elements (a) to (h) defined above and a plasmid backbone linking elements (a) and (h). The backbone may contain a selectable marker for selecting cells containing the plasmid using a selective agent. This allows storage and amplification of linkers in cells, notably bacterial cells.

In a preferred embodiment, the system comprises a set of n nucleic acid linkers numbered 1 to n, each n-th linker comprising items (a) to (h), the cleavage site of item (iii) of each n-th entry DNA is complementary to the cleavage site of item (b) of the n-th linker; the cleavage site of item (g) of each n-th linker being complementary to the cleavage site of item (III) of the n-th destination vector. Thus, each n-th linker is capable of linking a cleavage site of item (iii) of the n-th entry DNA to a cleavage site of item (III) of each n-th destination vector. In this embodiment, the system contains the same number of n entry DNAs and linkers. For each entry DNA of the set of n entry DNA, a linker is provided allowing linking the item (iii) cleavage site to the item (III) cleavage site of the destination vector. Thus for a given destination vector, all item (g) cleavage sites of the set of n linkers can be identical. As an example, FIG. 4 shows a set of 7 entry vectors (level 1 destination vectors) PL1F-1 to -7 and a set of linkers pELB-1 to -7. Each of the n linkers of the set of n linkers may be part of a plasmid.

The cleavage sites of items (b) and (c) within each linker may have the same sequence of nucleotides and may overlap such that one and the same sequence of nucleotides provides the cleavage site of items (b) and that of item (c). Similarly, the cleavage sites of items (f) and (g) within each linker may have the same sequence of nucleotides and may overlap such that one and the same sequence of nucleotides provides the cleavage site of items (f) and that of item (g).

In some embodiments, it may be desired to use a given entry DNA of number >1 at a position 1 in the reaction product of the level 2 reaction. For this purpose, the system of the invention may comprise from 1 to n multiple destination vectors numbered 1 to n, each of said 1 to n destination vectors having segments (I) to (III) as defined above and optionally a segment (IV) as defined above. The cleavage sites of item (III) of all destination vectors may be identical and all cleavage sites of item (I) of all n destination vectors may be unique among the cleavage sites of item (III). Preferably, the n-th item (I) cleavage site of all n destination vectors is complementary to the n-th item (i) cleavage site of the entry DNA. An example of such embodiment is given in FIG. 4 that shows a set of 7 level 2 destination vectors having identical item (III) cleavage sites (GGGA) that are complementary to the GGGA cleavage sites of the linkers. The item (I) cleavage sites of each level 2 destination vector is complementary to the level 1 destination vector shown in the same line in the left-most column.

The optional insert of item (IV) of the destination vector(s) may be any sequence linking items (III) and (I), whereby the destination vector will be a circular molecule of vector. Absence of the insert of item (IV) may mean that the destination vector is linear DNA molecule. Preferably, however, an insert is used that is or comprises a marker gene that allows to distinguish cell clones containing the destination vector from those containing the product of the level 2 reaction. Since the restriction sites of the destination vector are in divergent orientation with respect to the insert (see FIG. 4), the insert is lost in the level 2 reaction. Thus, destination vectors and level 2 reactions products can be distinguished by the absence of red color in cell clones containing the latter.

In the invention, entry DNAs and nucleic acid fragment constructs differ in that the latter contain a sequence segment (item (ii')) of the nucleic acid construct of interest to be produced. For allowing introduction of such sequence segment with its core portion into the entry DNA in a level 1 reaction, each sequence portion of item (ii) of each entry DNA 1 to n generally comprises a further pair of two type IIs restriction endonuclease recognition sites oriented such that said further pair of recognition sites can be removed from said entry DNAs by treatment with type IIs restriction endonuclease(s) recognising said further pair of recognition sites. In FIG. 4, the further pair of two recognition sites are the BsaI sites in the level 1 destination vectors. The sequence region of item (ii) is not particularly restricted and may be as short as a few nucleotides. In one embodiment, however, the sequence region of item (ii) contains a reporter gene or reporter genes allowing color selection of cell clones containing the reporter gene(s). Said further pair of recognition sites may flank the reporter gene for enabling selection of cell clones for the presence or absence of said reporter gene e.g. by color. In FIG. 4, the reporter gene is lacZ flanked by a pair of BsaI sites. The further pair of two type IIs restriction endonuclease recognition sites are recognition sites of endonucleases different from those of recognition sites of item (i) and item (iii) so that a given endonuclease does not cleave a cleavage site of the further pair and, at the same time, a recognition site of item (i) or (iii). The orientation of the further pair of recognition sites is divergent with respect to the marker gene, so that the reporter gene and the recognition sites is removed upon treatment with the type IIs endonuclease recognising these site, so that these recognition sites are not present in the nucleic acid fragment construct obtained in the level 1 reaction.

Figure 5A:
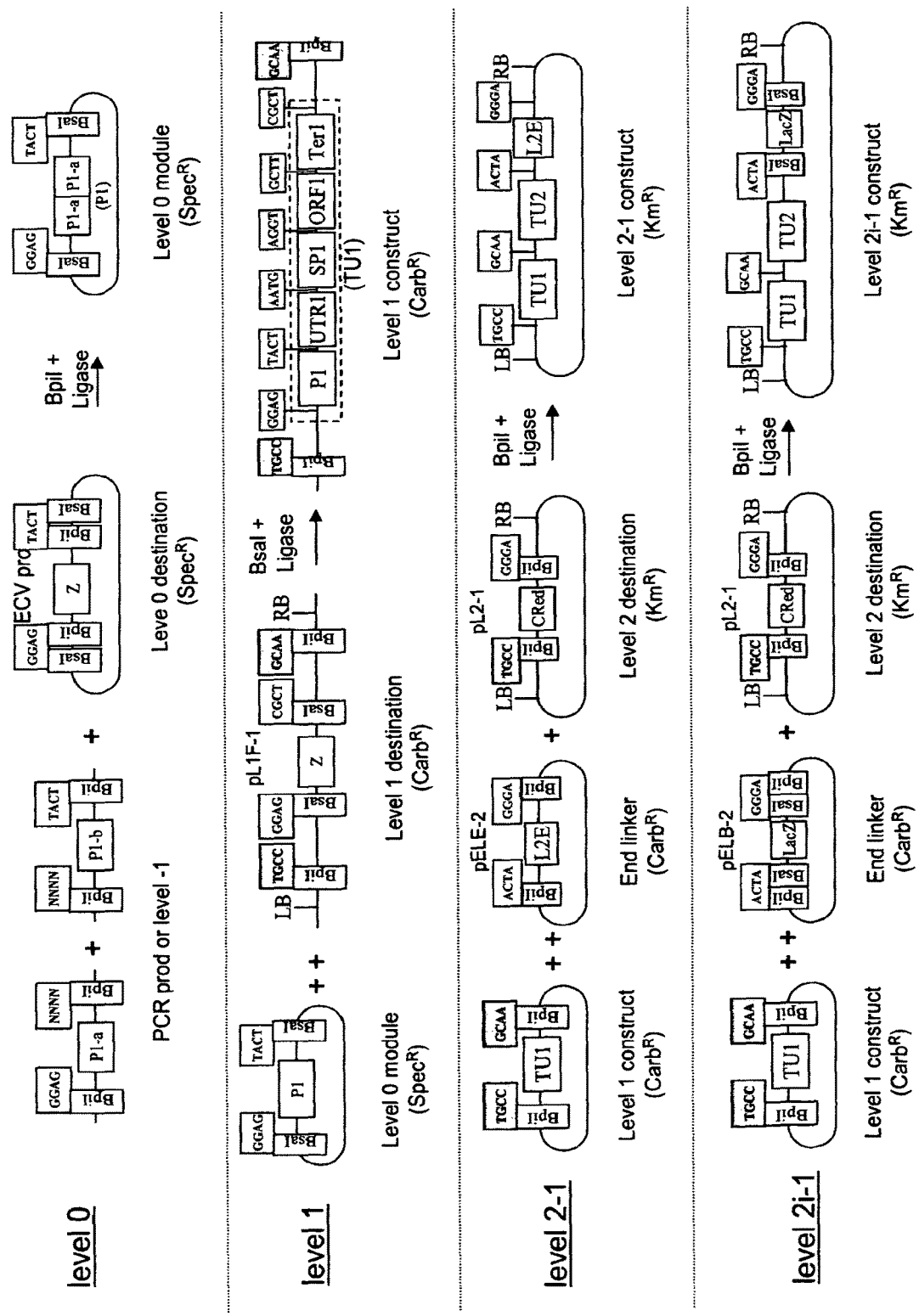
FIG. 5A illustrates the structure of the modules depicted in FIG. 3 in greater detail and shows how these modules can be assembled.

The second type of reactants of the level 1 reaction is one or more modules that can be incorporated into the entry DNAs in the level 1 reaction using the known methodology described in Engler et al. PLoS ONE 4 (2009) e5553. These modules are also referred to herein as "level 0 modules", since they can be produced in a level 0 reaction. An example of a level 1 reaction is schematically shown in FIG. 5A. One or more level 0 modules are ligated together in a desired order with and into the entry DNA to produce the level 1 fragment constructs (level 1 construct), using the inner pair of type IIs restriction sites present in sequence portion of item (ii) of the entry DNA. This leaves the recognition and cleavage sites of items (i) and (iii) unchanged, whereby these are also present in the reaction product for use in the subsequent level 2 reaction. Since at least 3 nucleic acid fragment constructs are employed in method of the invention, at least 3 level 1 reactions are typically performed separately. Multiple level 1 constructs and a level 2 destination vector are then combined in a one pot reaction on level 2.

In the method of the invention, a nucleic acid construct of interest is produced from at least m nucleic acid fragment constructs numbered 1 to m. Each nucleic acid construct of interest typically comprises a sequence segment to be incorporated into the nucleic acid construct of interest. These sequence segments may be numbered 1 to m as the nucleic acid fragment construct containing them in the order of occurrence in the nucleic acid construct of interest. Numeral m is an integer of at least 3, preferably at least 6, more preferably at least 10. Said method comprises the steps (A) to (C) as described in the following.

In step (A), the m nucleic acid fragment constructs are provided. Each of said m nucleic acid fragment constructs comprising in this order:

(i') a type IIs restriction endonuclease recognition site of the upstream cleavage site of item (ii');

(ii') a sequence segment of said nucleic acid construct of interest, said sequence segment comprising an upstream cleavage site of the recognition site of item (i'), a core portion of the sequence segment, and a downstream cleavage site of the recognition site of the following item (iii'), and (iii') the type IIs restriction endonuclease recognition site of said downstream cleavage site of item (ii').

Figure 7:
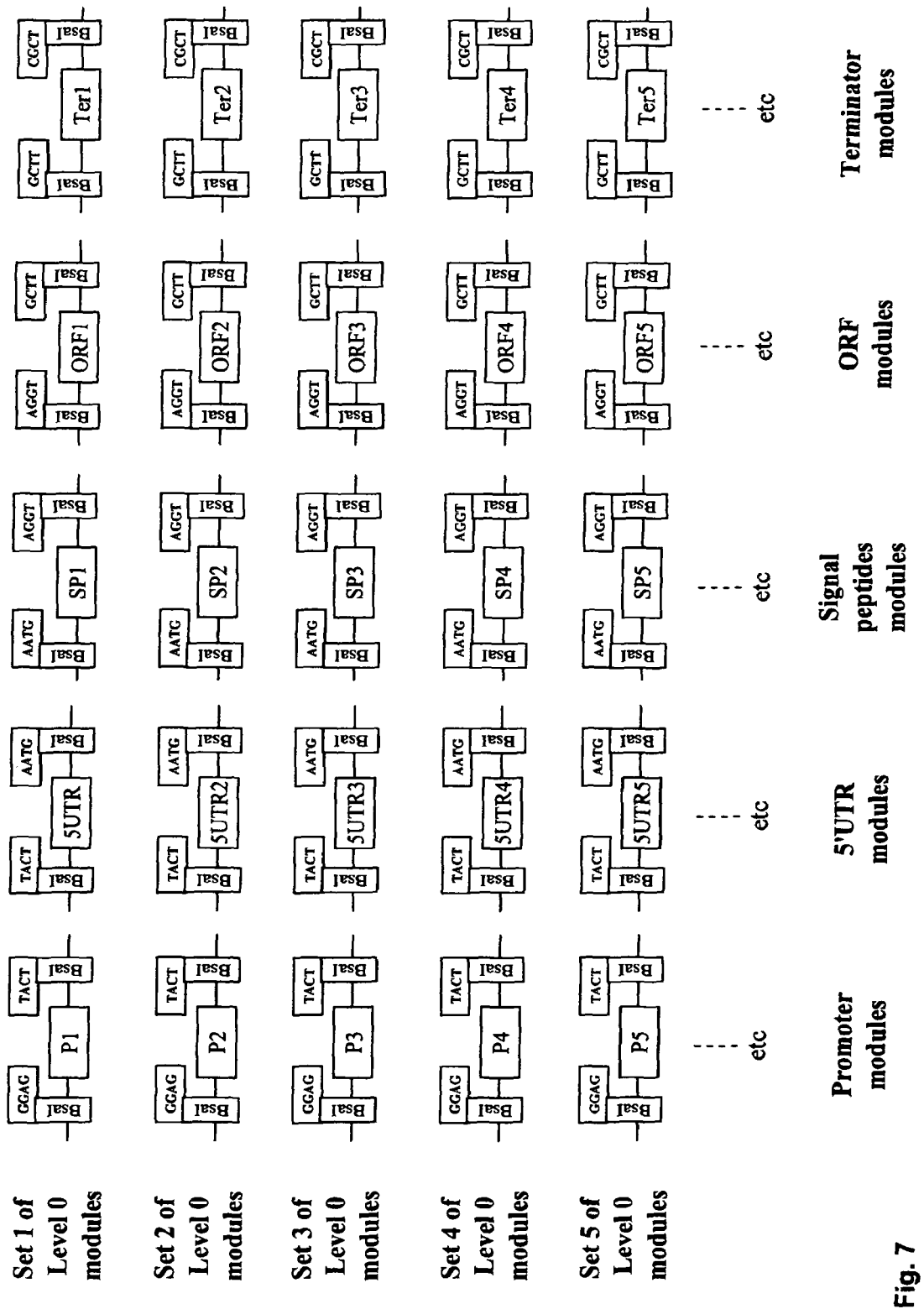
FIG. 7 shows the structure of level 0 modules.

The m nucleic acid fragment constructs can be provided in (separate) level 1 reactions using the entry DNAs of the system of the invention and at least one module per type of fragment construct that provides the core portion to the sequence segment of item (ii'). In the level 1 reaction one or several such modules may be combined to generate the fragment constructs with the desired core portion comprising portions derived from multiple modules. The modules used in the level 1 reaction are also referred to herein as "level 0 modules", as they can be prepared in a restriction and ligation step before the level 1 reaction. The level 1 reaction may be performed as explained with reference to FIGS. 7 and 8 using known methods and as described herein. It is also possible to use more than module having identical type IIs restriction endonuclease cleavage sites in one restriction and ligation reaction, allowing the generation of libraries of nucleic acid fragment constructs. For example, five promoter modules P1 to P5 as depicted in FIG. 7 may be combined in one reaction, whereby a mixture of level 1 fragment constructs is obtained that differ by having different promoters. Thus, the mixture of fragment constructs may be screened for the most suitable promoter function in the context of the remaining modules introduced into the fragment constructs. Similarly, libraries of fragment constructs containing different 5'UTRs, signal peptides, ORFs, terminators, combinations thereof or other elements may be produced and screened for a suitable property using the invention.

The downstream cleavage sites of nucleic acid fragment constructs 1 to m−1 are complementary to the upstream cleavage sites of nucleic acid fragment constructs 2 to m, respectively, for allowing assembly of the nucleic acid fragment constructs in the order corresponding to the numbering of the constructs in the subsequent step (B). In the nucleic acid fragment constructs, the recognition sites of items (i') and (iii') as well as the upstream and downstream cleavage sites of item (ii') are derived from the entry DNAs used, whereas the core portion is essentially derived from the level 0 modules.

If the nucleic acid fragment constructs are provided in a level 1 reaction, the products of the level 1 reaction are generally transformed into cells for amplification and purification. Typically, they are transformed into competent bacterial cells such as *E. coli* cells. After cell growth, the fragment constructs are isolated from the cells, e.g. using standard plasmid preparation protocols, for use in the following step (B).

The method of the invention comprises two steps wherein fragment constructs are combined, namely the following steps (B) and (C). In these steps, at least one fragment construct is used in step (C) that is derived from the same entry DNA as a fragment construct used in step (B). Thus, the method of the invention allows reuse of entry DNAs for more than one nucleic acid fragment. It is an important aspect of the invention that many different fragment constructs can be combined with a relatively small number entry DNAs. However, in this embodiment, fragment constructs derived from the same entry DNA have the same upstream and downstream cleavage sites (ii') and are therefore used in separate reactions to avoid statistical inclusion of either fragment construct at a selected position into the final nucleic acid construct of interest.

For this purpose, the downstream cleavage site of a nucleic acid fragment construct u, wherein u is an integer that is <m and at least 2, is complementary to the upstream cleavage site of the type IIs restriction endonuclease recognition site of item (ii') of nucleic acid fragment 1 (illustrated in FIG. 4 by the long dashed arrow linking cleavage sites TGCC of pL1F-1 and pL1F-7).

Step (B) is a level 2 reaction. In the terminology used with reference to the figures, step (B) is a level 2i-1 reaction. In step (B), the sequence segment(s) of item (ii') of nucleic acid fragment constructs 1 to s, wherein s is an integer <u, and said linker are ligated, in this order, and inserted into said destination vector. This may be done by reacting, in the presence of a type IIs restriction endonuclease recognising said type IIs restriction endonuclease recognition sites of items (i') and (iii') and items (I) and (III) of the destination vector defined below and in the presence a DNA ligase, in reaction medium compatible with activity of said type IIs restriction endonuclease and said ligase. For example, a mixture comprising nucleic acid fragment constructs 1 to s, the destination vector and a linker may be treated with the type IIs restriction endonuclease and the DNA ligase in a reaction medium compatible with activity of the type IIs restriction endonuclease and the ligase. Thus, s defines the number of nucleic acid fragment constructs combined in step (B) with the (level 2) destination vector. Since s is smaller than u, nucleic acid fragment construct u+1 and higher will not be used in step (B), but in a subsequent step such as step (C).

The linker that may be used in step (B) is as defined above. Cleavage site (b) of the linker may be complementary to the downstream cleavage site of item (ii') of nucleic acid fragment construct s, and cleavage site (g) of said linker and the cleavage site of item (III) of the destination vector may complementary for connecting the downstream cleavage site of fragment construct s to site (III) of the destination vector.

Step (B) may comprise transformation of the restriction and ligation product into cells for amplification and purification. Typically, it is transformed into competent bacterial cells such as E. coli cells. After cell growth, the level 2 construct is generally isolated from the cells, e.g. using standard plasmid preparation protocols, for use in the following step (C).

Figure 6:
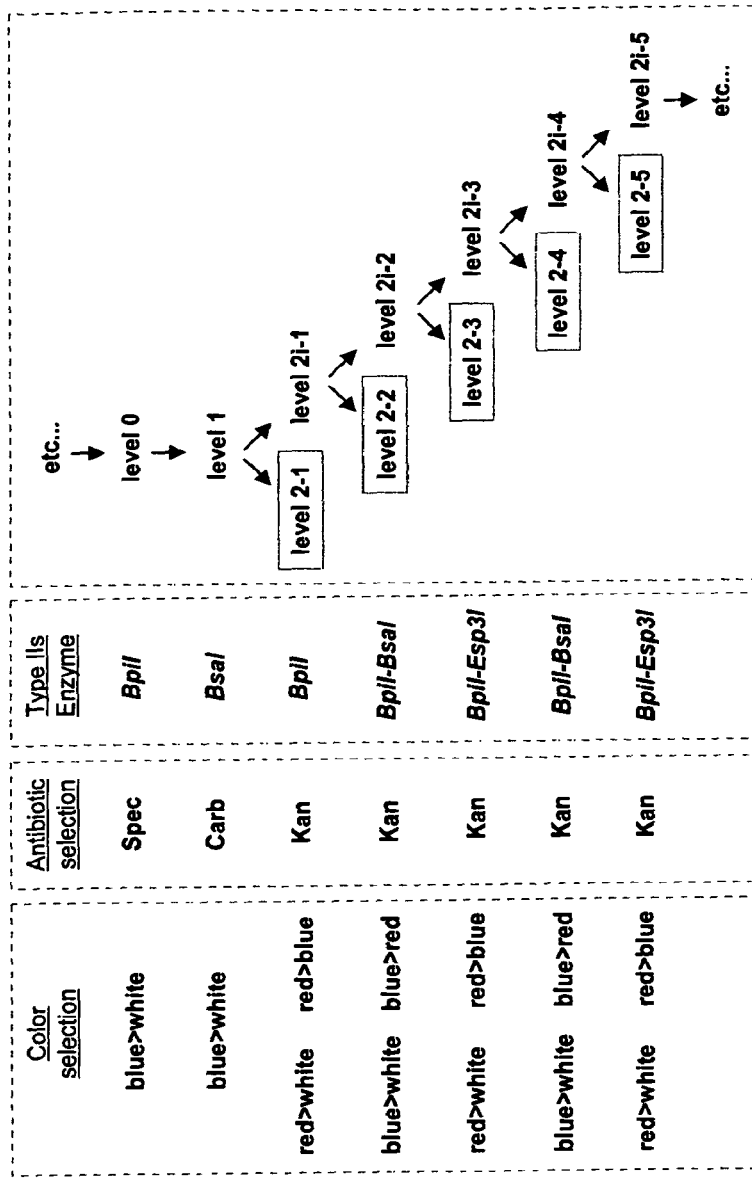
FIG. 6 is an overview of alternative cloning strategies.

Step (C) is a subsequent level 2 reaction. In the terminology used with reference to the figures, step (C) is a level 2-2 or level 2i-2 reaction. In step (C), a mixture comprising the recombination product of step (B) (a "level 2i-1 construct") and nucleic acid fragment construct(s) s+1 to m is treated with a type IIs restriction endonuclease recognising said type IIs restriction endonuclease recognition sites of items (i') and (iii'), a type IIs restriction endonuclease recognising said type IIs restriction endonuclease recognition sites of items (d) and (e) of the linker and a DNA ligase in a reaction medium compatible with activity of said type IIs restriction endonucleases and said ligase. Thereby, the sequence segments of item (ii') of nucleic acid fragment constructs s+1 to m and optionally a further linker as defined in item (3) are inserted into the cleavage sites provided by items (c) and (f) of the linker used in step (B). The recognition sites of items (i') and (iii') may be the same as the recognition sites of items (d) and (e) of the linker, whereby a type IIs restriction endonuclease recognising all these recognition sites can be used. The linker may be of the type pELE shown in FIG. 4, whereby no further level 2 reaction can be performed with the reaction product of step (C). Alternatively, a linker as defined in item (3) may be used, whereby a further level 2 reaction can be conducted. Thus, nucleic acid constructs of interest can be made from more than m nucleic acid fragment constructs. The possibility to use one or more further level 2 reactions is schematically shown in FIG. 6.

Step (C) may comprise transformation of the restriction and ligation product into cells for amplification and purification. Typically, it is transformed into competent bacterial cells such as E. coli cells. After cell growth, the construct of step (C) may be isolated from the cells, e.g. using standard plasmid preparation protocols.

The present invention provides a further system for producing a nucleic acid construct of interest. Similar as with the system described above, consecutive repetitions of cloning steps and re-use of the cleavage sites from a predefined set of vectors allows to increase the number of fragments that make up a nucleic acid construct of interest in a vector. In this system, a set of n destination vectors is used that are referred to as "level M destination vectors". Level M destination vectors differ from level 2 destination vectors in that an additional type IIs restriction endonuclease recognition site is present (compare the level 2 destination vectors of FIG. 4 with the "level M destination vectors" in FIG. 31). The additional recognition site has a cleavage site of the same nucleotide sequence as the cleavage site of item (I) of the level 2 destination vectors. Fragment constructs or entry DNAs are inserted into the level M destination vectors together with linkers referred to as "linkers M". Linkers M differ from linkers such as linkers pELE shown in FIG. 4 in that they have an additional type IIs restriction endonuclease recognition site (compare linkers pELE of FIG. 4 with the "end liners M" in FIG. 31). The additional recognition site of linkers M has a cleavage site of the same nucleotide sequence as the cleavage site on the left hand side of linkers pELE of FIG. 4. The additional recognition sites of destination vectors M and linkers M allow excision of constructs cloned into the designation vectors M and introduction, preferably with other constructs produced in parallel level M reactions, into a further destination vector referred to as "level P destination vector" together with a suitable linker referred to as linker P. Similarly as destination vectors M and linkers M, destination vectors P and linkers P are designed such that excision of constructs cloned into the designation vectors P is possible as well as reintroduction into a further level M destination vector. Since in each cloning step, multiple fragment constructs prepared in parallel preceding steps can be combined, the number of fragment constructs combined into a construct of interest can be increased multiplicatively, which is indicated by letter M in "destination vector M". In any event, a set of n destination vectors M and a set of n linkers M, preferably in combination with a set of n destination vectors P and set of n linkers P, allows reuse of a limited number of n cleavage sites such that a large number of fragment constructs (90 in FIG. 36) can be assembled with a small number of elements n in said sets.

n is at least 2, preferably at least 3, more preferably at least 4. The versatility of the system increases with increasing n. However, it is not necessary to have n>10. Thus, n may be a number of from 3 to 20, preferably of from 4 to 10, more preferably of from 5 to 9 or from 6 to 8. In the figures, embodiments with n=7 are exemplified, which is the most preferred embodiment.

The cleavage sites of items (II') and (III') of destination vectors M may overlap completely. In this case, one physical sequence of nucleotides provides the cleavage sites of two different type IIs restriction endonuclease recognition sites. Analogously, one physical sequence of nucleotides may provide the cleavage sites of two different type IIs restriction endonuclease recognition sites, namely the cleavage sites of items (b') and (c'), of items (II') and (III') and of items (b") and (c"). This embodiment is used in the examples shown in the figures. However, it is also possible that the cleavage sites of the pairs mentioned before are adjacent separated cleavage sites.

The number of entry DNAs to be used in not decisive in the system of this embodiment. It is possible that one entry DNA is incorporated into a level M destination vector, optionally followed by incorporation of one level 1 construct into a level P destination vector. However, the main advantages of the system can be made use of if at least 2, at least 3, at least 4, or at least 5 entry DNAs are combined by introduction into a destination vector M. The recognition sites of items (i), (iii), (I') and (VII'), (a'), and (f') may be recognition sites of the same type IIs restriction endonuclease.

Figure 32A:
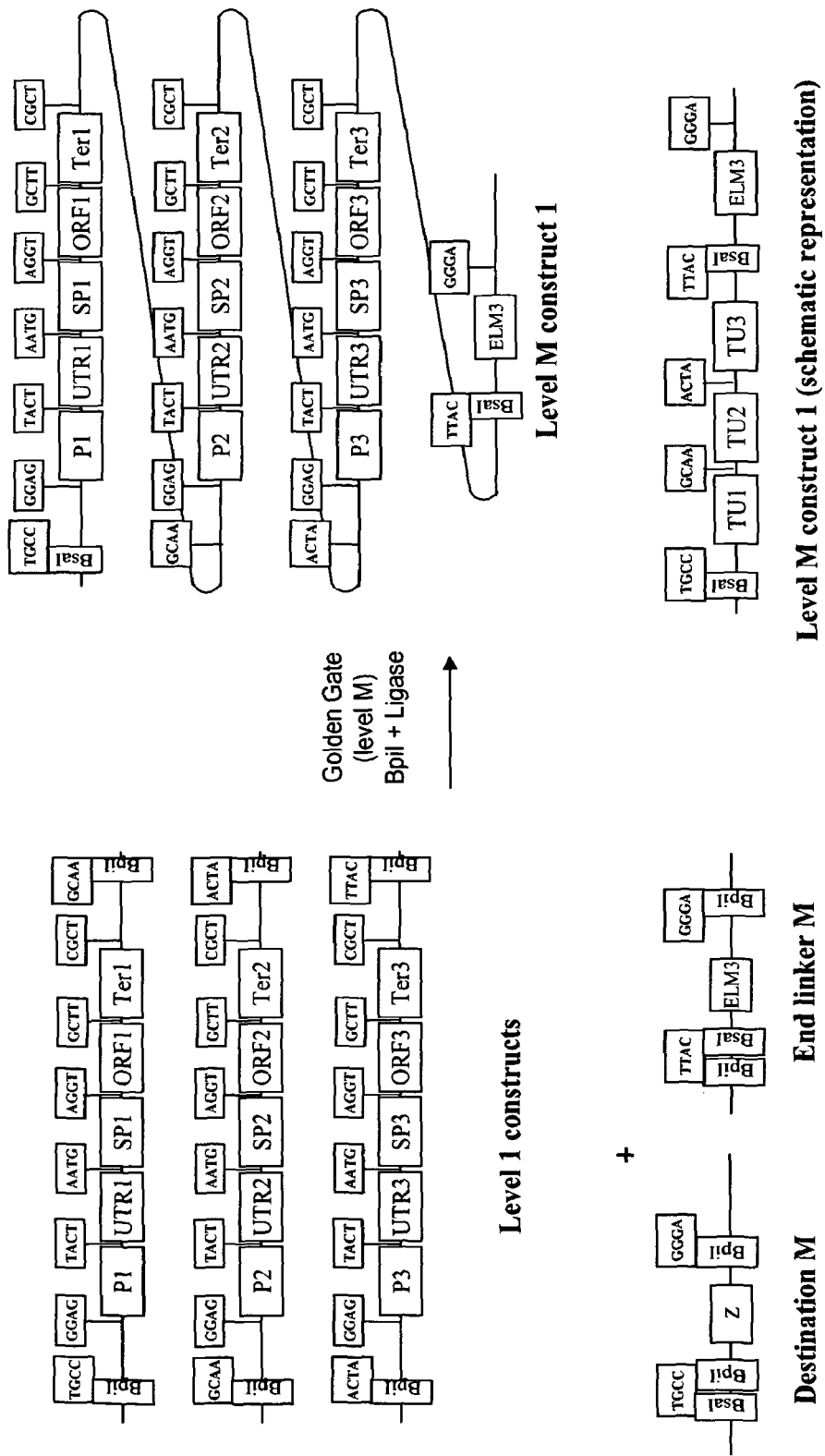
FIGS. 32A-C show an example where blocks of three (FIG. 32A) and two (FIG. 32B) transcription units are separately pre-assembled into level M destination vectors before being assembled in a level 2 vector in a subsequent step (FIG. 32C).
Figure 34A:
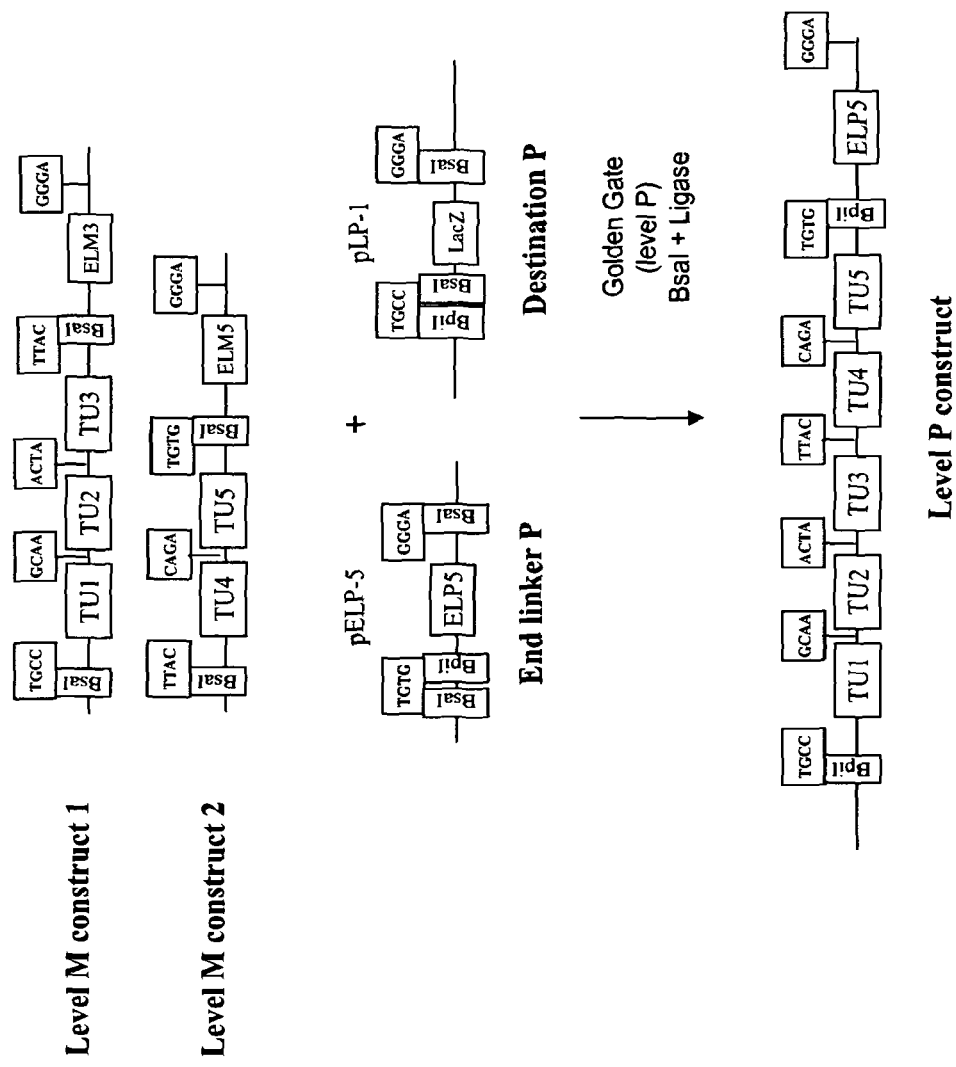
FIG. 34A illustrates a level P reaction wherein two level M constructs are assembled into a level P destination vector using an end-linker P to give a level P construct.

Multiple level M reactions can be conducted in parallel in separate reaction vessels as indicated in FIGS. 32a and b. The separate level M constructs may be combined in a subsequent level 2 or level P reaction. The destination vector M used in the second level M reaction is selected such that it has a complementary cleavage site to the cleavage site provided by the linker M used in the first level M reaction. In this way, two or more level M constructs can be combined in a level 2 reaction (FIG. 32c) or a level P reaction (FIG. 34a). In FIG. 32c, it is the TTAC cleavage site in the level M construct 1 that is derived from a linker M used in a first level M reaction. The TTAC cleavage site in the level M construct 2 is derived from a destination vector M used in the second level M reaction. Cleavage by BsaI allows ligation of the construct comprising TU1 to TU3 with the construct comprising TU4 and TU5 into the destination vector level 2. Alternatively, as shown in FIG. 34a, a destination vector P and linker P can be treated with BsaI and ligase together with level M constructs 1 and 2 to give the level P construct shown at the bottom of FIG. 34a.

Figure 34B:
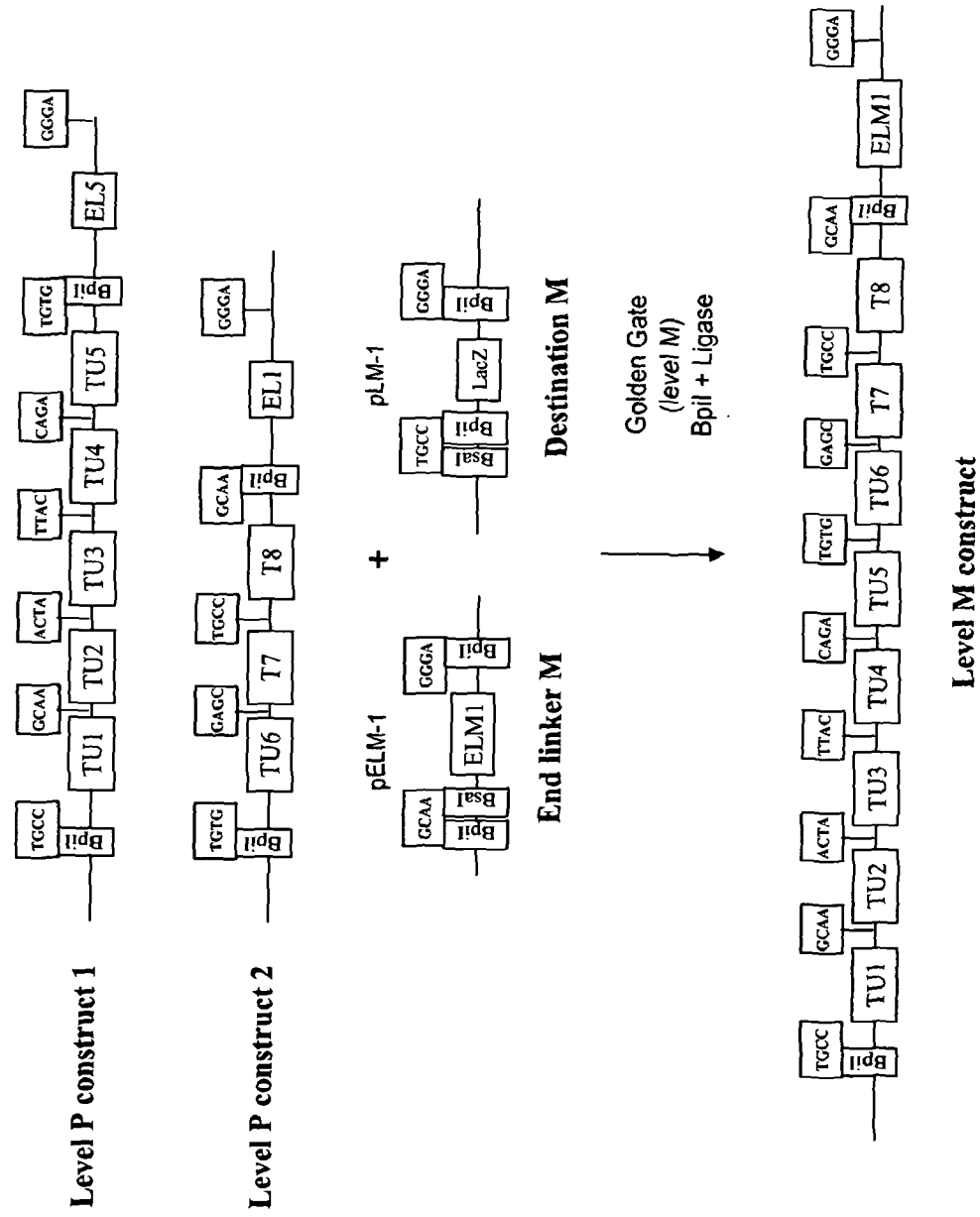
FIG. 34B illustrates a level M reaction wherein two level P constructs are assembled into a destination vector M ("destination M") using an end-linker M to give a Level M construct.

In the set of n destination vectors P, the same set of cleavage sites is used as in the destination vectors M. The cleavage sites (VI") of all n destination vectors P are identical and are at the same time identical to the cleavage sites of items (VI') of destination vectors M. In the set of n linkers P, the same set of cleavage sites is used as in the linkers M and the destination vectors M. Thus, a limited set of n cleavage sites allows to combine a number of fragments constructs that can far exceed the number of n. As shown in FIG. 34b, multiple level P constructs can be combined into another destination vector M using a linker M.

The recognition sites of items (I"), (IV'), (d'), (a") and (f') may be recognition sites of the same type IIs restriction endonuclease, and the recognition sites of items (IV"), (I'), (VII'), (a') and (f') may be recognition sites of the same type IIs restriction endonuclease.

Item (VIII') of destination vector M may have a marker allowing selection of ligation product of a level M reaction for absence of item (VIII'). The marker may be lacZ for blue/white selection. Item (VIII") of destination vector P may have a marker allowing selection of ligation product of a level P reaction for absence of item (VIII"). Generally, the designation vectors and the linkers are circular molecules or plasmids containing a selectable marker in their backbone.

An advantage of systems and methods of the invention is that cloning steps can be done as one-pot reactions, requiring only a simple incubation such as in a thermocycler. In particular, this avoids the need for labor-intensive and operations that are difficult to automate such as purification of DNA fragments from agarose gels. This mean that all the elements required for the design of a completely automatized cloning system are now in place. Operations that are employed are preparation of miniprep DNA, liquid handling and incubation to perform restriction-ligation, plating of transformations on plates, picking of colonies, and digestion and analysis of miniprep DNA. This last step may be replaced by DNA sequencing, as very few colonies need to be screened to obtain the desired construct (in the majority of cases, one colony is sufficient). All these operations can easily be handled by standard automation robots. This aspect promises to revolutionize the number of constructs that can be made within a given time as well as the production costs for these constructs, and therefore opens the door for new applications that will be required in the field of synthetic biology.

Another advantage of the invention compared to more traditional cloning strategies is that complex design of specific construction strategies is not needed anymore, since the design is automatically defined by the number and the order of modules (or genes) that a user wants to assemble. The cloning strategy in fact can be easily and unambiguously determined by a simple computer program. This program can be directly linked to the automation robots that would physically make the construct. An advantage of such system is that the cloning strategy itself cannot become a limiting factor when constructs reach a large size, since the same principles and the same cloning vectors can be reused indefinitely. In fact, it is conceivable that the invention can be used to clone entire chromosomes.

DETAILED DESCRIPTION OF THE INVENTION

The system of the invention allows the production of nucleic acid constructs of interest from multiple nucleic acid fragments constructs using a combination of nucleic acid fragment constructs via single-stranded overhangs formed at both ends of the fragments using type IIs restriction endonucleases. In the invention, type IIs restriction enzymes are used. The type IIs restriction endonuclease recognition site is a recognition site of a restriction endonuclease recognizing a double-stranded DNA and cleaving the double-stranded DNA at a cleavage site that is outside the recognition site on the double stranded DNA. The type IIs restriction endonuclease cleaves such that, depending on the specific type IIs restriction endonuclease, overhangs of from 3 to 6 nucleotides are produced. However, it is also possible to use type IIs endonucleases producing longer single-stranded overhangs. The nucleotide range that forms the overhangs upon cleavage is referred to herein as cleavage site. Since the nucleotides of the cleavage site are not part of the recognition site, they can be chosen as desired without destroying cleavage activity of the type IIs restriction endonuclease. Examples of type IIs restriction endonucleases suitable for the methods of the invention are given below.

For practicing the invention, not only BsaI and BpiI, but any type IIs restriction enzyme that provides "sticky" ends sufficient for efficient ligation at its cleavage sites can be used. A selection of such enzymes is provided on the REBASE webpage (rebase.neb.com/cgi-bin/asymmlist) and in the review of Szybalsky et al. (1991, Gene, 100:13-26). Type II restriction enzymes with asymmetric recognition sites (e.g. those shown in this webpage) that have cleavage site outside of recognition site and provide upon cleavage of at least three, preferably 4 or more nucleotide residues overhangs (e.g. Bli736I; BpuAI, VpaK321, SfaNI, etc.) can be used in the invention. It is recommended that the recognition site contains at least 4, more preferably at least 6 or more base pairs in order to minimize the chance for such site to be found in a sequence portion of interest. Type IIs restriction nucleases with 5 bp recognition sites (e.g. SfaNI) also can be used. Type IIs restriction endonucleases that produce 4 nt single-stranded overhangs at the extremities of digested fragments can theoretically generate ends with 256 possible sequences. Type IIs restriction enzymes having even longer recognition sites, e.g. comprising ten or more base pairs have been engineered. The largest recognition site among natural type IIs enzymes is for the enzyme SapI which has a 7 bp recognition site. A preferred solution is the use of artificial type IIs enzymes engineered to have a long recognition site (Lippow et al, 2009, Nucleic acids Res., 37:3061-3073). For example, a type IIs enzyme with a 18 bp recognition sites would be expected to cut only a few times per eukaryotic genome at most, and would allow to make most entry modules without having to change any nucleotide of the native sequence.

TABLE 1

List of usable type IIs restriction enzymes commercially available

| Name | Recognition sequence | reach top strand | reach bottom strand | extension |
| --- | --- | --- | --- | --- |
| BsaXI | (9/12) ACNNNNNCTCC (10/7) | 10 | 7 | 3 nt 3' |
| Bst6I | CTCTTC (1/4) | 1 | 4 | 3 nt 5' |
| Eam1104I | CTCTTC (1/4) | 1 | 4 | 3 nt 5' |
| EarI | CTCTTC (1/4) | 1 | 4 | 3 nt 5' |
| LguI | GCTCTTC (1/4) | 1 | 4 | 3 nt 5' |
| PciSI | GCTCTTC (1/4) | 1 | 4 | 3 nt 5' |
| BspQI | GCTCTTC (1/4) | 1 | 4 | 3 nt 5' |
| SapI | GCTCTTC (1/4) | 1 | 4 | 3 nt 5' |
| BveI | ACCTGC (4/8) | 4 | 8 | 4 nt 5' |
| Acc36I | ACCTGC (4/8) | 4 | 8 | 4 nt 5' |
| BfuAI | ACCTGC (4/8) | 4 | 8 | 4 nt 5' |
| BspMI | ACCTGC (4/8) | 4 | 8 | 4 nt 5' |
| AarI | CACCTGC (4/8) | 4 | 8 | 4 nt 5' |
| Esp3I | CGTCTC (1/5) | 1 | 5 | 4 nt 5' |
| BsmBI | CGTCTC (1/5) | 1 | 5 | 4 nt 5' |
| BstV2I | GAAGAC (2/6) | 2 | 6 | 4 nt 5' |
| BpiI | GAAGAC (2/6) | 2 | 6 | 4 nt 5' |
| BpuAI | GAAGAC (2/6) | 2 | 6 | 4 nt 5' |
| BbsI | GAAGAC (2/6) | 2 | 6 | 4 nt 5' |
| BseXI | GCAGC (8/12) | 8 | 12 | 4 nt 5' |
| Lsp1109I | GCAGC (8/12) | 8 | 12 | 4 nt 5' |
| BstV1I | GCAGC (8/12) | 8 | 12 | 4 nt 5' |
| BbvI | GCAGC (8/12) | 8 | 12 | 4 nt 5' |
| SfaNI | GCATC (5/9) | 5 | 9 | 4 nt 5' |
| LweI | GCATC (5/9) | 5 | 9 | 4 nt 5' |
| BtgZI | GCGATG (10/14) | 10 | 14 | 4 nt 5' |

TABLE 1-continued

List of usable type IIs restriction enzymes commercially available

| Name | Recognition sequence | reach top strand | reach bottom strand | extension |
|---|---|---|---|---|
| FokI | GGATG (9/13) | 9 | 13 | 4 nt 5' |
| FaqI | GGGAC (10/14) | 10 | 14 | 4 nt 5' |
| BslFI | GGGAC (10/14) | 10 | 14 | 4 nt 5' |
| BsmFI | GGGAC (10/14) | 10 | 14 | 4 nt 5' |
| Bso31I | GGTCTC (1/5) | 1 | 5 | 4 nt 5' |
| BspTNI | GGTCTC (1/5) | 1 | 5 | 4 nt 5' |
| Eco31I | GGTCTC (1/5) | 1 | 5 | 4 nt 5' |
| BsaI | GGTCTC (1/5) | 1 | 5 | 4 nt 5' |
| Alw26I | GTCTC (1/5) | 1 | 5 | 4 nt 5' |
| BstMAI | GTCTC (1/5) | 1 | 5 | 4 nt 5' |
| BsmAI | GTCTC (1/5) | 1 | 5 | 4 nt 5' |
| BaeI | (10/15) ACNNNNGTAYC (12/7) | 12 | 7 | 5 nt 3' |
| PpiI | (7/12) GAACNNNNNCTC (13/8) | 13 | 8 | 5 nt 3' |
| PsrI | (7/12) GAACNNNNNNTAC (12/7) | 12 | 7 | 5 nt 3' |
| AloI | (7/12) GAACNNNNNNTCC (12/7) | 12 | 7 | 5 nt 3' |
| BarI | (7/12) GAAGNNNNNNTAC (12/7) | 12 | 7 | 5 nt 3' |
| AjuI | (7/12) GAANNNNNNNTTGG (11/6) | 11 | 6 | 5 nt 3' |
| TstI | (8/13) CACNNNNNNTCC (12/7) | 12 | 7 | 5 nt 3' |
| Hin4I | (8/13) GAYNNNNNVTC (13/8) | 13 | 8 | 5 nt 3' |
| HgaI | GACGC (5/10) | 5 | 10 | 5 nt 5' |
| CseI | GACGC (5/10) | 5 | 10 | 5 nt 5' |

TABLE 2

Preferred type IIs restriction enzymes

| Name | Recognition sequence | reach top strand | reach bottom strand | extension |
|---|---|---|---|---|
| LguI | GCTCTTC (1/4) | 1 | 4 | 3 nt 5' |
| PciSI | GCTCTTC (1/4) | 1 | 4 | 3 nt 5' |
| BspQI | GCTCTTC (1/4) | 1 | 4 | 3 nt 5' |
| SapI | GCTCTTC (1/4) | 1 | 4 | 3 nt 5' |
| BveI | ACCTGC (4/8) | 4 | 8 | 4 nt 5' |
| Acc36I | ACCTGC (4/8) | 4 | 8 | 4 nt 5' |
| BfuAI | ACCTGC (4/8) | 4 | 8 | 4 nt 5' |

TABLE 2-continued

Preferred type IIs restriction enzymes

| Name | Recognition sequence | reach top strand | reach bottom strand | extension |
|---|---|---|---|---|
| BspMI | ACCTGC (4/8) | 4 | 8 | 4 nt 5' |
| AarI | CACCTGC (4/8) | 4 | 8 | 4 nt 5' |
| Esp3I | CGTCTC (1/5) | 1 | 5 | 4 nt 5' |
| BsmBI | CGTCTC (1/5) | 1 | 5 | 4 nt 5' |
| BstV2I | GAAGAC (2/6) | 2 | 6 | 4 nt 5' |
| BpiI | GAAGAC (2/6) | 2 | 6 | 4 nt 5' |
| BpuAI | GAAGAC (2/6) | 2 | 6 | 4 nt 5' |
| BbsI | GAAGAC (2/6) | 2 | 6 | 4 nt 5' |
| BtgZI | GCGATG (10/14) | 10 | 14 | 4 nt 5' |
| Bso31I | GGTCTC (1/5) | 1 | 5 | 4 nt 5' |
| BspTNI | GGTCTC (1/5) | 1 | 5 | 4 nt 5' |
| Eco31I | GGTCTC (1/5) | 1 | 5 | 4 nt 5' |
| BsaI | GGTCTC (1/5) | 1 | 5 | 4 nt 5' |
| HgaI | GACGC (5/10) | 5 | 10 | 5 nt 5' |
| CseI | GACGC (5/10) | 5 | 10 | 5 nt 5' |

Most preferred are the following type IIs restriction endonucleases: SapI, BspMI, AarI, Esp3I, BpiI, BsaI and HgaI. Many of the cited restriction endonucleases are available from New England Biolabs. Sources of these enzymes can also be found on the REBASE webpage mentioned above.

Examples of ligases to be used in the invention include T4 DNA ligase, E. coli DNA ligase, Taq DNA ligase, all of which are commercially available from New England Biolabs.

In the following, the invention will be further described with reference to specific embodiments, examples and the figures.

FIG. 1A shows elements of a system that allows re-use of the entry DNAs of the invention (level 1 destination vectors) for different inserted sequence segments. This system comprises:
(1) n nucleic acid fragment constructs ("na", shown for n=1 to 7), each flanked by two sequences Sx and Sy representing cleavage sites of a type IIs restriction endonuclease. After restriction endonuclease digestion, the cleavage sites form single-stranded overhangs that are complementary from one nucleic acid fragment constructs (as well as the underlying entry vector) to the next, which is indicated by the same index of "S". The cleavage site at the 3' end (right hand side in the figures) of the last construct (na7) forms a single-stranded overhang compatible with the overhang created by cleavage of the cleavage site at the 5' end (left hand side in the figures) of the first fragment construct na1 by restriction endonuclease digestion, as indicated by the same numbering "S1" at these sites;
(2) a set of n 'end-linkers' (ELx, x indicating the numbering from 1 to 7) flanked on one side (5' end) with a cleavage site compatible with the 3' cleavage sites (S1 to S7) of the nucleic acid fragment constructs (as well as the underlying entry DNA) and on the other side (3' end) with a unique site not compatible with any of the n entry DNAs (S8);
(3) a destination vector with two cleavage sites, one site compatible with sites S1 (or S2, S3, S4, S5, S6, S7), and the other site compatible with cleavage site S8 of the end-linkers.

FIG. 1B provides an example for cloning of three nucleic acid fragment constructs into a destination vector. Cloning of the three nucleic acids fragment constructs employs ligation of the appropriate end-linker (end-linker 3). The resulting construct can be later re-opened at cleavage sites S4 and S8 by digestion with the appropriate type IIs endonuclease. All other sites lack a flanking type IIs endonuclease recognition site in the reaction product and are thus protected from digestion with the endonuclease used for the production of this reaction product.

FIG. 1C shows that further nucleic acid fragment constructs na4 to na7 and a further construct na1 that is based on the same entry vector number 1 as na1 ligated in FIG. 1B can be cloned into the product vector obtained in FIG. 1B. At each successive cloning step, a different end-linker is used (ELx or ELx-b that differ by containing different internal type IIs restriction site for reopening the construct at the next stage). The structure of the end-linkers will be more specifically explained in the following figures).

Figure 2:
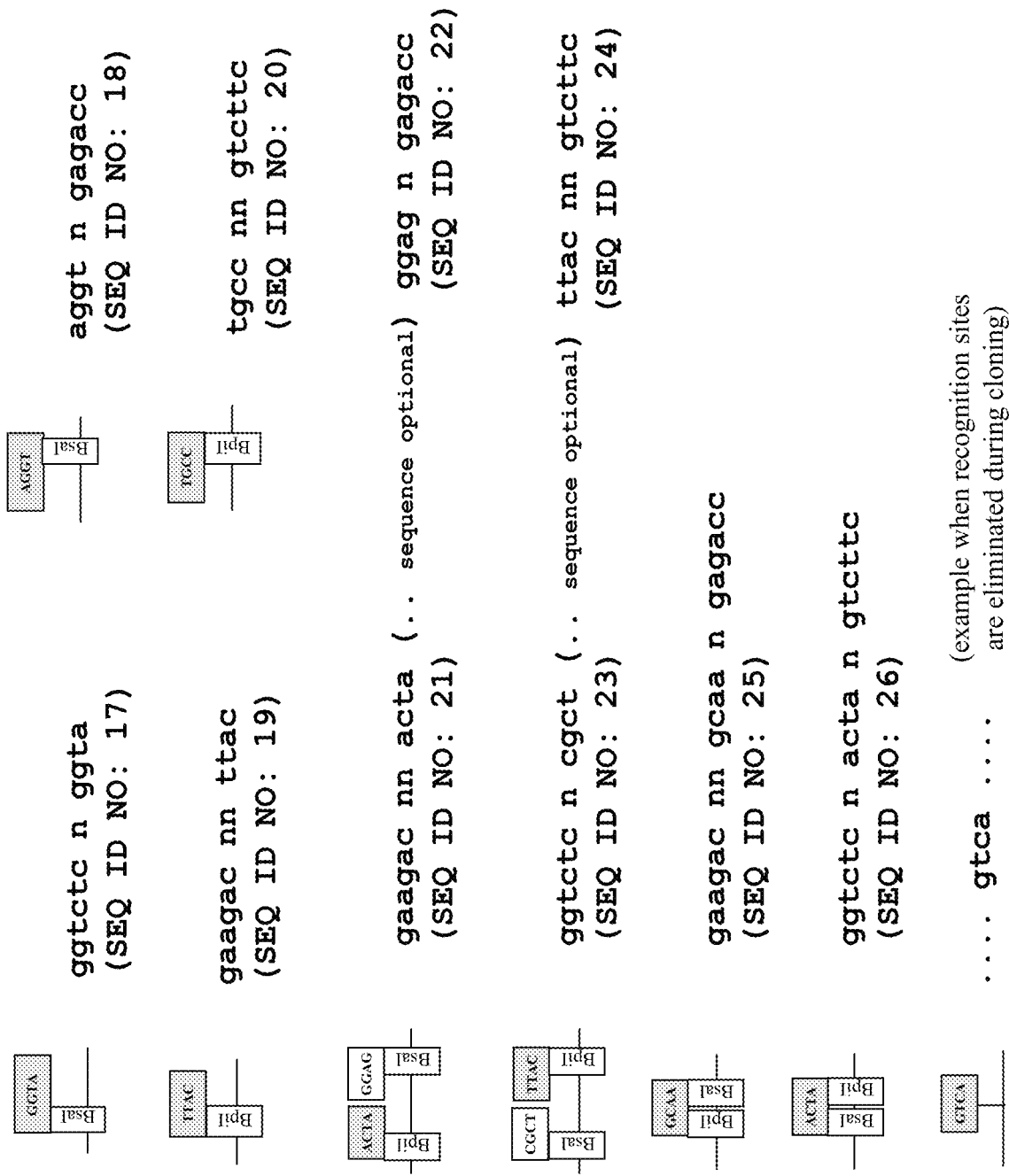
FIG. 2 explains how type IIs restriction sites are depicted in the following figures.

FIG. 2 explains how type IIs restriction sites are depicted in the following figures. A type IIs restriction endonuclease site contains a recognition sequence (also referred to herein as "recognition site") and a cleavage site located outside of the recognition sequence. The nucleotide sequence of the cleavage site is shown in a horizontally elongated box. The recognition site can be found on either side of the cleavage site, depending on the orientation of the asymmetrical recognition site in the DNA. When the recognition sequence is located on the left of the cleavage site, the recognition site is illustrated as a vertically elongated box on the left half under the box representing the cleavage site. When the recognition sequence is located on the right of the cleavage site, the recognition site is illustrated as a vertically extended box on the right half under the box representing the cleavage site. The nucleotide sequences of the top DNA strand are shown next to the represented type IIs restriction sites. In the third and fourth row, two restriction sites are shown the cleavage sites of which are oriented towards each other, but are non overlapping and separated by an "optional sequence". In the fifth and sixth row, two restriction sites are shown the cleavage site of which overlap over the entire range of 4 base pairs.

After cloning using a type IIs enzyme, the corresponding recognition site is usually eliminated during cloning. If recognition sites on both sides of the cleavage site are eliminated, only the sequence of the cleavage site (4 bases in the examples depicted) is left in the DNA as shown schematically at the bottom.

Figure 3:
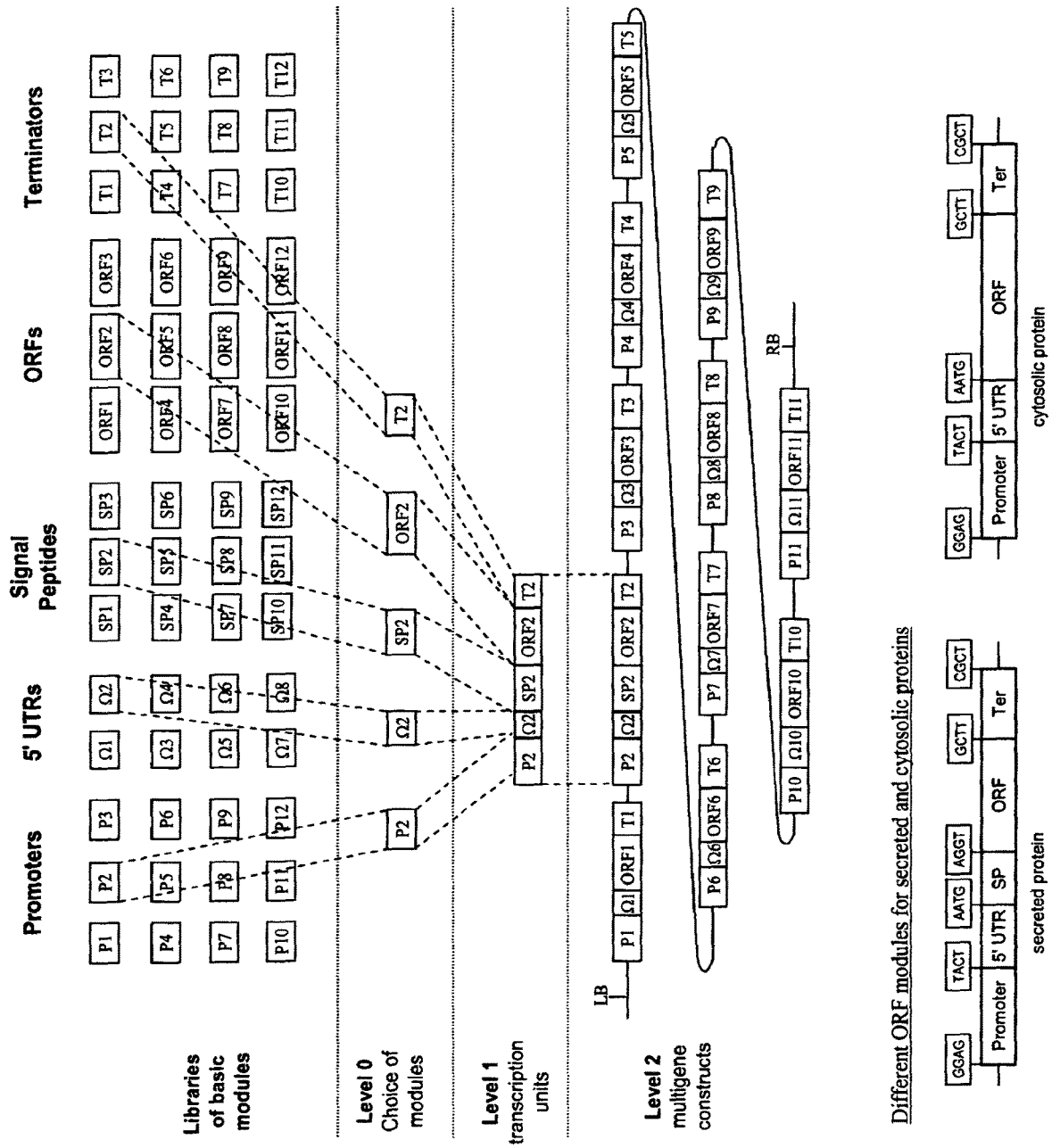
FIG. 3 shows a general embodiment wherein a eukaryotic multi-gene construct is produced as the nucleic acid fragment of interest.

FIG. 3 shows a general embodiment wherein a eukaryotic multi-gene construct is produced as the nucleic acid fragment of interest. FIG. 3 illustrates a general strategy that can be used. Basic genetic elements such as promoters, 5' untranslated regions (5' UTRs), signal peptides (SP), open reading frames (ORFs), and terminators (T) are cloned as basic modules ("level 0 modules"). Libraries of each of these types of genetic elements may be provided as shown at the top. The libraries of 'level 0' entry modules may be stored until needed for cloning. When a construct needs to be made, genetic elements cloned as level 0 modules are chosen (second row in the FIG. 3), and are assembled, in a level 1 reaction, using a one-pot Golden Gate cloning reaction into an entry DNA. The level 1 reaction product (schematically shown in the third row), referred herein as nucleic acid fragment construct, contains an assembled transcription unit comprising the chosen elements in the desired order. In a second step of cloning, two or more (11 in the depicted example) different transcription units (that can be made in separate level 1 reactions) are assembled in a desired order into a destination vector (level 2) to obtain a level 2 multigene construct of interest.

At the bottom, the basic gene structures for secreted and cytosolic proteins are shown. Since the latter have no signal peptide (SP), the ORF level 0 modules for cytosolic proteins may have the cleavage site sequences of the signal peptides used for secreted proteins for allowing linking of the ORF module with the 3' end of the module for the 5' UTR in the level 1 reaction.

FIG. 4 depicts a set of level 1 destination vectors, level 2 destination vectors, and end-linkers. The level 1 destination vectors and end-linkers are cloned in plasmids with a carbenicillin resistance selectable marker, while level 2 destination vectors carry a kanamycin resistance gene. Other antibiotic resistance genes could also be used instead of the ones used in this example. Level 1 destination vectors of the series pL1F-1 to -7 and of the series pL1R-1 to -7 differ by the cleavage sites of the internal pair type IIs restriction sites (the BsaI sites). The sites of both series are designed for cloning of the same assembled transcription units, but in opposite orientation. The level 1 destination vectors have an internal lacZ reporter gene that is removed together with the recognition sites of the internal pair of type IIs restriction sites (the BsaI sites) in the level 1 reaction due to the divergent orientation of these sites with respect to LacZ. Thus, lacZ is not present in the level 1 reaction product, allowing blue/while selection of cell clones containing the reaction product. The outer restriction sites in the level 1 destination vectors (the BpiI sites) are in convergent orientation with respect to the BsaI sites and lacZ and are unchanged in the level 1 reaction, since the restriction endonuclease of the inner pair of restriction sites (BsaI), but not the restriction endonuclease of the outer pair of restriction sites (BpiI), is used in the level 1 reaction. Straight dashed arrows indicate the complementarity of the cleavages sites of the right-hand BpiI sites of each of entry DNAs 1 to 6 with the left-hand entry DNA directly underneath which allows the ligation of entry DNAs 1 to 7, as well as the level 1 constructs derived therefrom, in the level 2 reaction via complementary single-stranded overhangs produced by BpiI digestion. Complementarity of the right-hand cleavage site of the bottom entry DNA (of sequence TGCC) with the left-hand cleavage site of the first entry DNA allows to reuse the entry DNA 1 and the following entry DNAs in a second level 2 reaction. In a second level 2 reaction, the reused entry DNAs may be provided in a level 1 reaction with a different insert compared to the insert (referred to as "core portion of the sequence segment" in item (ii') of the method of the invention). Thus, more nucleic acid fragment constructs can be combined into a nucleic acid construct of interest than the number of elements of the set of entry DNAs. "Divergent" herein means that the two cleavage sites of a pair of restriction sites are more remote than the recognition sites from a position between the two restriction sites. "Convergent" herein means that the two recognition sites of a pair of restriction sites are more remote than the cleavages sites from a position between the two restriction sites.

The set of level 2 destination vectors shown has the same number of elements as the number of level 1 destination vectors. The level 2 destination vectors have a pair of divergent (with respect to the central portion in which nucleic acid fragment constructs are inserted in the level 2 reaction) type IIs restriction sites flanking genes ("CRed") providing a red phenotype. For each upstream BpiI cleavage site of the entry DNAs there is a level 2 destination vector having a complementary upstream BpiI site. Thus, each entry DNA can be used to produce a nucleic acid fragment construct that will take position 1 in the level 2 reaction product.

Three sets of end-linkers are depicted, each set generally having the same number of elements as the number of level 1 and level 2 destination vectors. Sets pELB and pELR are similar in that they have the same cleavage sites and outer recognition sites. Sets pELB and pELR both have a further inner recognition site that will be unchanged in the level 2 reaction, whereby they are present in the level 2 reaction product. Thus, they can be used for inserting, in a second or further level 2 reaction, further nucleic acid fragment constructs into the reaction product of the first level 2 reaction. This is not possible if an end-linker from the pELE set is used, since these lack the inner divergent pair of restriction sites. Sets pELB and pELR differ in that different inner recognition sites (BsaI versus Esp3I) are used and in that different central reporter genes for color selection of cell clones are used. All end-linkers can be used for joining the nucleic acid fragment constructs derived from the level 1 destination vectors to the downstream cleavage site of the level 2 destination vectors using cleavage site GGGA. Thus all destination vectors and all end-linkers have the same downstream cleavage site (GGGA). For each downstream BpiI cleavage site of the entry DNAs there is a linker having a complementary upstream BpiI cleavage site.

FIG. 5A illustrates the structure of the modules depicted in FIG. 3 in greater detail and shows how these modules can be assembled. At each cloning step, constructs can be assembled by mixing in one tube all constructs or DNA fragments required, together with the appropriate type IIS enzyme (indicated above the horizontal reaction arrows) and ligase, and incubating the mix under conditions allowing restriction enzyme digestion and ligation.

Level 0 modules have an insert of interest (for example a promoter sequence, P1) located between two convergent type IIs restriction sites (BsaI in the example shown). Level 0 modules can be cloned by a number of different procedures, and one example is shown here, starting from either PCR products or level-1 constructs (top row of the figure designated "level 0"). In this example, cloning is performed using the enzyme BpiI in a compatible level 0 destination vector. Methods for such cloning are known from the literature, see e.g. Engler et al. PLoS ONE 4 (2009) e5553.

Compatible sets of level 0 modules are then assembled and cloned on level 1 into a level 1 destination vector using a Golden Gate cloning reaction with a second type IIs enzyme, here BsaI. The resulting level 1 constructs contain, for example, assembled transcriptional units (TUs).

Several level 1 constructs (in the present example, 2 such constructs indicated by "TU1" and "TU2") are then assembled together with a selected end-linker (pELE-2, see FIG. 4) in a compatible level 2 destination vector (pL2-1 for example). As discussed for FIG. 1a, both level 1 constructs have to be compatible for level 2 assembly, i.e. having convergent terminal cleavage sites. The first level 1 construct corresponds to position 1 (the level 0 modules were cloned in the level 1 destination vector pL1F-1 depicted in FIG. 4) and the second one corresponds to the next position (position 2), the level 0 modules of which were cloned in the level 1 destination vector pL1F-2). Since pELE-2 does not contain internal type IIs restriction sites, no further nucleic acids can be cloned in the resulting level 2 construct. In such case, the level reaction is referred to as "level 2-1" and the reaction product is referred to as "level 2-1 construct").

A similar level 2 reaction can however be made using end-linker pELB-2 rather than pELE-2 (see FIG. 4). Since this end-linker contains a pair of further internal type IIs restriction sites (BsaI), the resulting construct ("level 2i-1 construct") will also contain such site, and therefore can be used again as level 2 destination vector for a second level 2 reaction for insertion of additional transcriptional units or other fragment constructs.

++ indicates that only one of several entry clones was drawn due to space limitation. Each cleavage site is shown as a box with the 4 nucleotides of the cleavage site; the two boxes below show which type IIS recognition sites flank the recombination sites on the left and right sides. P1-a/b stands for promoter fragment 1 or 2; UTR1 stands for 5' untranslated sequence; T1 indicates a terminator; CRed stands for a red color visual marker encoding canthaxanthin biosynthetic genes.

Figure 5B:
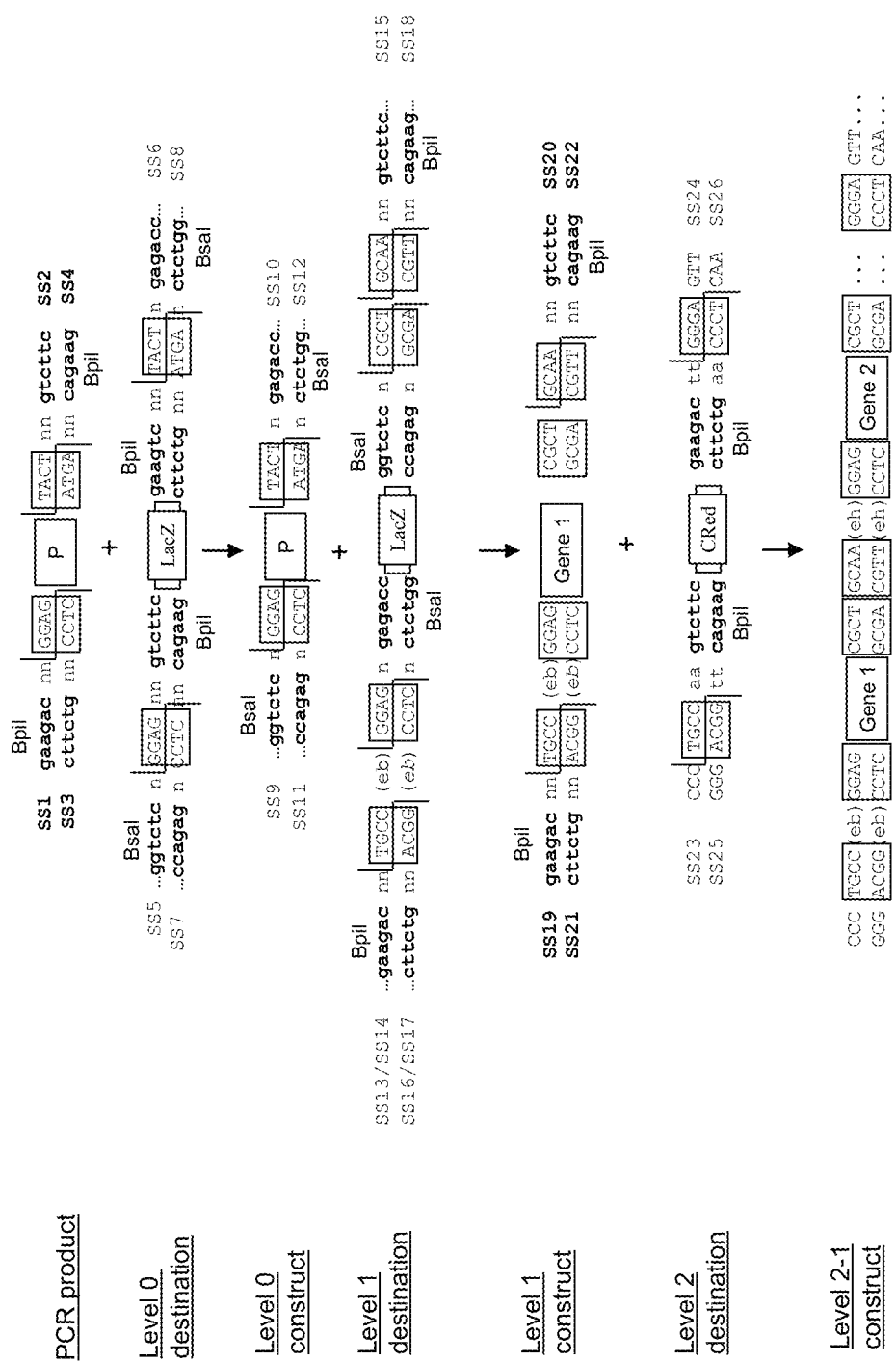
FIG. 5B show nucleotide sequences at the junction of various modules for each step of cloning of FIG. 5A. "Gene 1" is equivalent to "TU 1". Sequence stretches (SS) designated SS1 to SS26 are SEQ ID NO: 31 to SEQ ID NO: 56, respectively.

FIG. 5B show nucleotide sequences at the junction of various modules for each step of cloning of FIG. 5A. "Gene 1" is equivalent to "TU 1". Sequence stretches (SS) designated SS1 to SS26 are SEQ ID NO: 31 to SEQ ID NO: 56, respectively.

FIG. 6 is an overview of alternative cloning strategies. Every cloning step relies on three elements that are different from one level to the next: antibiotic selectable marker, type IIS restriction enzyme, and visual selectable marker. Cloning after level 2i-1 requires the use of two type IIS enzymes, such as BpiI-BsaI or BpiI-Esp3I. Using the described set of level 1 destination vectors, level 2 destination vectors and end linkers, and the indefinitely repeatable cloning strategy provided, as many transcription units can be added to a construct as desired by a user, using as many cycles of cloning as required. Physical limits will ultimately be encountered due to handling of very large constructs, but such limits will not come from the cloning strategy itself. The level 2 reactions are numbered by the numeral at position x in level 2-x.

Level 2-x stands for a level 2 reaction producing a level 2 reaction product that cannot be used for a further level 2 reaction due to the absence of a pair of type IIs restriction sites allowing reopening of the level 2 reaction product (e.g. due to the use of an end-linker of the pELE set, the last "E" indicating "end").

Level 2i-x stands for a level 2 reaction that produces a reaction product that is an intermediate (e.g. due to the use of an end-linker of the pELB set) and can thus be used for a further level 2 reaction.

Each level 2i-x reaction product opens up two possibilities for a further level 2 reaction (indicated by the branching arrows). Depending on the use of the end-linker, the next level 2 reaction will either lead to an end (boxed level 2-x) or will lead to a further intermediate reaction product, allowing a still further level 2 reaction.

FIG. 7 shows the structure of level 0 modules. All level 0 modules are flanked by two convergent BsaI sites (with respect to the insert such as P1). Five module classes, namely promoter modules, 5'UTR modules, signal peptide modules, ORF modules and terminator modules are depicted. All modules of a same class are flanked by the same cleavage sites (for promoter modules GGAG and TACT). This design allows to clone any module of a given class into a transcription unit using the same cloning strategy. It also allows the use of multiple modules from a module class for obtaining libraries of level 1 fragment constructs. Modules of different classes are designed to be compatible for assembly in a multi-fragment level 1 reaction, also referred to herein as "Golgen Gate" cloning reaction, i.e., the sites joining two modules form compatible (complementary) single-stranded overhangs after digestion with a type IIs restriction enzyme, here BsaI. A "set" designates a group consisting of 1 module from each of the five module classes.

Figure 8A:
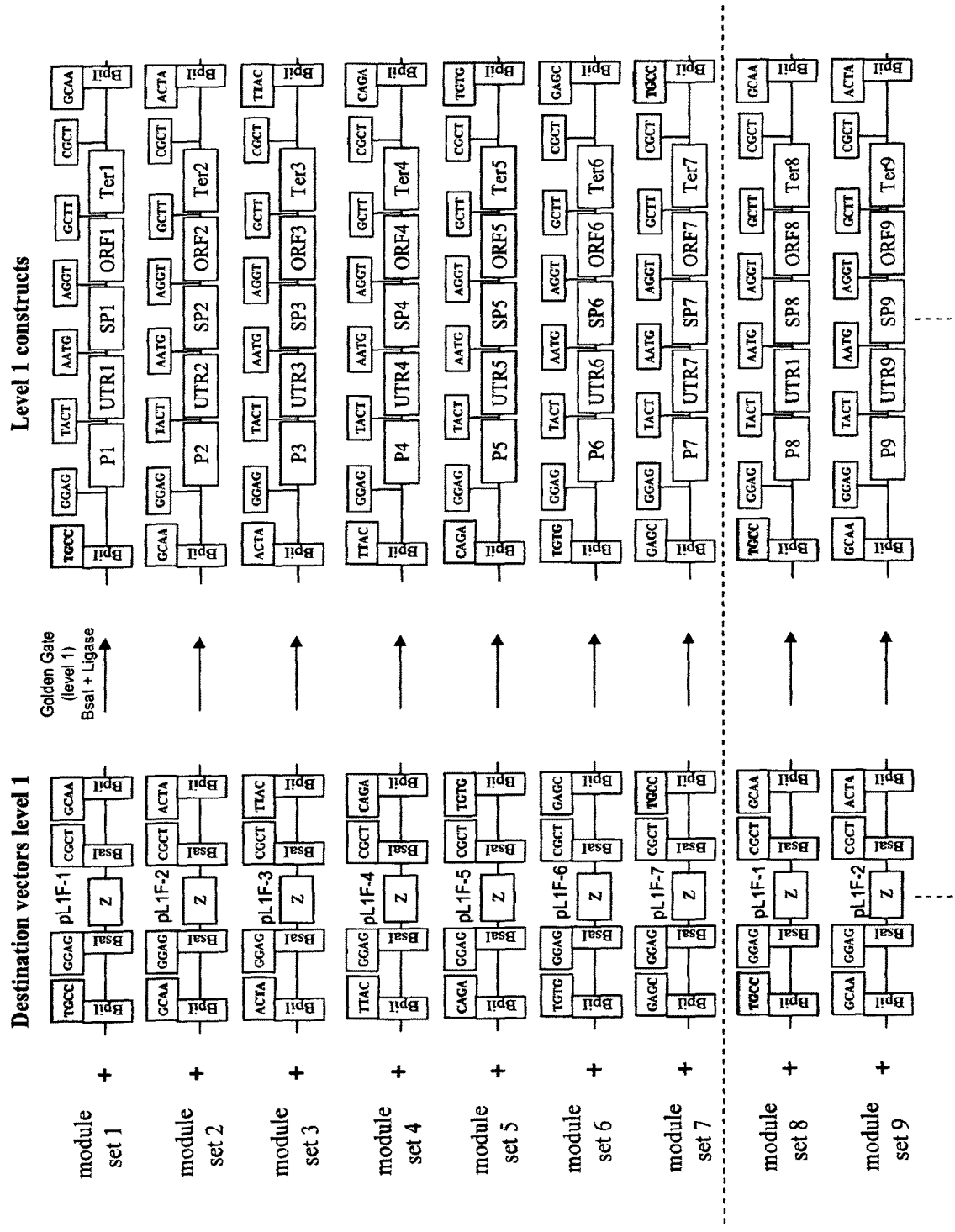
FIG. 8A explains the assembly of transcriptional units from level 0 modules into level 1 destination vectors (entry DNAs).

FIG. 8A explains the assembly of transcriptional units from level 0 modules into level 1 destination vectors (entry DNAs). Module sets 1 to 9 (each consisting of a set of level 0 modules as shown in FIG. 7) are assembled in a level 1 destination vector. Modules sets 1 to 7 are assembled in level 1 destination vectors pL1F-1 to -7 (see FIG. 4), respectively. Module sets 8 and 9 (and optional further sets) are cloned in the same series of level 1 destination vectors pLF-1, pLF-2 etc, respectively. Thus, level 1 destination vectors pL1F-1 and -2 (and optionally further vectors) are reused for a different module set than module sets 1 and 2. The reaction products are level 1 constructs having flanking BpiI restriction sites retained from the level 1 destination vectors. These flanking restriction sites define with their associated cleavage sites the order in which the level 1 constructs are ligated in the subsequent level 2 reaction. Each reaction shown is generally performed as a separate reaction.

Figure 8B:
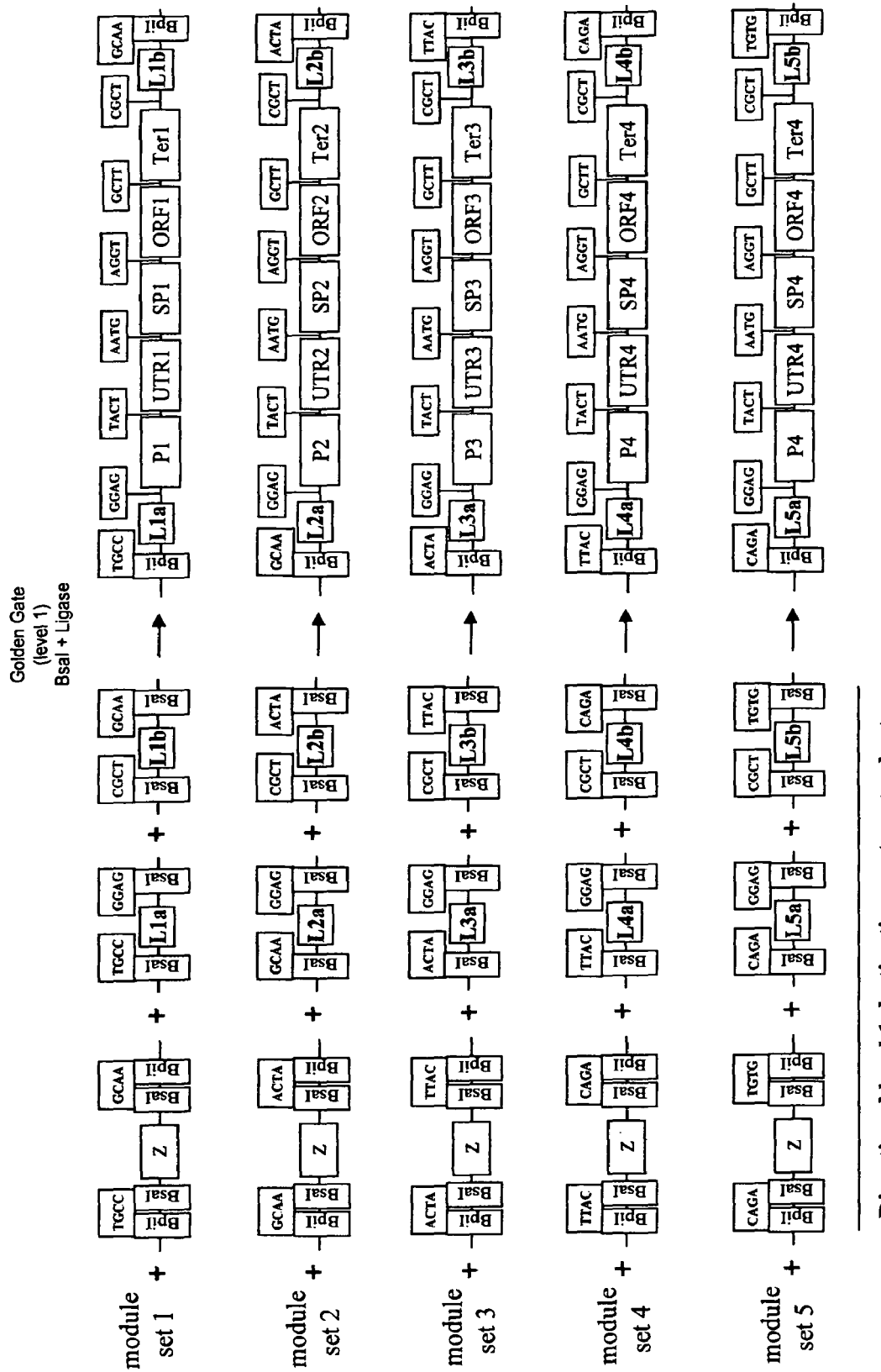
FIG. 8B illustrates an example for the assembly of level 0 modules using a different set of level 1 destination vectors.

FIG. 8B illustrates an example for the assembly of level 0 modules using a different set of level 1 destination vectors. In this example, the restriction sites for the enzyme BpiI are identical as in FIG. 1A, but the 4-nucleotide cleavage sites of the restriction sites for the enzymes BsaI and BpiI overlap exactly in each destination vector. As a consequence, the cleavage sites of the restriction sites for BsaI are not compatible with the previously described level 0 modules (in FIG. 7). In this embodiment, a set of adaptors that allow joining of the level 0 modules and of the level 1 destination vectors is employed. The resulting level 1 constructs have the same overall structure as the constructs made in FIG. 8A: the different transcription units are all flanked by the same compatible sets of BpiI restriction sites. These sites are convergent in each construct, and are compatible from one construct to the next.

Figure 9A:
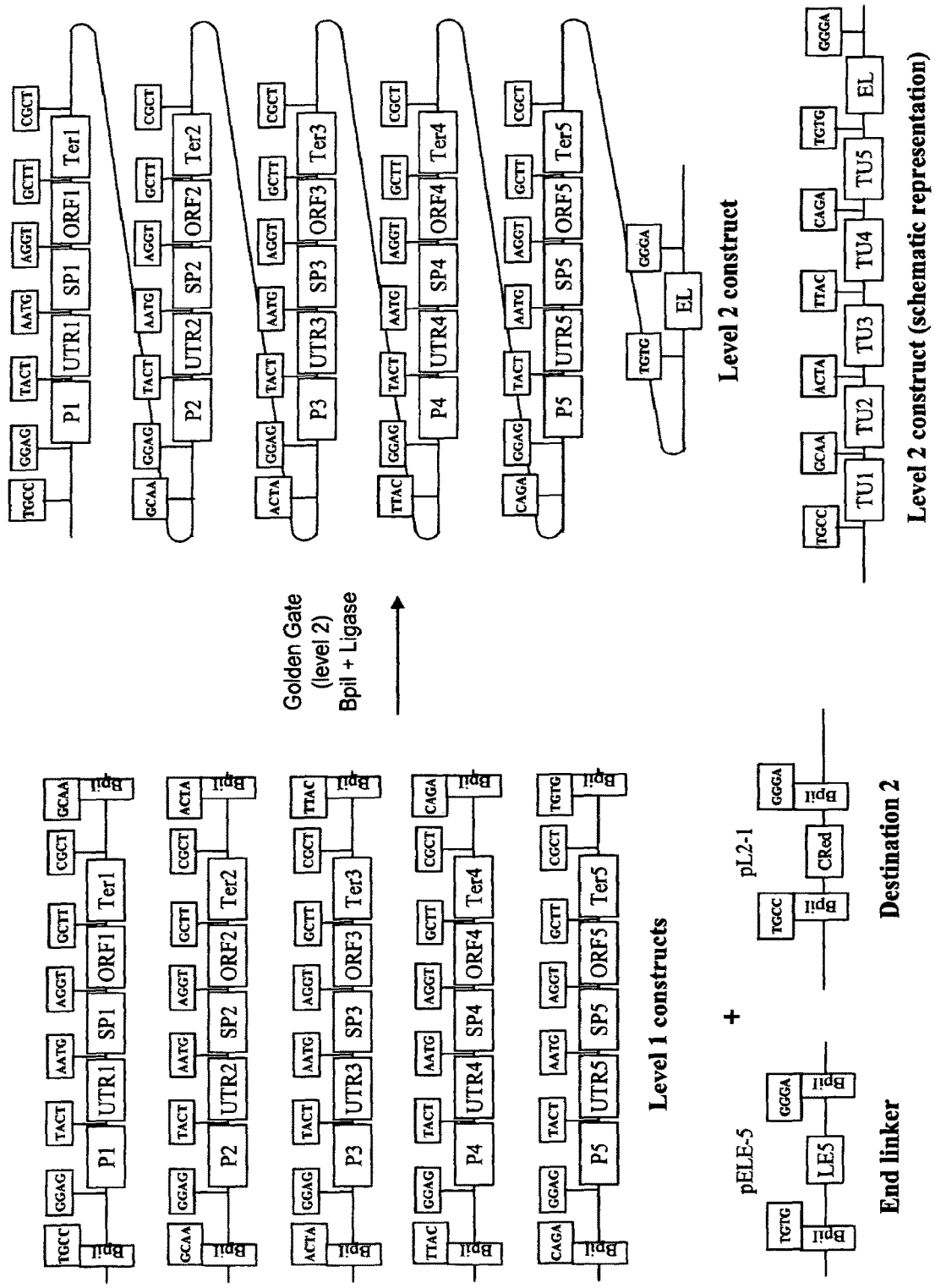
FIG. 9A: assembly of 5 transcription units into a multi-gene level 2 construct in a level 2 reaction.

FIG. 9A: assembly of 5 transcription units into a multi-gene level 2 construct in a level 2 reaction. An appropriate end linker is used for linking the right-hand side of the fifth level 1 construct to the GGGA cleavage site of the destination vector referred to as "Destination 2". The type of end-linker used does not allow the reaction product to be used as a starting material for a further level 2 reaction. The term "Golden Gate" means that reactants having type IIs restriction sites with compatible cleavage sites are combined in desired order in a reaction comprising restriction and ligation. The level 2 construct is shown on the right hand side in two different representations with different degrees of detail.

Figure 9B:
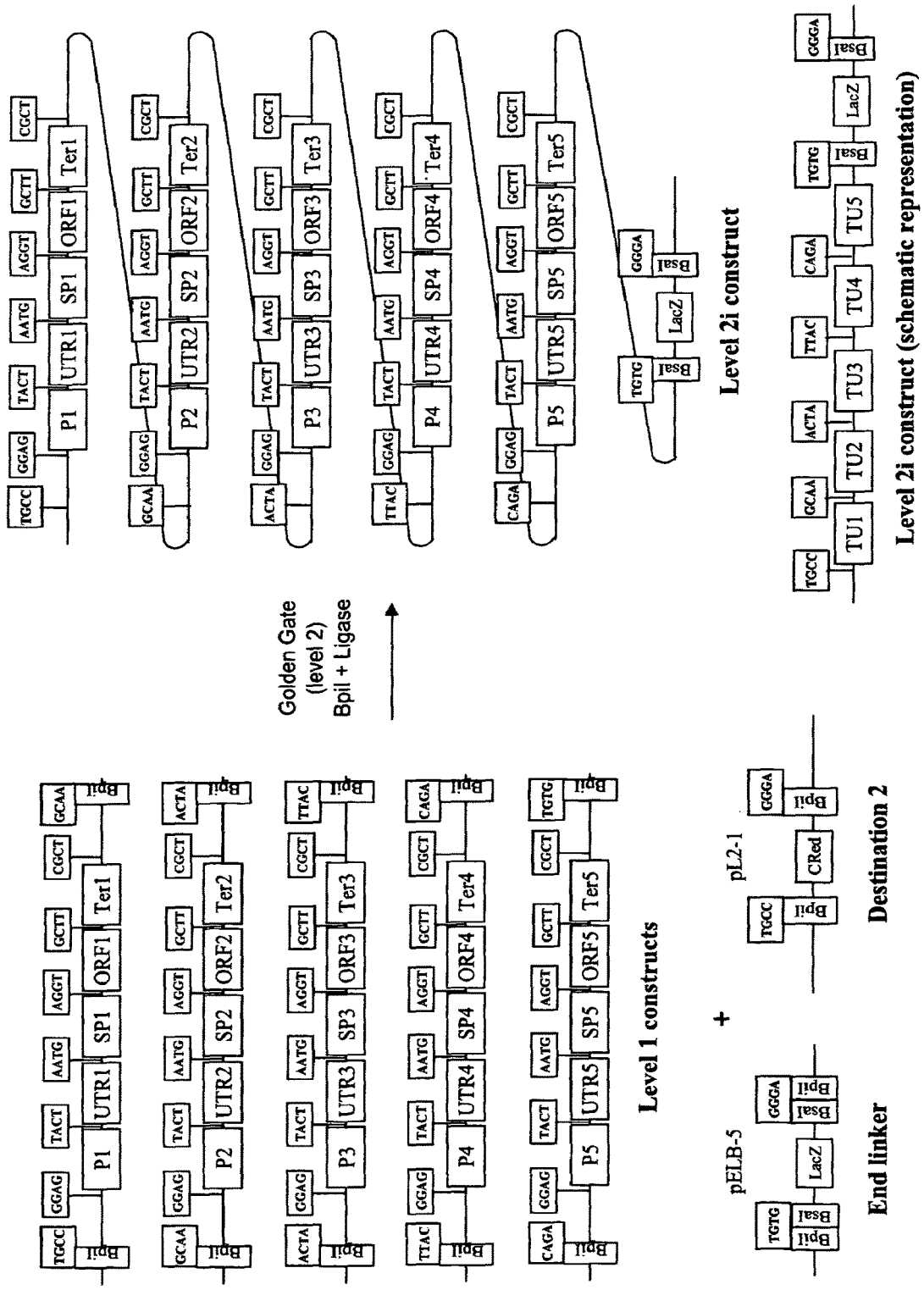
FIG. 9B: Assembly is performed with an end linker containing internal divergent BsaI restriction sites for allowing a further level 2 reaction in the resulting level 2 construct.

FIG. 9B: Assembly is performed with an end linker containing internal divergent BsaI restriction sites for allowing a further level 2 reaction in the resulting level 2 construct.

Figure 9C:
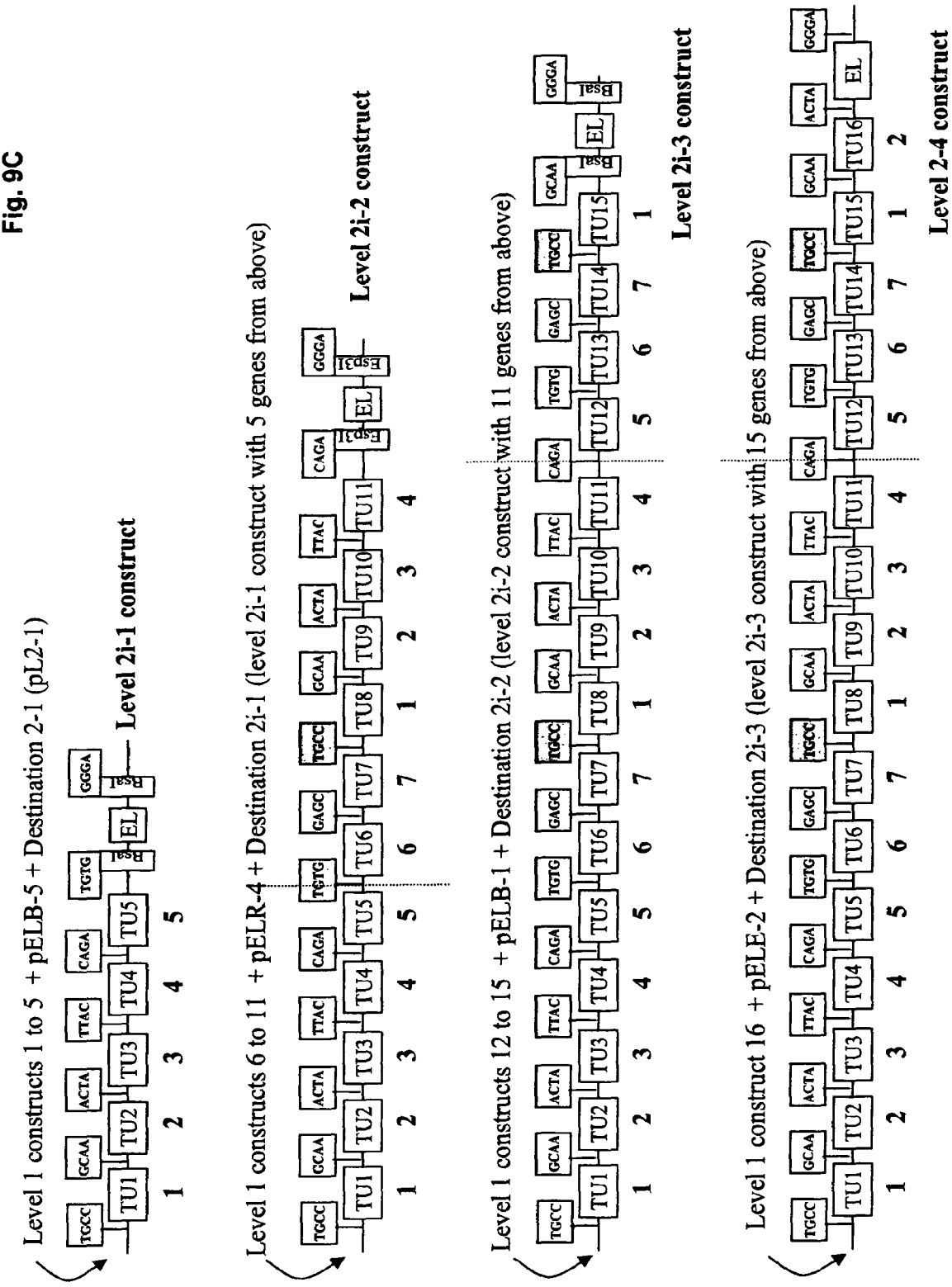
FIG. 9C shows examples of further rounds of cloning.

FIG. 9C shows examples of further rounds of cloning. At the top, a short version of the reaction of FIG. 9B is shown, whereby a level 2i-1 construct is obtained. In the next level 2 reaction, 6 transcription units (designated TU6 to TU11) are added to the level 2i-1 construct, leading to a level 2i-2 construct. In the next step, four further TUs (designated TU12 to TU15) are added, leading to the level 2i-3 construct. In a further step shown at the bottom, one further TU (TU16) is added to obtain the level 2-4 construct. At each successive cloning step, different end linkers have to be used, that may contain either internal BsaI or Esp3I restriction sites, or none if the final round of cloning is reached.

FIG. 10 shows the efficiency of cloning for different levels of assembly. For level 1 and level 2-1, all minipreps analyzed contained only correctly assembled constructs, even though multiple fragments were assembled in a one-pot one-step reaction for each construct. Moreover, the last level 2-1 construct was obtained by assembly in one step of 6 transcription units and one end-linker in one destination vector. Despite the large size and large number of components, all minipreps analyzed contained only correct constructs. The final construct made contains 11 transcription units. All colonies analyzed contained correct constructs despite the large size of the construct (34 kb), FIGS. 11 to 17 show how the cloning system of this invention can be used to create constructs containing one or multiple operons. Applications include microbial strain construction for metabolic engineering.

Figure 11:
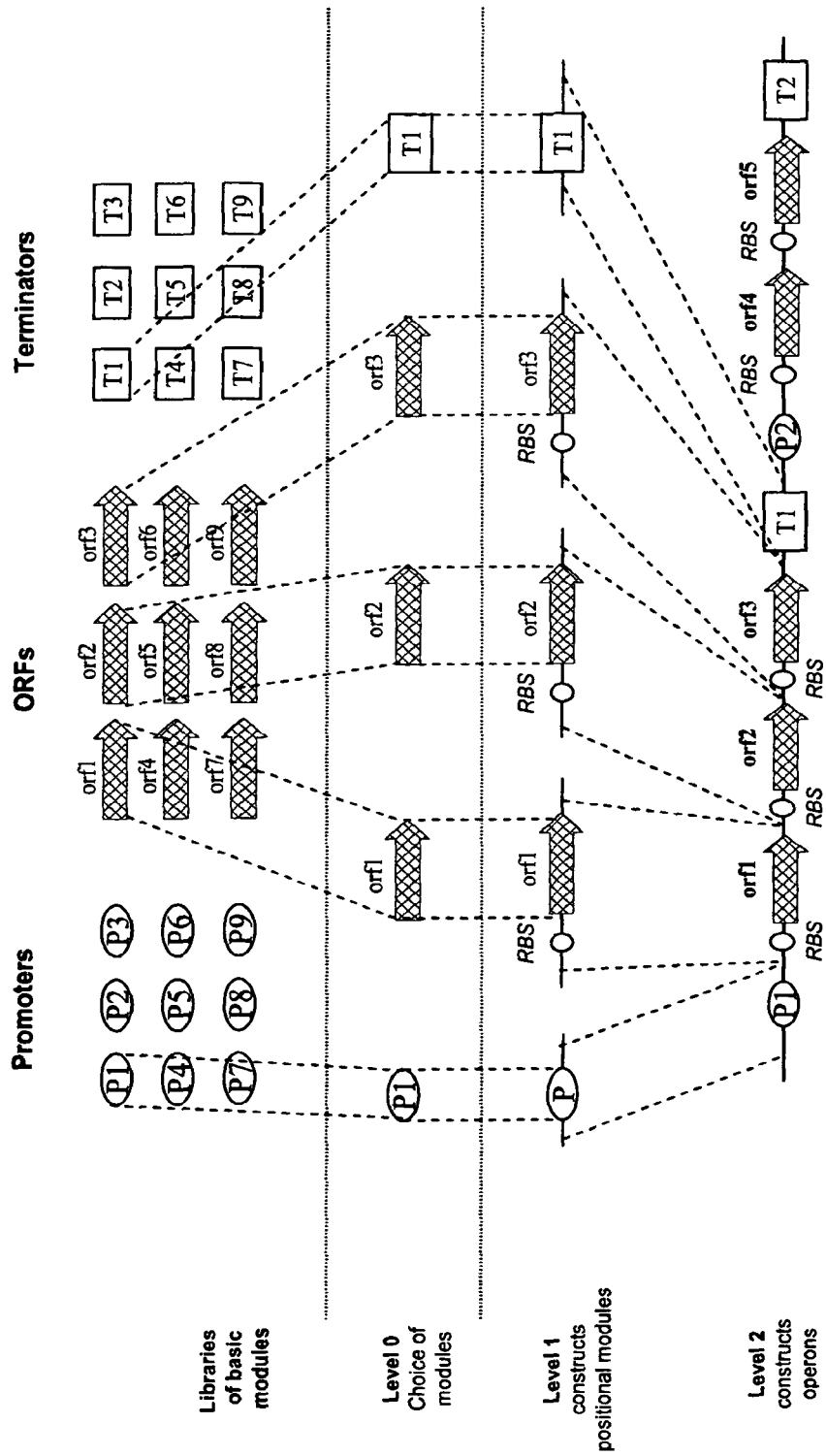
FIG. 11 illustrates the general strategy used for cloning of prokaryotic operons.

FIG. 11 illustrates the general strategy used for cloning of prokaryotic operons. Basic genetic elements such as promoters, open reading frames (ORFs), and terminators are cloned as level 0 modules. Libraries of level 0 modules or individual level 0 modules can be stored until needed for cloning. To make a desired construct, a selected number of genetic elements cloned as level 0 modules are chosen. Unlike for cloning of eukaryotic multigene constructs, promoters, open reading frames and terminators are not cloned together in a level 1 destination vector. The reason for this design is that different operons may contain a different number of open reading frames, preventing the design of a fixed set of compatible cleavage sites for cloning. Rather, promoters, open reading frames and terminators are cloned separately in different level 1 destination vectors to obtain level 1 constructs. Rather than serving the purpose to assemble several level 0 modules together, cloning in level 1 destination vectors for prokaryotes serves mainly the purpose of providing positional information for the cloned level 1 construct for a subsequent level 2 assembly. Complete or partial operons are then cloned from several level 1 constructs in a one-pot one-step cloning reaction on level 2.

Figure 12:
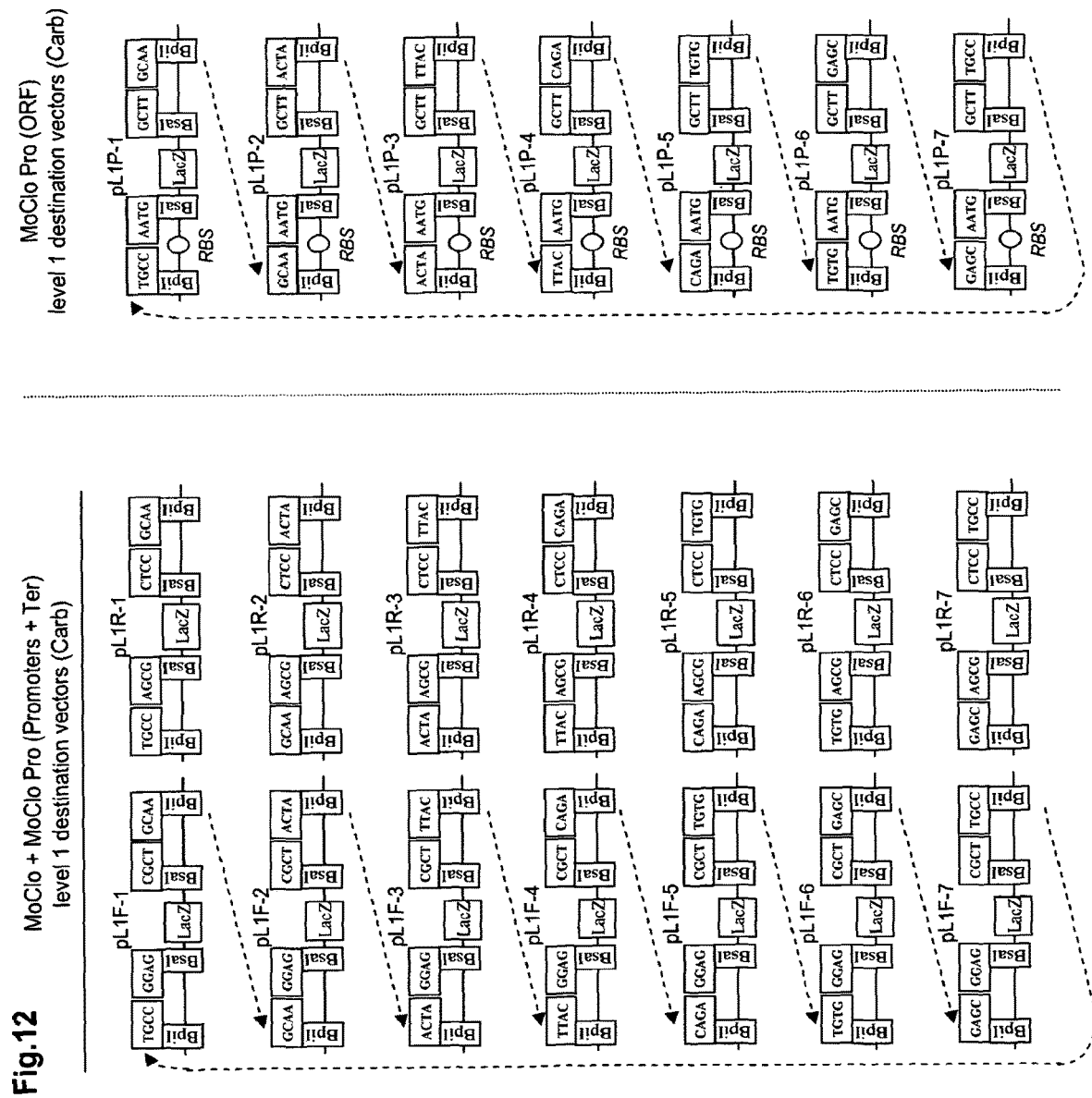
FIG. 12 Comparison of level 1 destination vectors for eukaryotes ("MoClo") and prokaryotes ("MoClo Pro").

FIG. 12 Comparison of level 1 destination vectors for eukaryotes ("MoClo") and prokaryotes ("MoClo Pro"). Level 1 destination vectors (entry DNAs) for cloning promoters and terminators for prokaryotic operons may be the same as level 1 destination vectors made for eukaryotes (FIG. 4). In contrast, level 1 destination vectors made for prokaryotic ORFs (open reading frames) have different internal BsaI sites (AATG and GCTT). In addition, they contain a ribosome binding site between the first BpiI and BsaI cleavage sites. There are many possible designs for level 1 destination vectors other than the ones described here. However, despite these differences, all destination vectors also have the same general structure in common, namely two convergent type IIs enzymes flanking the DNA sequence of interest, and cleavage sites designed to fit the structure of nucleic acids 1 to 7 shown in FIG. 1A.

Figure 13:
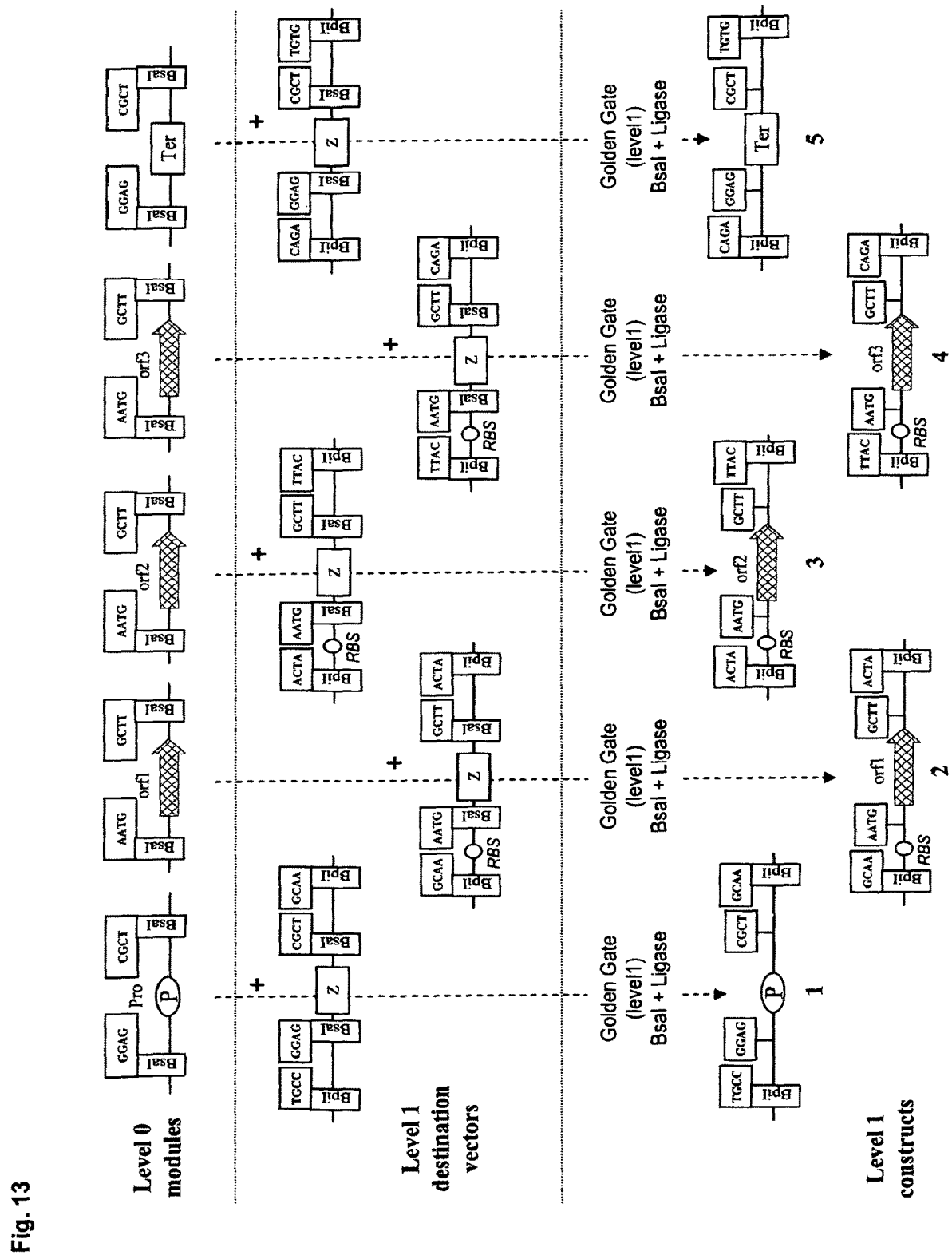
FIG. 13 illustrates the cloning of 5 level 1 constructs (shown in the lower part) from level 0 modules into level 1 destination vectors (shown in the middle part) in a level 1 reaction.

FIG. 13 illustrates the cloning of 5 level 1 constructs (shown in the lower part) from level 0 modules into level 1 destination vectors (shown in the middle part) in a level 1 reaction. Level 1 destination vectors shown in FIG. 12 are used. Five level 1 constructs, namely a promoter construct, 3 ORF constructs and a terminator construct are obtained with compatible cleavage sites for ligation, in the order given, in the subsequent level 2 reaction.

Figure 14:
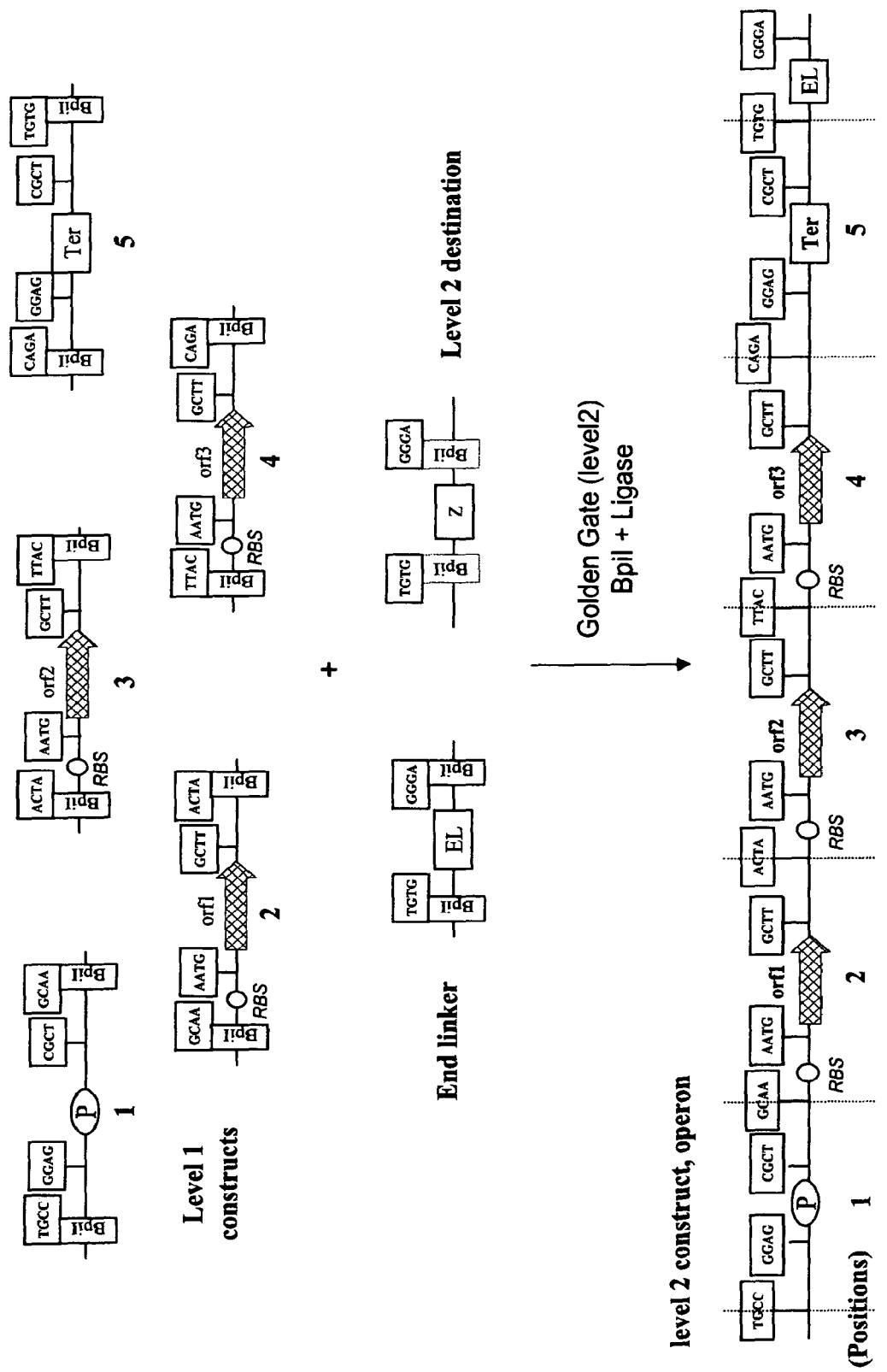
FIG. 14 shows the level 2 reaction from the level 1 constructs made as shown in FIG. 13 to produce a functional operon in a level 2 construct.

FIG. 14 shows the level 2 reaction from the level 1 constructs made as shown in FIG. 13 to produce a functional operon in a level 2 construct.

Figure 15:
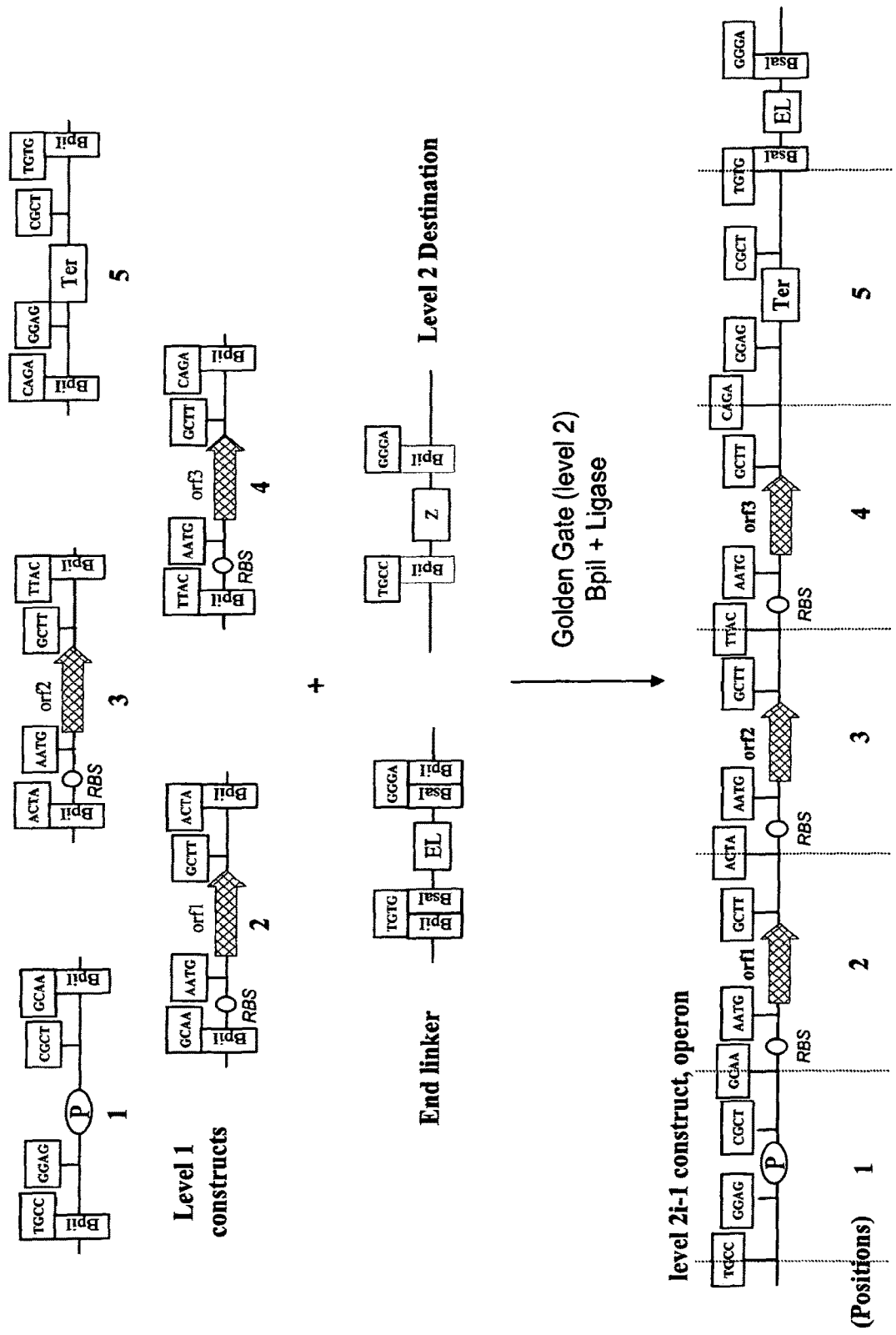
FIG. 15 shows a similar level 2 reaction as shown in FIG. 14, but with an end-linker containing internal BsaI sites for allowing a further level 2 reaction.

FIG. 15 shows a similar level 2 reaction as shown in FIG. 14, but with an end-linker containing internal BsaI sites for allowing a further level 2 reaction.

Figure 16:
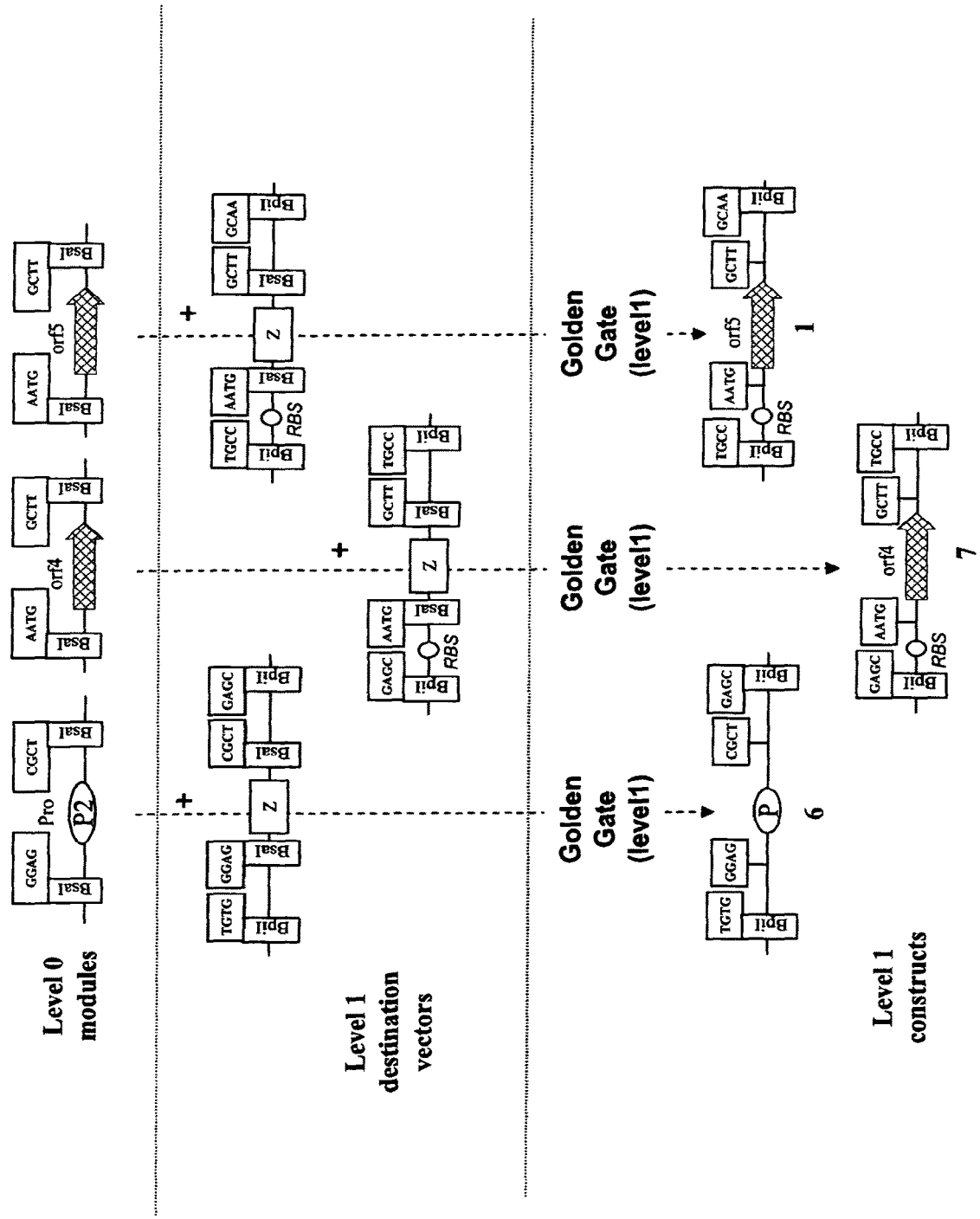
FIG. 16 illustrates the preparation of 3 additional level 1 constructs (designated 6, 7 and 1, respectively) containing a second promoter (P2) and two further ORFs (orf4 and orf5).

FIG. 16 illustrates the preparation of 3 additional level 1 constructs (designated 6, 7 and 1, respectively) containing a second promoter (P2) and two further ORFs (orf4 and orf5). The level 1 destination vector for orf4 is the last destination vector of a set of n=7 entry DNAs. The right hand cleavage site thereof having sequence TGCC allows reuse of the first level 1 destination vector (pL1P-1 in FIG. 12) for orf5.

Figure 17:
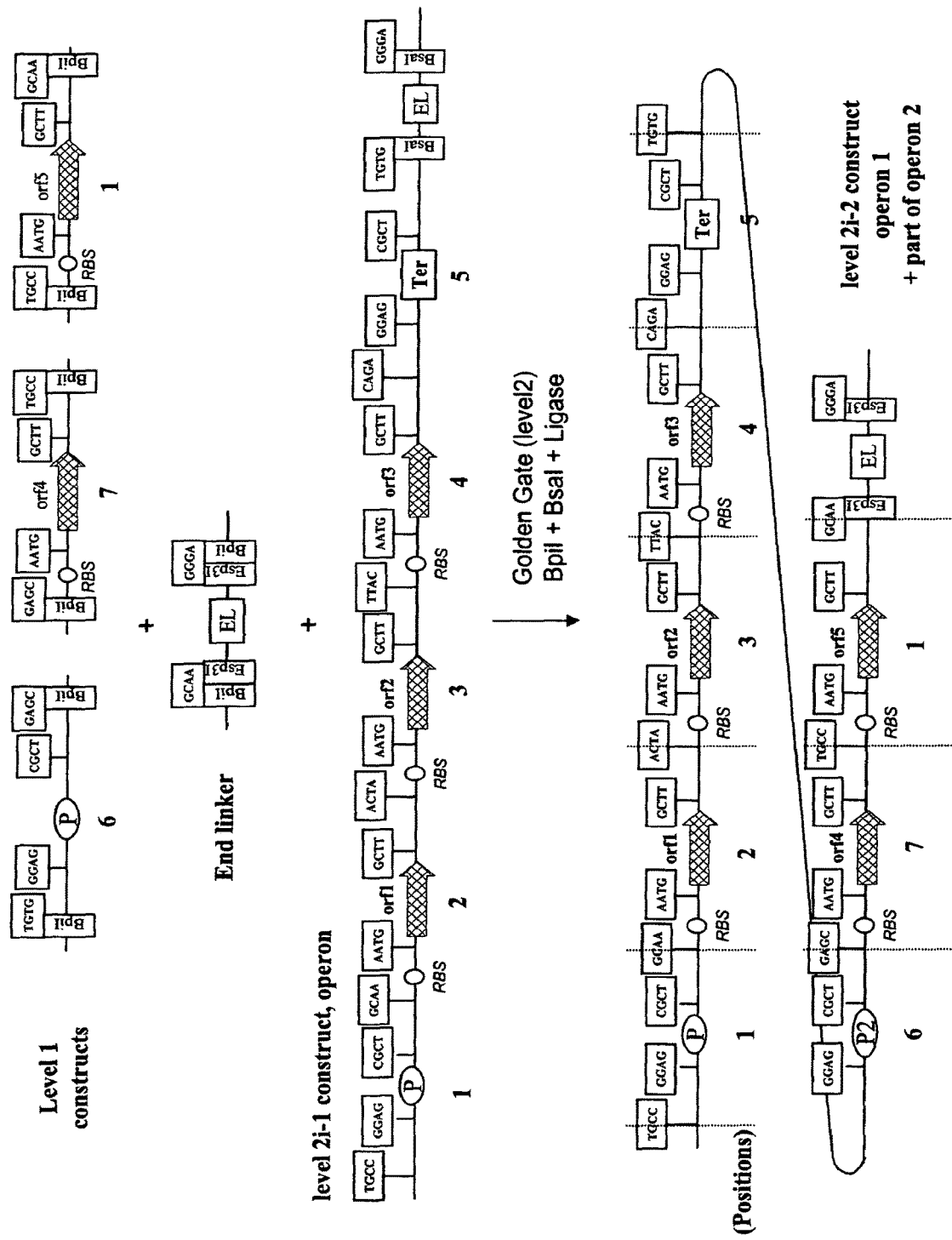
FIG. 17. Cloning of the three additional level 1 constructs obtained according to FIG. 16 into the level 2i-1 construct made according to FIG. 15.

FIG. 17. Cloning of the three additional level 1 constructs obtained according to FIG. 16 into the level 2i-1 construct made according to FIG. 15. The reaction product shown at the bottom is a level 2i-2 construct, since the end-linker used allows a subsequent level 2 reaction.

The following figures further illustrate the examples.

FIGS. 18A-18C show the structure of transcriptional units, level 0 modules, and of destination vectors required for their cloning.

FIG. 18A: The transcriptional units contain up of 5 basic modules separated by 4 nucleotides sequences that serve as recombination sites (shown in boxes).

FIG. 18B: Level 0 modules shown on the first line are flanked by BsaI sites. The modules are cloned in a level 0 reaction using the enzyme BpiI and one of the level 0 destination vectors shown underneath.

FIG. 18C: Strategy for removing internal type IIS recognition sequences. Removal of a BsaI site in a fragment of interest is done by amplifying two fragments with primers pr1 (SEQ ID NO: 27) and 2 (SEQ ID NO: 28) and primers pr3 (SEQ ID NO: 29) and 4 (SEQ ID NO: 30). Sequences of the BpiI recognition sites in the 5' extensions in the primers (horizontal arrows) are shown in bold. The two fragments are cloned using BpiI in the appropriate level 0 destination vector, for example pL0-P in the present example.

FIGS. 19A-19D show an example for cloning of constructs of level 0, 1 and 2. Antibiotic resistances are indicated.

FIG. 19A: Illustrates cloning of level 0 promoter modules.

FIG. 19B: Illustrates cloning of a level 1 construct containing a transcription unit.

FIG. 19C: Illustrates cloning of a level 2i-1 construct containing 5 transcription units, TU1 (containing GFP), TU2 (containing p19), TU3 (containing VP2), TU4 (containing VP5), TU5 (containing VP7) into destination vector pL2-1.

FIG. 19D: Illustrates cloning of a level 2-2 construct containing 11 transcription units. In addition to TU1 to TU5, the construct contains TU6 (transcription unit with VP3), TU7 (transcription unit with BAR), TU8 (transcription unit with antibody light chain), TU9 (transcription unit with antibody heavy chain), TU10 (transcription unit with TMV MP), TU11 (transcription unit with TMV CP).

FIG. 20A shows the structure of the 11 level 1 transcription units used in FIG. 19B. FIG. 20B shows the structure of construct pICH51811 that is obtained by cloning of the 11 transcription units cloned in a level 2-2 construct.

Figure 21:
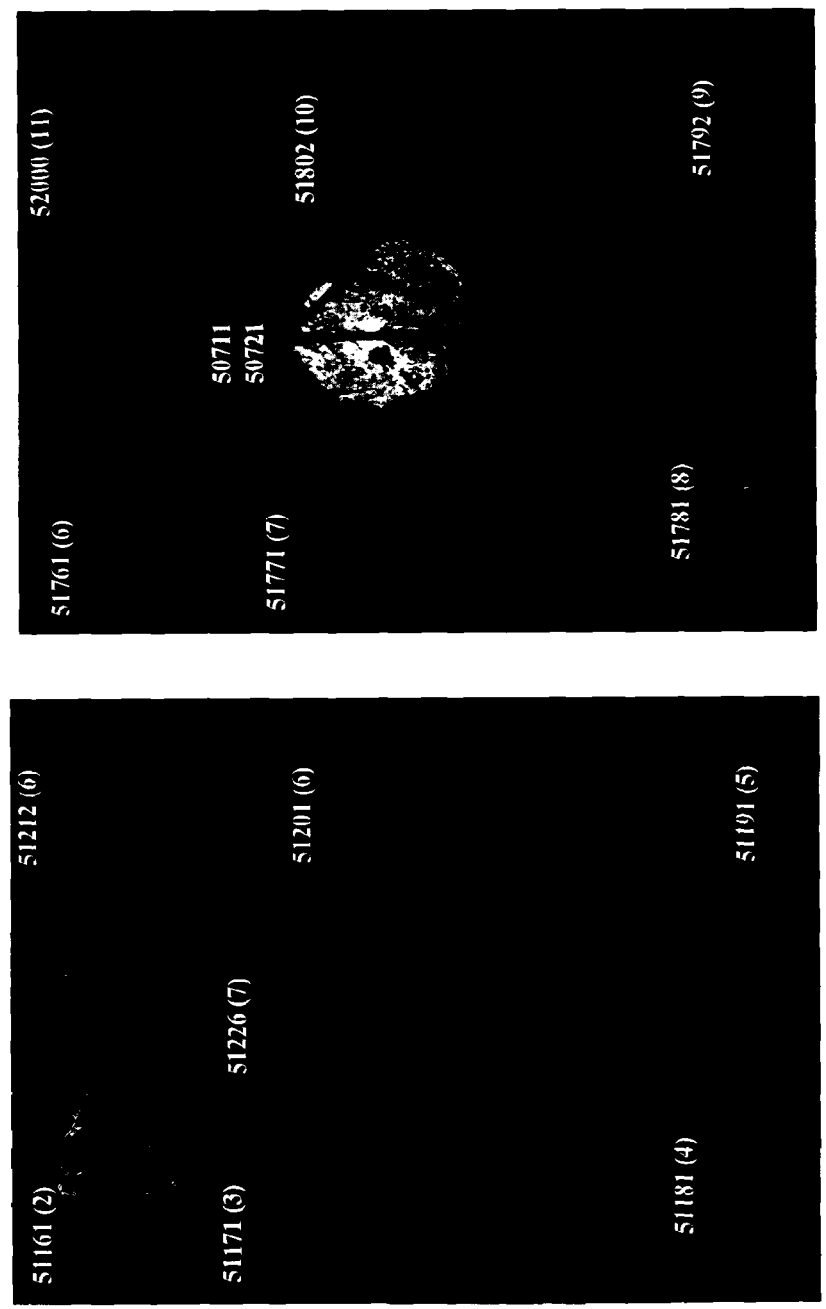
FIG. 21 shows the expression of GFP in a *Nicotiana benthamiana* leaf after infiltration of level-2 constructs shown in FIG. 10.

FIG. 21 shows the expression of GFP in a *Nicotiana benthamiana* leaf after infiltration of level-2 constructs shown in FIG. 10. The level-2 constructs were transformed in *Agrobacterium tumefaciens*, and the transformed bacteria infiltrated in leaves using a syringe without a needle. GFP expression was observed at 5 dpi under UV light. The number in parenthesis indicates the number of transcription units in each infiltrated construct.

FIG. 22 shows prokaryotic genes cloned as level 0 entry modules. 3 genes from *Pantoea ananatis* crtE, I, and B are involved in lycopene biosynthesis. Other genes known to increase lycopene expression when overexpressed in *E. coli* were also cloned: dxs from *Agrobacterium rhizogenes* strain K84 and *E. coli* strain K12, the ispA genes from the same two species, and the idi and AppY genes from *E. coli* strain K12. Two promoters were also cloned as level 0 modules: the Lac Z promoter from pUC19, and a promoter from *Pantoea ananatis*.

Figure 23:
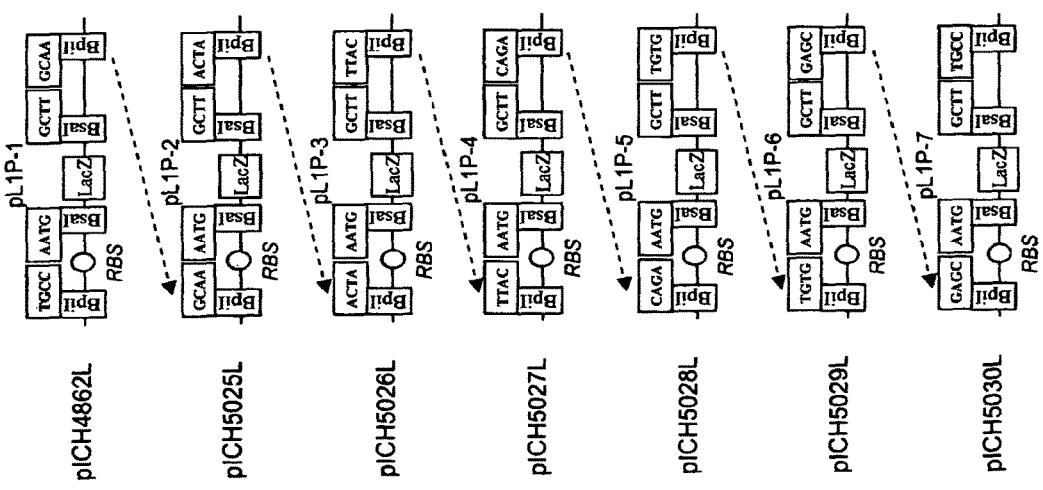
FIG. 23A shows level 1 destination vectors for cloning of prokaryotic coding sequences.
FIG. 23B shows two sets of end linkers that contain the LacZ terminator from pUC19.

FIG. 23A shows level 1 destination vectors for cloning of prokaryotic coding sequences. All constructs are in fact libraries (indicated by the L in the construct name) that have variable sequences flanking the RBS. FIG. 23B shows two sets of end linkers that contain the LacZ terminator from pUC19.

Figure 24:
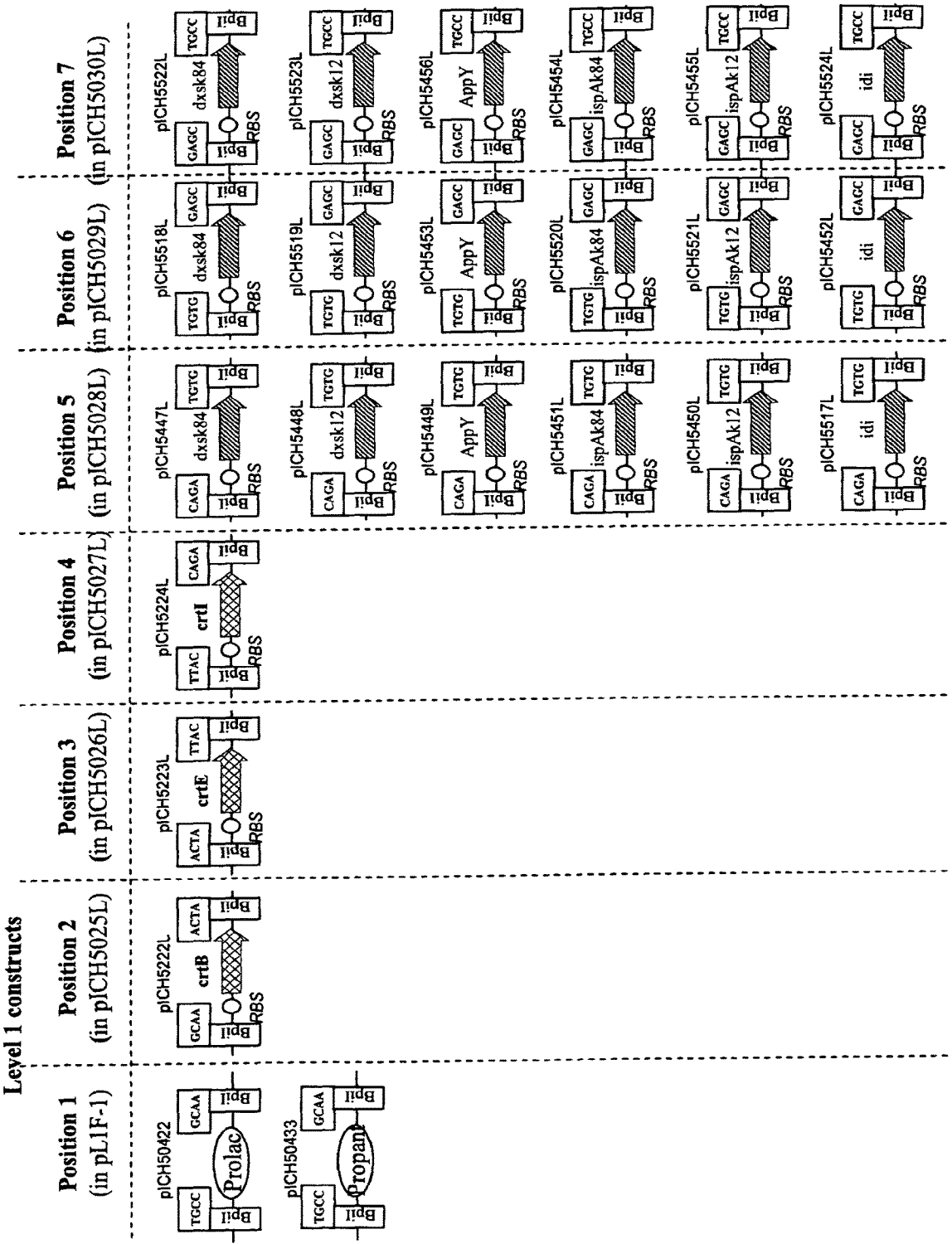
FIG. 24 shows a list of level 1 constructs made with the level 0 modules shown in FIG. 22.

FIG. 24 shows a list of level 1 constructs made with the level 0 modules shown in FIG. 22.

Figure 25:
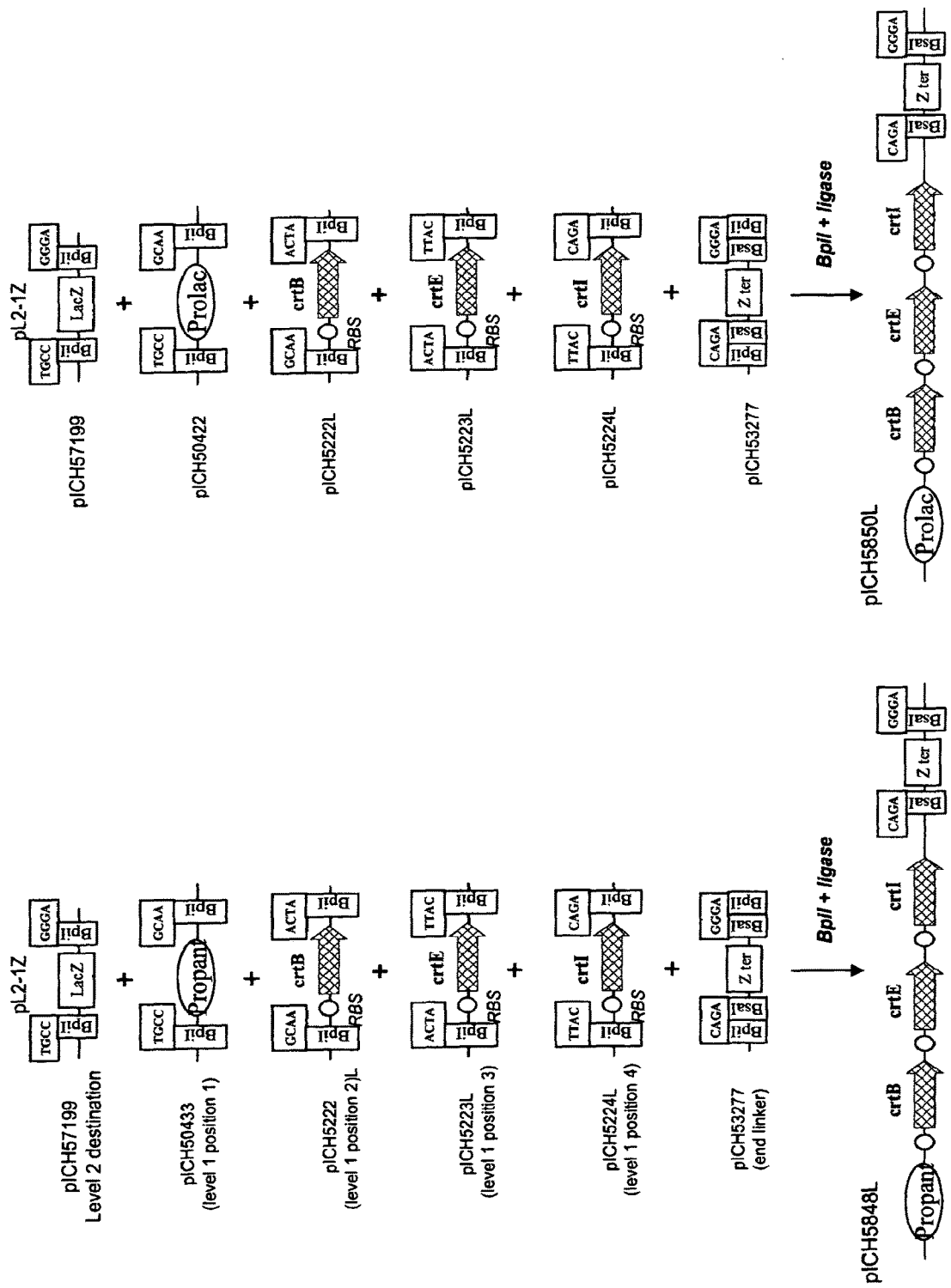
FIG. 25 shows level 2i-1 constructs.

FIG. 25 shows level 2i-1 constructs. Two libraries were made with genes for lycopene biosynthesis. Both constructs pICH5648L and pICH5850L are in fact libraries in which all clones obtained differ in the sequence flanking the RBS of all three cloned genes.

Figure 26:
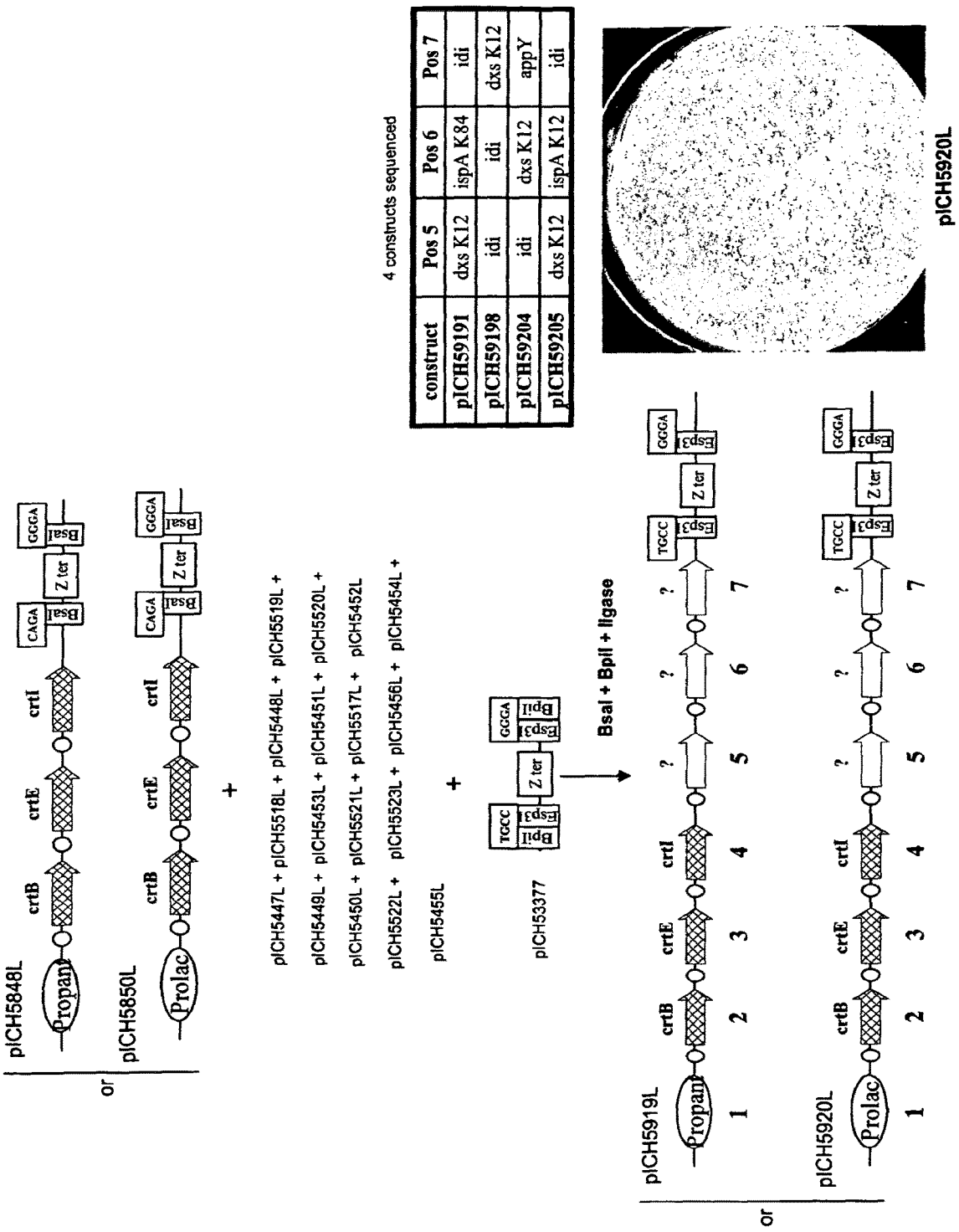
FIGS. 26A-26B show addition of two or three more genes to the operons obtained in FIG. 25.

FIGS. 26A-26B show addition of two or three more genes to the operons obtained in FIG. 25. Since a library of different constructs was placed in the cloning mixes (pICH5447L to pICH5452L in FIG. 26A, or pICH5455L in FIG. 26B) the constructs obtained consist of libraries of constructs that differ in the genes present at positions 5 and 6 or 5, 6 and 7. The number of different gene combinations for library pICH5920L is in theory 216 possibilities, without even considering the variation provided by variability in the 5 RBS regions of the 5 genes per operon.

Figure 27:
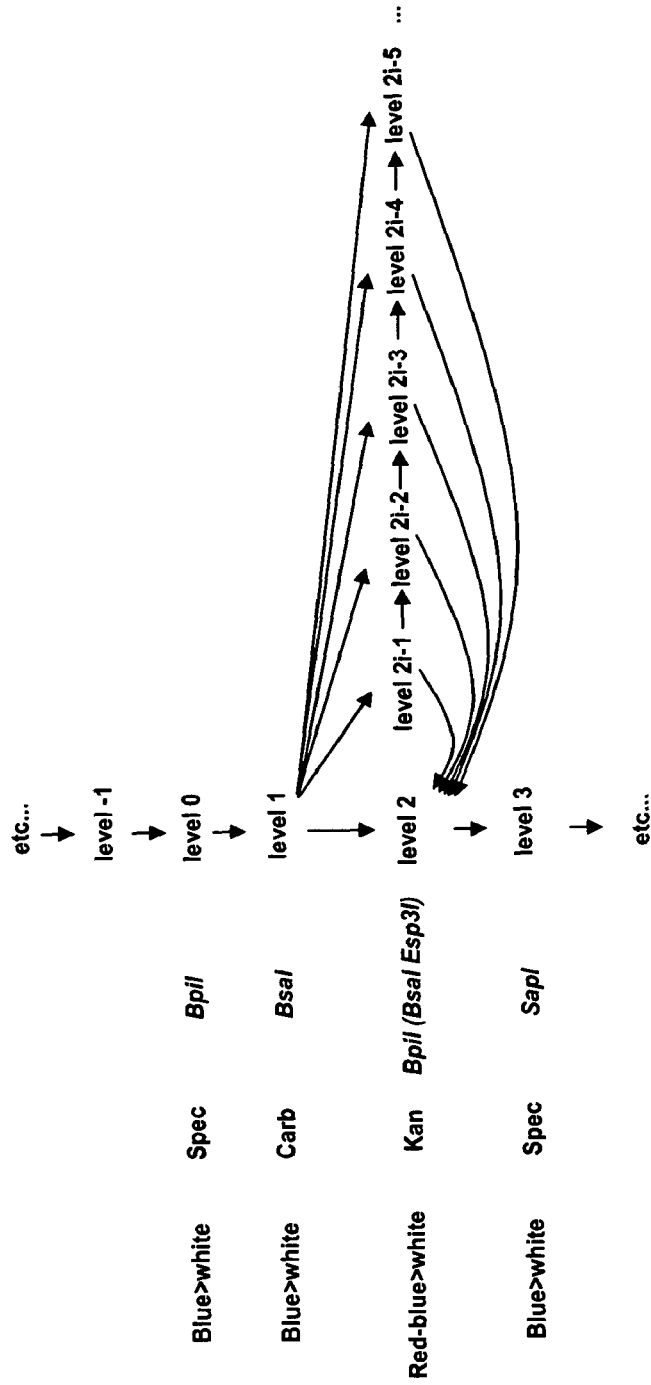
FIG. 27 shows that level 2 cloning can be followed by a level 3.

FIG. 27 shows that level 2 cloning can be followed by a level 3. For this, a new type IIs enzyme needs to be used, such as SapI in the case shown.

Figure 28:
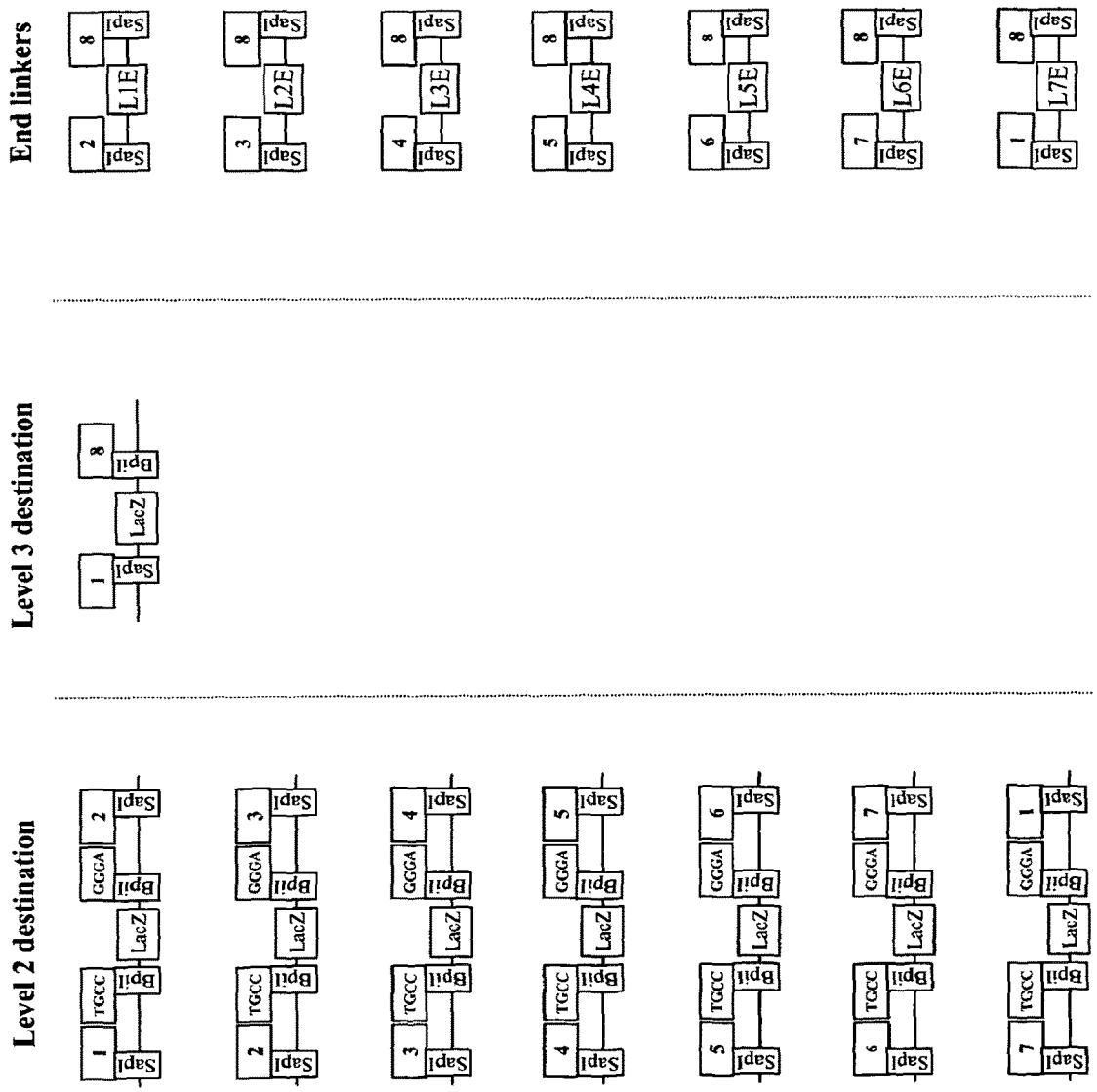
FIG. 28 shows vectors required for level 3 cloning.

FIG. 28 shows vectors required for level 3 cloning. Level two destination vectors are flanked by restriction sites of a new type IIs enzyme (SapI in this example). Level 3 destination vectors and end-linkers are similar as for level 2, but with the new type IIS enzyme. Numbers 1 to 8 represent eight different 3 nucleotide sequences as the cleavage site of SapI.

FIG. 29A shows a set of destination vectors and end-linkers for assembly of several level 1 transcription units (or more generally nucleic acids "na") into a level M destination vector (M stands for multiplication). Level M destination vectors and corresponding end-linkers (ELM1 to 7) are designed in such a way that blocks of assembled transcription units (or nucleic acid fragments) cloned in level M destination vectors become flanked by cleavage sites for a type IIs restriction enzyme, which will be used for the next step of cloning. In contrast to level 2 constructs where types IIs enzymes restriction sites are located at the end of the constructs in the end-linker, here the type IIs enzymes flank the assembled nucleic acid fragments, allowing them to be further subcloned in a new vector.

FIG. 29B illustrates assembly of three transcription units (nucleic acid acids na1 to 3) in a level M destination vector. The linker is chosen from the set of linkers ELM1 to ELM7 such that na3 can be linked to cleavage site S8 of destination vector M.

Figure 29C:
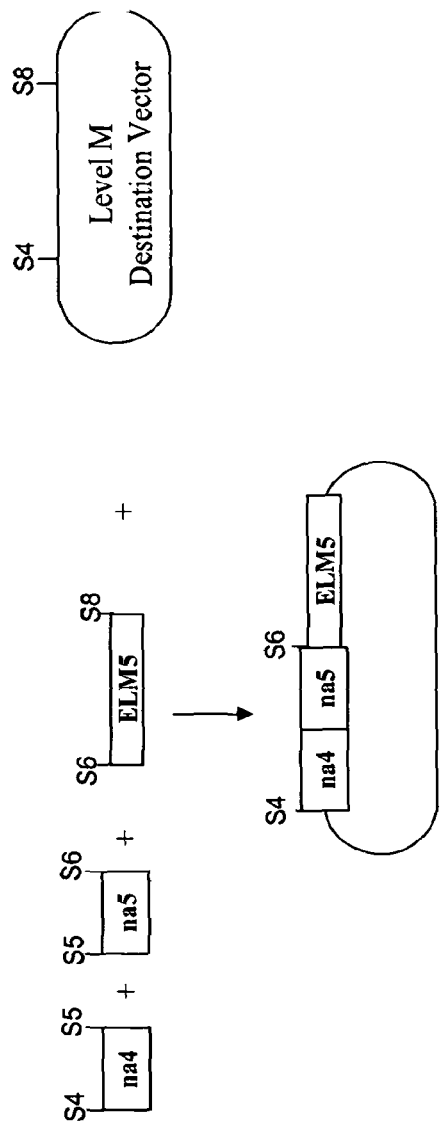
FIG. 29C illustrates assembly of two transcription units (nucleic acids na4 and 5) in a level M destination vector. The linker is chosen from the set of linkers ELM1 to ELM7 such that na5 can be linked to cleavage site S8 of destination vector M.

FIG. 29C illustrates assembly of two transcription units (nucleic acids na4 and 5) in a level M destination vector. The linker is chosen from the set of linkers ELM1 to ELM7 such that na5 can be linked to cleavage site S8 of destination vector M.

Figure 29D:
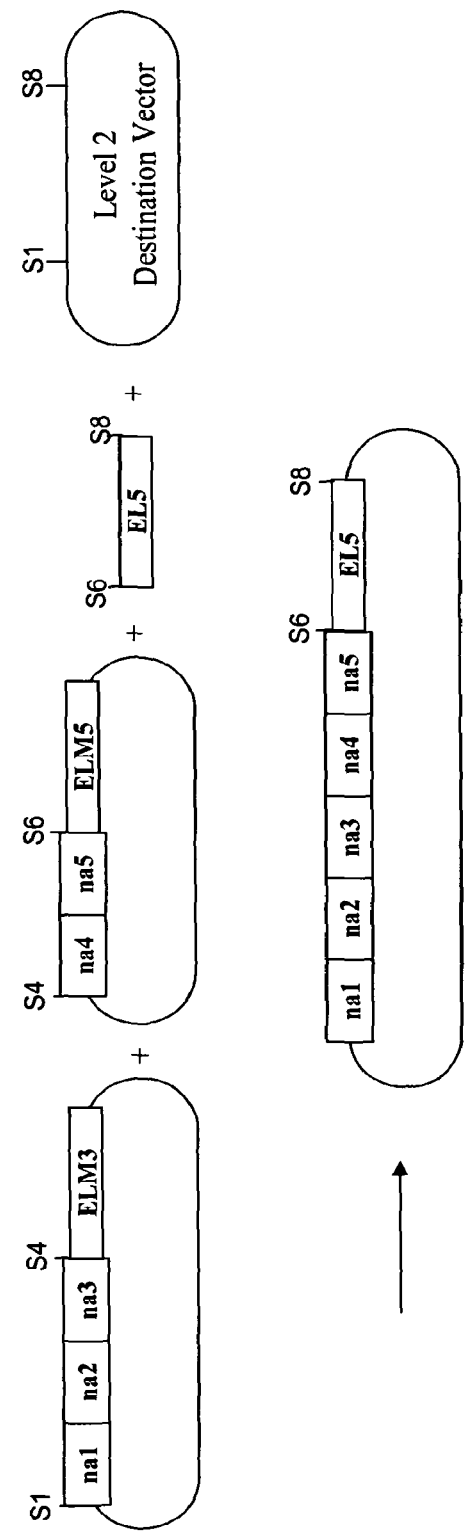
FIG. 29D shows assembly of the two pre-assembled blocks of transcription units (the reaction products of the reactions shown in B and C) in a level 2 construct employing a level 2 destination vector. Details of the restriction sites of destination vectors and end-linkers are shown in FIGS. 31 and 32 (below).

FIG. 29D shows assembly of the two pre-assembled blocks of transcription units (the reaction products of the reactions shown in B and C) in a level 2 construct employing a level 2 destination vector. Details of the restriction sites of destination vectors and end-linkers are shown in FIGS. 31 and 32 (below).

Figure 30:
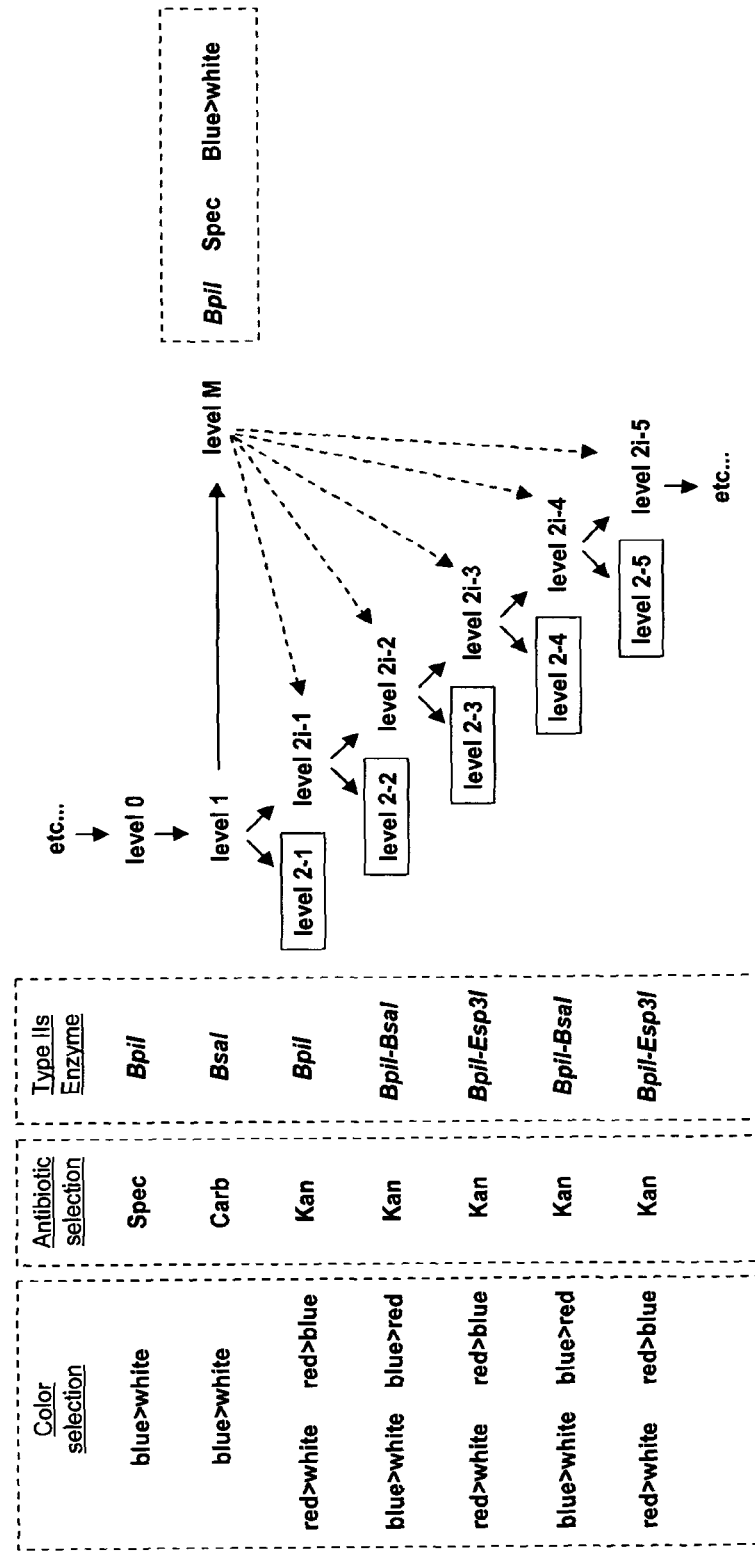
FIG. 30 shows that level M can be used as an intermediate step between level 1 and 2.

FIG. 30 shows that level M can be used as an intermediate step between level 1 and 2. Examples for color selection, antibiotic selection and type IIs enzymes for each step are shown.

Figure 31:
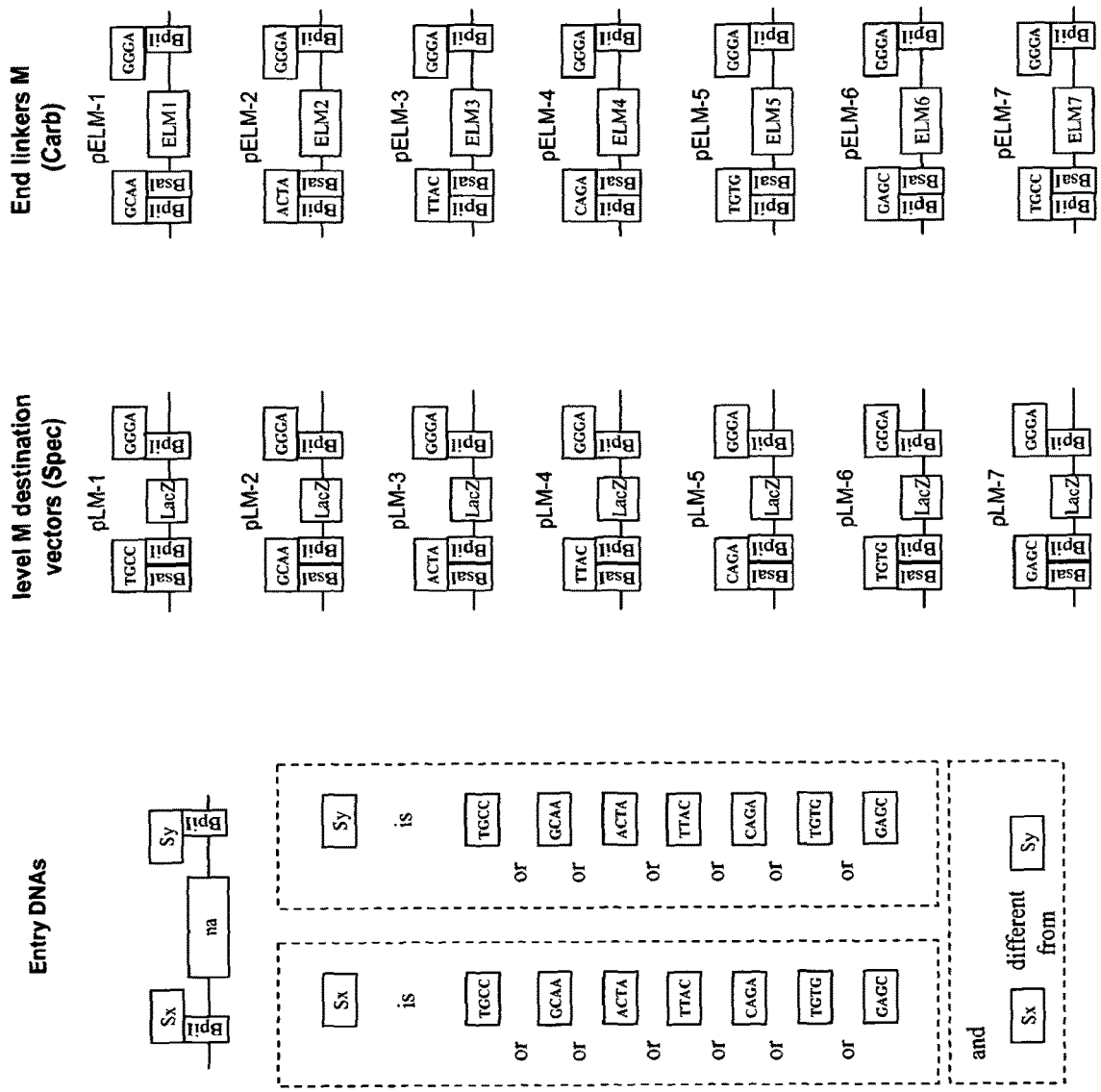
FIG. 31 shows the structure of the entry DNAs as well as vectors required for level M cloning.

FIG. 31 shows the structure of the entry DNAs as well as vectors required for level M cloning. A set of n=7 level M destination vectors and a set of n=7 linkers M is shown. Similarly as level 2 cloning, level M requires destination vectors and a set of compatible end-linkers, and allows from 1 to 6 (with sets of n=7 destination vectors and linkers as shown) transcription units (or nucleic acid fragments) to be assembled in one step. The orientation and position of type IIS restriction sites in destination vectors and end-linkers is such that assembled transcription units (or nucleic acid fragments) in level M constructs can be excised by a type IIs enzyme, in this case BsaI. Entry DNAs are flanked by type IIs restriction sites in opposite orientations (here BpiI sites). The cleavage sites of these two sites are each identical to one of the seven cleavage sites present on the left-hand side of level M destination vectors and linkers. The 7 cleavage sites on the left-hand side of the 7 destination vectors are unique (and different from one another). The same set of 7 cleavages sites is present on the left-hand side of the linkers M.

Figure 32B:
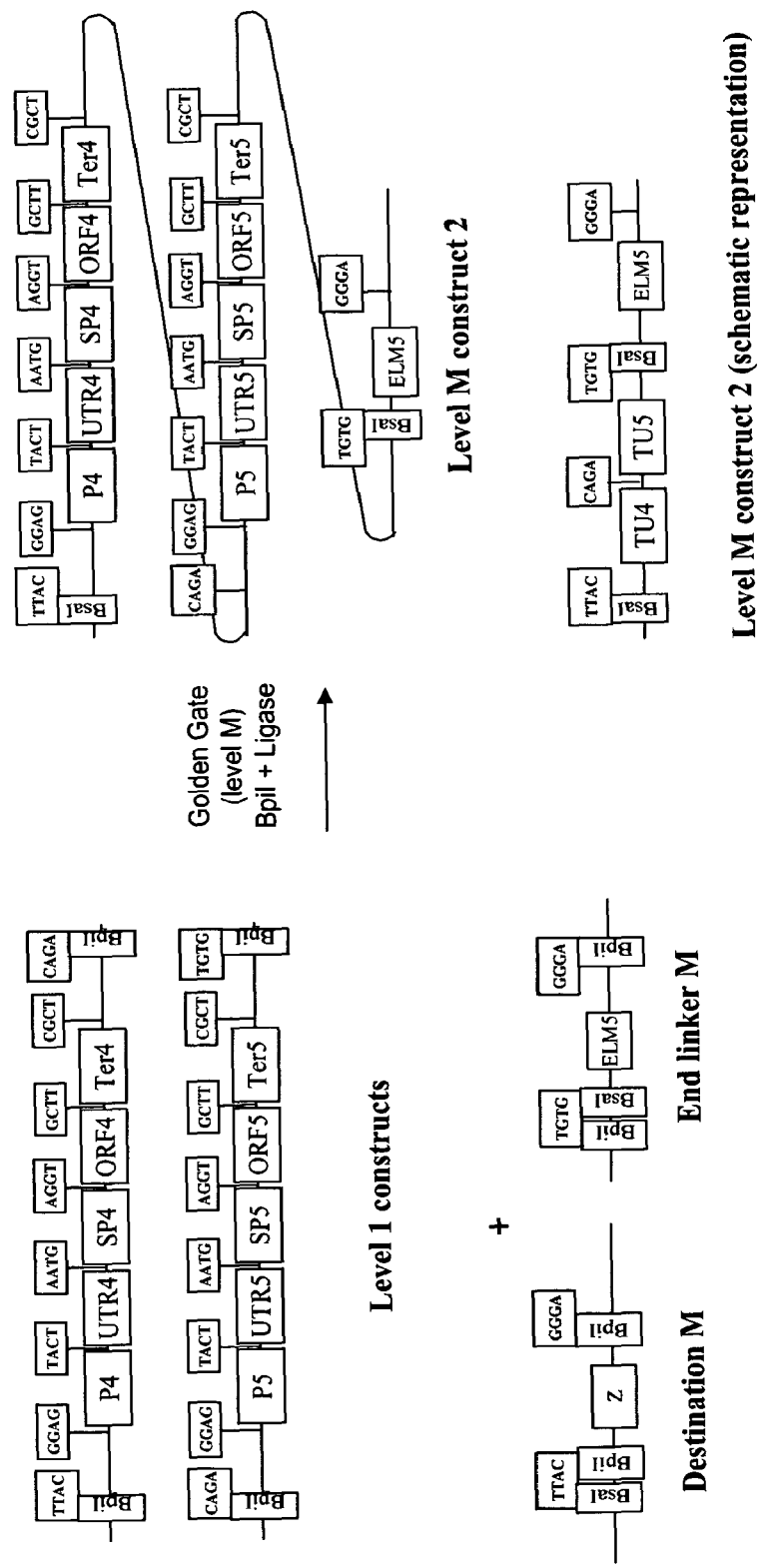
Figure 32C:
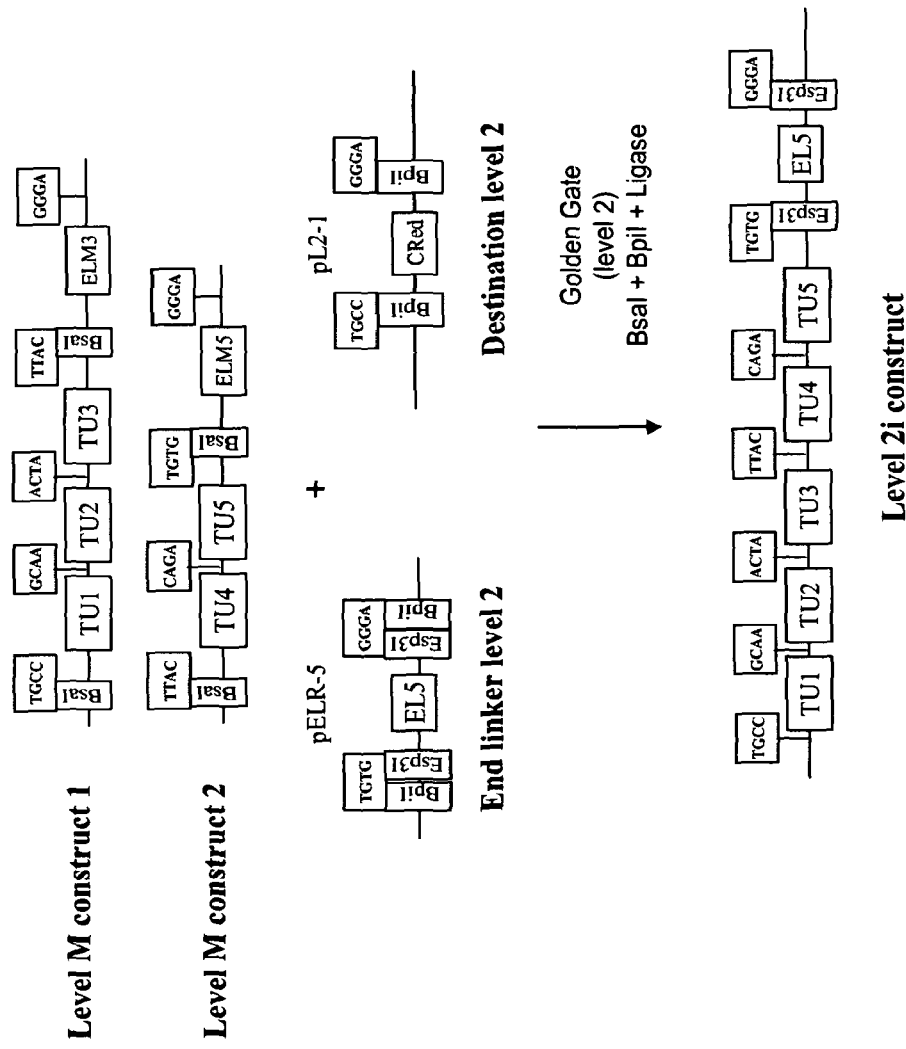

FIGS. 32A-C show an example where blocks of three (FIG. 32A) and two (FIG. 32B) transcription units are separately pre-assembled into level M destination vectors before being assembled in a level 2 vector in a subsequent step (FIG. 32C).

Figure 33:
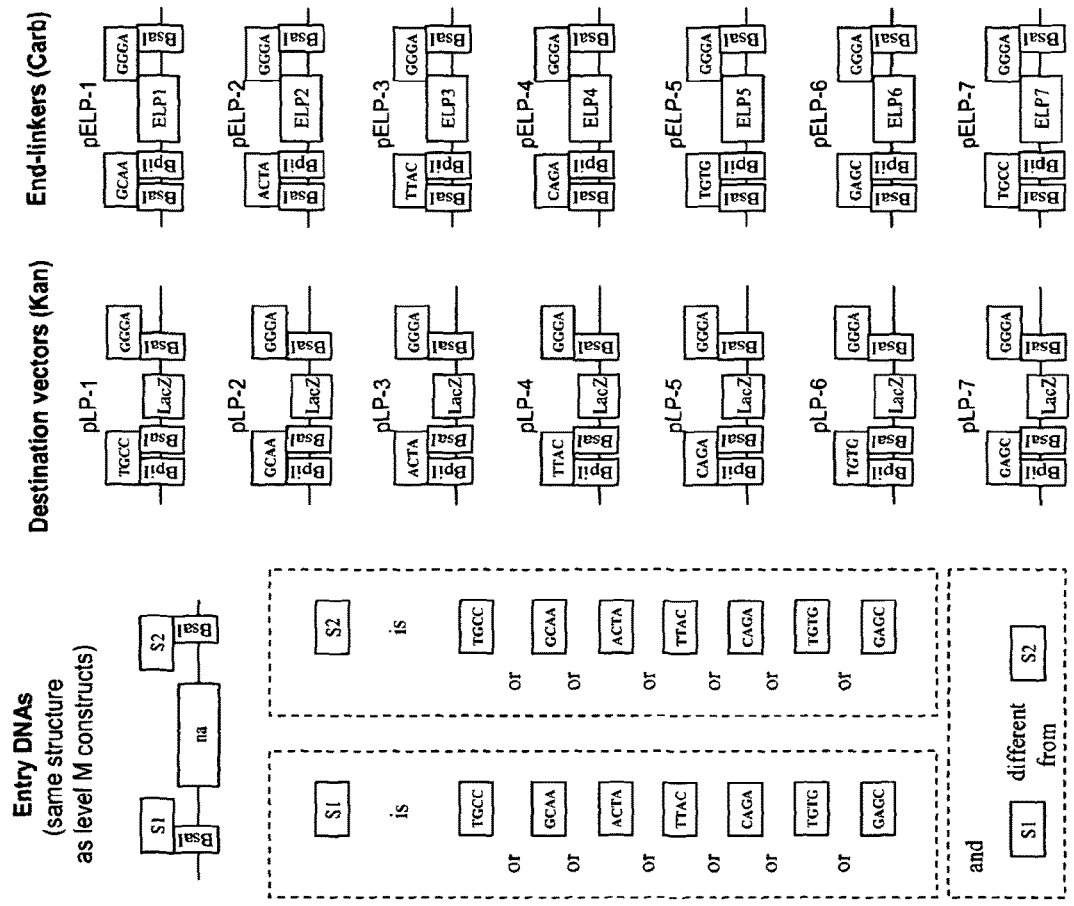
FIG. 33 illustrates a set of n=7 destination vectors and a set of n=7 end-linkers required for level M (left side of the figure) and P (right side of the figure). The destination vectors and end-linkers for level M (left side of the figure) are as shown in FIG. 31.

FIG. 33 illustrates a set of n=7 destination vectors and a set of n=7 end-linkers required for level M (left side of the figure) and P (right side of the figure). The destination vectors and end-linkers for level M (left side of the figure) are as shown in FIG. 31. The structure of entry DNAs for level P cloning is identical to the structure of entry DNAs for level M, except that restriction sites for a different type IIs enzymes are present (here for BsaI). Level M constructs have a structure corresponding to level P entry DNAs. Thus, level M constructs can be used as entry DNAs in a level P reaction. Level P constructs become entry DNAs for a next round of level M cloning.

FIG. 34A illustrates a level P reaction wherein two level M constructs are assembled into a level P destination vector using an end-linker P to give a level P construct.

FIG. 34B illustrates a level M reaction wherein two level P constructs are assembled into a destination vector M ("destination M") using an end-linker M to give a Level M construct.

Figure 35:
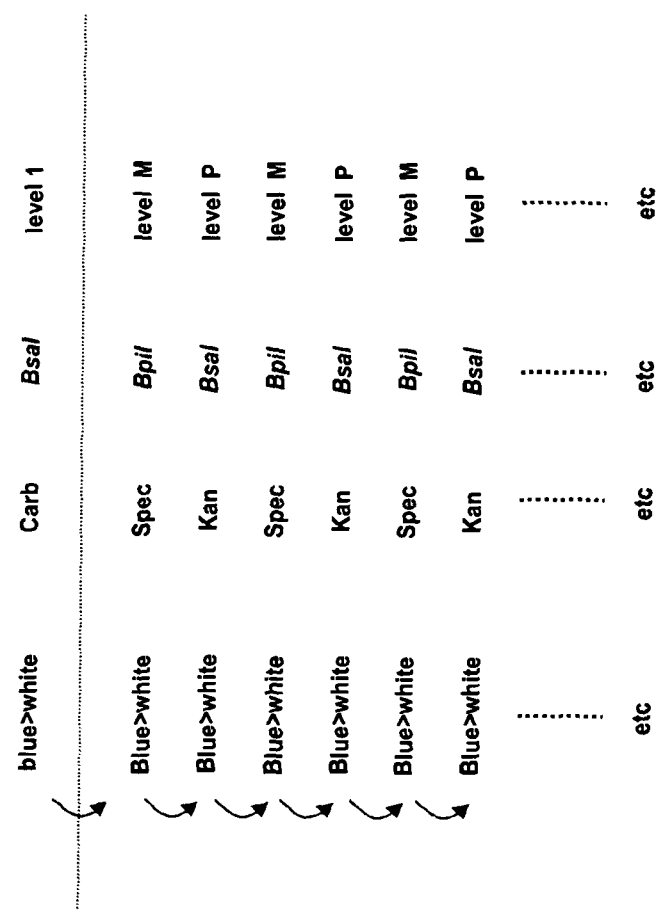
FIG. 35: Cloning from level P to level M and vice-versa can be repeated indefinitely by reusing the same set of vectors and end-linkers shown in FIG. 33.

FIG. 35: Cloning from level P to level M and vice-versa can be repeated indefinitely by reusing the same set of vectors and end-linkers shown in FIG. 33.

Figure 36:
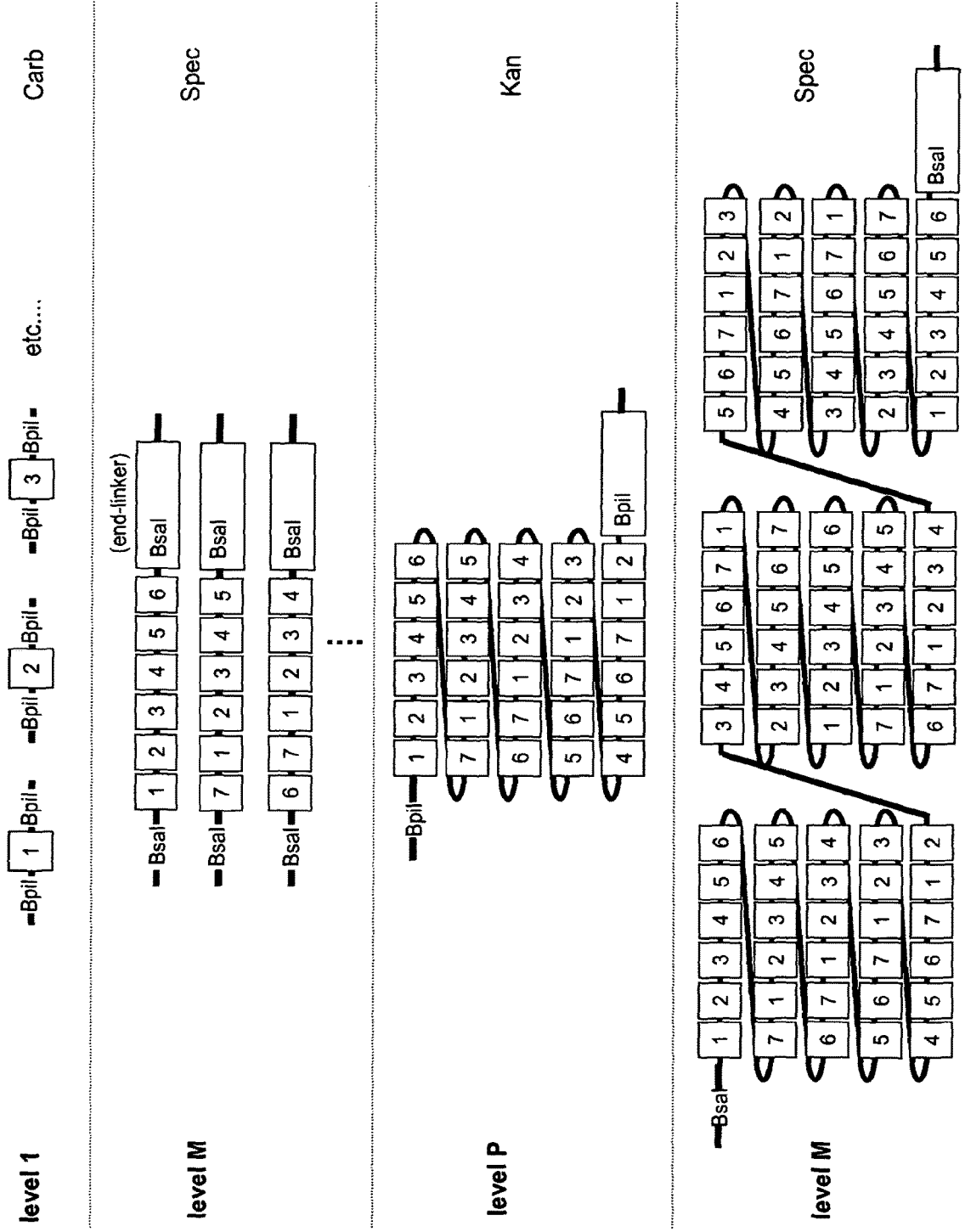
FIG. 36 illustrates the structure of constructs obtained in successive level M and level P cloning steps.

FIG. 36 illustrates the structure of constructs obtained in successive level M and level P cloning steps. In this example, 90 transcription units (or nucleic acid fragments) are assembled in a construct (shown at the bottom) in three cloning steps. 5 Sets of 6 transcription units are assembled in parallel in separate reactions in the first level M cloning step. The resulting 5 constructs are then assembled in one construct in the following cloning reaction on level P. This construct and two other compatible constructs (construction not shown for lack of space), each containing 30 assembled transcription units (or nucleic acid fragments) are then assembled in a third step of cloning in a level M destination vector. Boxes with numbers 1 to 7 represent nucleic acid fragments or transcription units, with such numbers referring only to the nature of the type IIs enzyme cleavage sites (position as defined earlier) flanking them, and not to the sequence of the nucleic acids contained between these two sites.

EXAMPLES

Molecular Biology Reagents

Restriction enzymes used in this study were purchased from New England Biolabs and Fermentas. T4 DNA ligase was purchased from Promega. Plasmid DNA preparations were made by using the NucleoSpin Plasmid Quick Pure kit (Macherey-Nagel, Duren, Germany) following the manufacturer protocol. Plasmid DNA concentration was measured using a Nano Drop® Spectrophotometer ND-1000 (Peqlab, Erlangen). The coding DNA for the coat proteins VP2, VP3, VP5 and VP7 of blue tongue virus serovar 8 was synthesised from Entelechon GmbH and lack all BpiI, BsaI and Esp3I restriction sites). Level-0 modules were sequenced with primers moclof (SEQ ID NO: 1: 5'-agcgaggaagcggaagagcg) and moclor (SEQ ID NO: 2: 5'-gccacctgacgtctaagaaacc).

Reference Example 1

Standard Cloning Protocol

A one step—one pot restriction/ligation was setup with approximately 30 fmol (~100 ng for a 5 kb plasmid) of each fragment (PCR product or plasmid), Promega ligation buffer, 10 U of the respective restriction enzyme (BsaI, BpiI, or Esp3I), 10 U high concentrated T4 DNA ligase (Promega), in a 20 μl volume. The reaction was incubated for 5 hours at 37° C., 5 min 50° C. and 5 min 80° C. The mix was added to 100 μl chemical competent DH10b cells, incubated for 30 min on ice and transformed by heat shock. Two clones with the expected color were analysed by restriction analysis and optionally by sequencing.

Reference Example 2

Cloning of the Canthaxanthin Biosynthesis Operon

A DNA fragment coding for canthaxanthin biosynthesis was made by PCR amplification of 4 genes from *Pantoea ananatis* that are necessary for biosynthesis of p3-carotene (genes crtE, crtY, crtI and crtB, Ref) and of one gene from *Agrobacterium aurantiacum* (crtW) necessary to convert β-carotene to canthaxanthin (ref). The gene crtW gene is used in addition to the 4 *Pantoea* genes because the orange/red color of canthaxanthin is easier to see on agar plates than the yellow color of β-carotene. The *Pantoea ananatis* strain was obtained from the DSMZ (cat DSM 30080), and a fragment containing the crtW gene was synthesised by Mr. Gene GmbH. An artificial operon containing the genes crtE-W-Y-1-B under control of the *P. ananatis* native promoter was made by ligation of three fragments derived from PCR: fragment 1 containing the promoter and crtE gene was amplified from *P. ananatis* genomic DNA with primers 5'-ttt ggtctc a ggag ggtaccgcacggtctgccaa (SEQ ID NO: 3) and 5'-ttt ggtctc a tcatgcagcatccttaactgacggcag (SEQ ID NO: 4), fragment 2 containing the crtW gene was amplified from a synthetic DNA fragment (sequence identical to the native sequence) with primers 5'-ttt ggtctc a atgagcgcacatgccctgcc (SEQ ID NO: 5) and 5'-ttt ggtctc a tcactcatgcggtgtccccttggt (SEQ ID NO: 6), and fragment 3 containing the genes crtY-1-B was amplified from *Pantoea* DNA using primers 5'-ttt ggtctc a gtgacttaagtgggagcggctatg (SEQ ID NO: 7) and 5'-ttt ggtctc a atgtagtcgctctttaacgatgag (SEQ ID NO: 8). The fragments were assembled by Golden Gate cloning in a target vector using BsaI. Two BpiI and one Esp3I site present in crtY were removed using primers containing silent mutations in the recognition sites.

Reference Example 3

Infiltration Tests

To check that the constructs are working, at least for one of the transcriptional units (containing GFP), all level-2 constructs were introduced into *Agrobacterium tumefaciens*. *Agrobacterium* suspensions were infiltrated with a syringe without a needle into *Nicotiana benthamiana* leaves. GFP is expressed from all constructs, as expected from expression cassettes driven by the 35S promoter. Interestingly, the level of GFP expression was found to decrease for the largest constructs. This can be explained by the fact that the GFP gene was always located at the left border in all constructs; since T-DNA transfer to plant cells occurs from the right to the left border, and is sometimes incomplete, plant cells will acquire the GFP cassettes from large constructs less frequently than from smaller constructs.

Example 1: Generation of the Basic Parts: The Level 0 Modules

We defined in a first step a generalized eukaryotic transcriptional unit as the basis for our modular cloning system (MoClo). This unit was subdivided into five basic modules which cover the most important features of any transcriptional unit: promoter (P), 5'UTR (5U), signal peptide (SP), open reading frame (ORF), and terminator (T, which also includes 3' untranslated sequences) (FIG. 3). For each module, two unique flanking recombination sites were defined. We use here the term 'recombination sites' by functional analogy to the recombination sites used in recombination systems such as the phage P1 Cre-loxP recombination system. However, for the purpose described here, 'recombination sites' can be any nucleotide sequence of choice of at least 3 base pairs in length, and will serve as the sequence where restriction enzyme digestion and ligation will take place; no recombinase will in fact be used. To guarantee efficient cloning, these sites were chosen to be non-palindromic and to share a maximum of two identical consecutive nucleotides. The recombination site between the promoter fragment and the signal peptide reads AATG and encodes a start codon preceded by an adenosine, which is the most common nucleotide in dicotyledonous plants at this position. The recombination site between the signal peptide and the rest of the protein (for secreted proteins) was chosen to be AGGT, with GGT coding for a glycine; this sequence was chosen as the last aminoacid of the signal peptide can usually be a glycine, and this allows producing secreted proteins with native sequence. The four remaining recombination site sequences chosen (GGAG, TACT, GCTT and CGCT) were selected without any special requirement other than being unique and non-palindromic, since they are all present in non-coding DNA.

The designated DNA fragments are then amplified by PCR with primers designed to attach the specific recombination site and the recognition site sequence for the type IIS restriction enzyme BpiI (FIGS. 5A and 5B). To allow efficient cloning of these PCR fragments, a set of level 0 destination vectors was constructed (one vector for each type of level 0 module), each containing two BpiI restriction sites compatible with the amplified PCR fragments. Beside the destination plasmids for the five standard elements (pL0-P, pL0-5, pL0-S, pL0-O and pL0-T) further variants were included, which allow an easy adaptation of the MoClo system to a wide variety of projects (FIG. 18). The expression of cytosolic proteins for example does not require a signal peptide, and these can be cloned into pL0-SO, spanning the SP and ORF position. All level 0 destination plasmids are based on a pUC19 backbone, confer spectinomycin resistance and encode a lacZa fragment for blue/white selection. On both sites of the lacZa fragment two different type IIS recognition sequences—for the enzymes BsaI and BpiI—are positioned in inverse orientation relative to each other (FIG. 5A, B). Both recognition sequences are designed to create the identical four nucleotide recombination site upon digestion (for example, sequence GGAG on the left side of the destination vector for cloning of promoter modules). This design allows cloning of the PCR product(s) for the DNA fragment of interest efficiently via BpiI—removing the BpiI recognition sites and lacZa in the process—but provides the possibility to release the cloned fragment with BsaI using the identical recombination sites it was cloned in.

The level 0 modules should not contain any of the type IIS restriction sites used in the MoClo system within the sequence of the fragments of interest. Beside the already mentioned BsaI and BpiI, a third type IIs enzyme, Esp3I, is used in the process of assembly of higher order constructs (see below). Removal of these sites can be easily done at the time of cloning of level 0 modules by using primers overlapping the internal BpiI, BsaI or Esp3I sites, but containing a single silent nucleotide mismatch in the recognition site. An example for the removal of a single BsaI site is given in FIG. 18C. The primers pr2 and pr3 introduce a guanine to cytosine exchange and destroy the BsaI recognition site. The level 0 module is then assembled from the PCR-fragments (n+1PCR fragments when n sites need to be removed) in a one-step one-tube reaction using BpiI into the appropriate level 0 destination plasmid. The purification of the PCR reaction prior cloning is preferable, as primer dimers can be competitors of the PCR product in the cloning procedure.

To show the versatility of the system, we cloned a number of modules for all elements of the transcriptional unit. These include 11 ORFs representing a wide spectrum of biological functions like immunoglobulins (IgG1 heavy and light chain), structural viral proteins from BTV and PVX (Potato Virus X), the silencing inhibitor p19, the bar resistance marker and GFP. As an example, we provide here how a promoter module can be cloned. The 35S promoter fragment was generated by PCR using 35S promoter specific primers which add the BpiI recognition sites (underlined) and the promoter module specific fusion sites (bold). The 35S forward primer comprises: 5'-ttt GAAGACAAGGAG (SEQ ID NO: 9:) followed by bases specific for the 35S promoter, 35S reverse comprises: 5'-ttt GAAGACAAAGTA (SEQ ID NO: 10:) followed by bases specific for the 35S promoter.

In order to create the level 0 module pICH41373 (pL0-P with the 35S promoter) by a BpiI dependent Golden gate cloning reaction, the following reaction mix was added into a single tube (FIG. 19A):

| | |
|---|---|
| 2 µl | 10× T4-ligase buffer (Promega) |
| 1 µl | high concentrated T4-ligase (Promega; 10 U/µl) |
| 1 µl | BpiI restriction enzyme (Fermentas 10 U/µl) |
| 1 µl | 30 fmol pL0-P destination plasmid |
| 1 µl | specific PCR product (column-purified to eliminate primer dimers) of the 35S promoter (generated by standard PCR with primers describe above) |
| 14 µl | water |
| 20 µl | total |

The reaction was incubated for 5 hours at 37° C., and 10 min 80° C. The mix was added to 100 µl chemical competent DH10b cells, incubated for 30 min on ice and transformed by heat shock. After plating on LB agar plates containing spectinomycin (100 µg/ml) and growing over night at 37° C., two white clones were analyzed by restriction analysis and by sequencing.

In contrast to the number of ORFs, the number of commonly used promoters and terminator sequences available for expression of heterologous proteins in plants is much lower. To avoid repetitive sequences in planned multigene constructs, we therefore cloned several *Arabidopsis thaliana* promoter and terminator sequences from genes which show a high basic expression level. After sequencing, the level 0 modules form the bottom level in the hierarchal MoClo system. A summary of all level 0 modules used in this study is presented in the table below:

| Module type and construct number | Relevant characteristics | Reference or accession number |
|---|---|---|
| | Promoter (P) | |
| pICH41373 | 35S promoter | CaMV[1] |
| pICH41551 | ST-LS1 (Stem and leaf specific) promoter | *S. tuberosum*;[2] |
| pICH42755 | 34S promoter | FMV[3] |
| pICH42760 | Spm promoter | *Zea mays*[4] |
| pICH44157 | RBCS (RuBisCO Small subunit 1b) promoter | *A. thaliana*; At5g38430; This work |
| pICH45131 | LHB1B2 promoter | *A. thaliana*; At2g34420; This work |
| pICH45145 | LHCB5 promoter | *A. thaliana*; At4g10340; This work |
| pICH45167 | RRM-containing protein promoter | *A. thaliana*; At1g70200; This work |
| pICH50581 | ACT2 (Actin 2) promoter | *A. thaliana*; At3g18780; This work |
| | 5'UTR (U) | |
| pICH46501 | Tabacco mosaic virus □□fragment | This work |
| | ORF | |
| pICH41531 | sGFP codon optimized | [5] |
| pICH42222 | Basta$^{TM}$ resistance protein (Phosphinothricin acetyltransferase) | *S. hygroscopicus*[6] |
| pICH44022 | P19 Tomato bushy stunt virus silencing inhibitor | [7] |
| pICH45502 | BTV (blue tongue virus) VP2 | This work |
| pICH45512 | BTV (blue tongue virus) VP3 | This work |
| pICH45526 | BTV (blue tongue virus) VP5 | This work |
| pICH45531 | BTV (blue tongue virus) VP7 | This work |
| pICH48348 | PVX CP | This work |
| pICH48367 | PVX 25K MP | This work |
| pICH49488 | $IgG_1$ Light chain with native signal peptide | This work |
| pICH49500 | $IgG_1$ Heavy chain with native signal peptide | This work |
| | Terminator (T) | |
| pICH41432 | Ocs terminator | *A. tumefaciens*[8] |
| pICH41414 | 35S terminator | CaMV |
| pICH44300 | ACT2 (Actin 2) terminator | *A. thaliana*; At3g18780; This work |
| pICH44311 | TGG1 (Thioglucoside Glucohydrolase 1) terminator | *A. thaliana*; At5g26000; This work |
| pICH44344 | GCRP (glycine-rich protein) terminator | *A. thaliana*; At1g67870; This work |
| pICH44355 | AAC1 (ADP/ATP carrier protein 1) terminator | *A. thaliana*; At3g08580; This work |
| pICH44377 | PRXR1 (Peroxidase 1) terminator | *A. thaliana*; At4g21960; This work |
| pICH44388 | AGP18 (Arabinogalactan protein 18) terminator | *A. thaliana*; At4g37450; This work |
| pICH44393 | GAE6 (UDP-D-Glucoronate 4-Epimerase 6) terminator | *A. thaliana*; At3g23820; This work |
| pICH49344 | Nos terminator | *A. tumefaciens*[9] |

[1] Guilley, H., Dudley, R. K., Jonard, G., Balazs, E. & Richards, K. E. Transcription of Cauliflower mosaic virus DNA: detection of promoter sequences, and characterization of transcripts. *Cell* 30, 763-773 (1982).
[2] Stockhaus, J., Eckes, P., Blau, A., Schell, J. & Willmitzer, L. Organ-specific and dosage- dependent expression of a leaf/stem specific gene from potato after tagging and transfer into potato and tobacco plants. *Nucleic Acids Res* 15, 3479-3491 (1987).
[3] Sanger, M., Daubert, S. & Goodman, R. M. Characteristics of a strong promoter from figwort mosaic virus: comparison with the analogous 35S promoter from cauliflower mosaic virus and the regulated mannopine synthase promoter. *Plant Mol Biol* 14, 433-443 (1990).
[4] Raina, R., Cook, D. & Fedoroff, N. Maize Spm transposable element has an enhancer-insensitive promoter. *Proc Natl Acad Sci USA* 90, 6355-6359 (1993).
[5] Chiu, W. et al. Engineered GFP as a vital reporter in plants. *Curr Biol* 6, 325-330 (1996).
[6] Thompson, C. J. et al. Characterization of the herbicide-resistance gene bar from Streptomyces hygroscopicus. *Embo J* 6, 2519-2523 (1987).
[7] Marillonnet, S., Thoeringer, C., Kandzia, R., Klimyuk, V. & Gleba, Y. Systemic Agrobacterium tumefaciens-mediated transfection of viral replicons for efficient transient expression in plants. *Nat Biotechnol* 23, 718-723 (2005).
[8] De Greve, H. et al. Nucleotide sequence and transcript map of the Agrobacterium tumefaciens Ti plasmid-encoded octopine synthase gene. *J Mol Appl Genet* 1, 499-511 (1982).
[9] Depicker, A., Stachel, S., Dhaese, P., Zambryski, P. & Goodman, H. M. Nopaline synthase: transcript mapping and DNA sequence. *J Mol Appl Genet* 1, 561-573 (1982).

Example 2: Assembly of Transcriptional Units: The Level 1 Constructs

The next level of cloning consists of assembling several level 0 modules into a complete transcriptional unit in a level 1 reaction. Since assembly is performed by Golden Gate cloning using the enzyme BsaI, no BsaI restriction site is left in the resulting level 1 construct. Therefore, to be able to later subclone the assembled transcriptional unit into higher level constructs, two restriction sites of a second type IIS restriction enzyme also have to be present flanking the assembled fragment. We therefore created level 1 destination vectors containing two BpiI restriction sites flanking the lacZa fragment, in addition to the two BsaI restriction sites needed for cloning of the transcription unit (pL1F-1 to pL1F-7, FIG. 4). If, as for level 0 destination vectors, the cleavage sites of the two different type IIS enzymes (BsaI and BpiI) overlapped, all level 1 transcriptional unit fragments would be flanked by the same GGAG and CGCT recombination sites (which originate from the promoter and terminator modules, respectively). The presence of identical overhangs flanking each transcriptional unit would prohibit the creation of higher level multigene constructs with a defined linear order. Consequently a series of seven level 1 destination vectors was designed in which the BpiI cleavage sites generate two recombination sites with new specificities for each vector (for example sites TGCC and GCAA for level 1 vector position 1, FIGS. 4 and 5B). These sites are compatible from one vector to the next so that assembled transcriptional units can be subcloned in a one-pot reaction from the level 1 constructs into a level 2 construct. If the sites of all level 1 constructs were defined strictly for linear assembly, the number of level 1 destination vectors would need to be as high as the number of transcriptional units that an experimenter would wish to assemble in a final construct. However, to avoid the construction and consideration of too many level 1 destination vectors, the spatial order of overhangs was designed to be circular instead of linear, as the first recombination site at position 1 (TGCC) is also the final site at position 7. So, a level 1 construct for position 1 can be reused later at a virtual position "8" (FIG. 4). Therefore, such a set of 7 level 1 destination vectors will allow an unlimited number (regarding the design, not the physical size of DNA) of transcriptional units to be cloned in a final nucleic acid construct of interest, although by incremental steps of up to 6 constructs at a time (see further description below for such assembly).

Between the upstream BpiI and BsaI sites, we also introduced additional restriction sites for analytical restriction digests: an EcoRI site is present in each level 1 destination plasmid, whereas a second restriction site is specific for each position (FIG. 5B). Beside the seven level 1 destination vectors for the assembly of transcriptional units in the forward direction, a set of level 1 destination vectors for cloning of transcription units in the opposite orientation was also created. Here the BsaI overhangs are in reverse complement orientation, but accept the same level 0 modules as for the other orientation (pL1R-1 to pL1-R7, FIG. 4).

Since our transient plant expression system is based on *Agrobacterium tumefaciens*, all plasmids have a broad host range RK2 origin of DNA-replication and left border (LB) and right border (RB) T-DNA sequences to allow T-DNA transfer into the plant cell. These two features allow testing the functionality of level 1 constructs by plant infiltration. It is also possible to make similar vectors for allowing expression in other eukaryotic hosts such as yeast, insect or mammalian cells or in prokaryotes. The level 1 destination vectors encode an ampicillin resistance gene and a lacZ fragment flanked by BpiI and BsaI sites.

To test the efficiency of the assembly of level 0 modules into level 1 transcriptional units (level 1 constructs), 11 artificial transcriptional units were designed (promoters and terminators were randomly assigned to ORFs without consideration for level of expression since all constructs in this study were made purely as an exercise to demonstrate the ability of the MoClo system for cloning of multigene constructs), and were (again randomly) assigned to one of the seven level 1 positions. In 11 independent cloning reactions, the level 0 modules were combined with the respective level 1 destination vectors, T4-DNA ligase and the restriction enzyme BsaI in a one-tube one-step reaction (FIG. 20). The different antibiotic resistances of level 0 and level 1 destination plasmids in combination with the blue/white selection represent a very convenient way to screen for correctly assembled level 1 constructs. After transformation, the reactions were spread on ampicillin and X-Gal containing plates and the numbers of white and blue clones were counted. The number of white, and therefore correct, colonies varied from approximately 16000 to 180000, whereas only a minor fraction (<1%) of blue colonies was present in two out of eleven reactions (FIG. 10). Two white colonies from each reaction were analyzed by an analytical restriction digest with BpiI (which cleaves on both sides of the assembled transcriptional unit). All 22 tested plasmids contained a fragment of the expected size.

We provide here as an example how the cloning reaction was set up for one of the transcription units. In order to create the level 1 construct pICH50711 by a BsaI dependent Golden gate cloning reaction, the following reaction mix was added into a single tube (FIG. 19B):

| | |
|---|---|
| 2 µl | 10× T4-ligase buffer (Promega) |
| 1 µl | high concentrated T4-ligase (Promega; 10 U/µl) |
| 1 µl | BsaI restriction enzyme (NEB; 10 U/µl) |
| 1 µl | 30 fmol pL1F-1 destination plasmid |
| 1 µl | 30 fmol pICH41373 (level 0 promoter module, 35S promoter) |
| 1 µl | 30 fmol pICH46501 (level 0 5'UTR module, TMV untraslated region) |
| 1 µl | 30 fmol pICH41531 (level 0 ORF module, GFP) |
| 1 µl | 30 fmol pICH41432 (level 0 terminator module, Ocs terminator) |
| 11 µl | water |
| 20 µl | total |

The reaction was incubated for 5 hours at 37° C., 5 min 50° C. and 5 min 80° C. The mix was added to 100 µl chemical competent DH10b cells, incubated for 30 min on ice and transformed by heat shock. After plating on LB agar plates containing ampicillin (100 pg/ml) and growing over night at 37° C., two white clones were analyzed by restriction analysis and optionally by sequencing.

Example 3: Design of Multigene Constructs: The Level 2

As all other MoClo constructs, multigene level 2 constructs are assembled from lower level (here level 1) constructs using a one-pot restriction-ligation. In this case, assembly is performed using the enzyme BpiI. Level 2 destination vectors carry a kanamycin resistance gene, in accordance with the principle that a specific selection marker is assigned to each level of cloning, allowing effective counter-selection against entry plasmid backbones. Level 2 destination vector backbones do not contain any type IIs restriction sites used in the MCIo system, other that the recognition sites used for the cloning of the inserts. In contrast to level 0 and level 1, the visible selectable marker used for level 2 constructs is not a lacZ gene, but an artificial bacterial operon containing 5 genes (see Reference Example 2) that lead to biosynthesis of canthaxanthin, a red (more precisely salmon/orange) colored carotenoid pigment. A lacZ gene for blue-white selection would have also worked for this step, but the choice of a new color selectable marker is explained below in the paragraph on level 2i. The cantaxanthin operon in level 2 destination vector pL2-1 is flanked by two BpiI sites that create TGCC and GGGA overhangs after digestion (FIG. 4). The TGCC overhang is compatible with the level 1 construct for position 1, while the GGGA represents an overhang which is unique to level 2 destination plasmids. Depending on the number of level 1 constructs that are subcloned in one step (from one to a maximum of 6 transcription units), the last overhang of the assembled DNA fragment will be different for each of the six possibilities. To connect this end with the GGGA overhang of the level 2 destination vector, a set of seven end-linkers (pELE-n) was designed (FIG. 4, the seventh linker is necessary only when using the other level 2 destination vectors described below). Like the level 1 modules, the end-linker plasmids confer ampicillin resistance, and are themselves flanked by BpiI sites. These two features make them compatible with standard level 1 destination vectors (and constructs obtained therefrom) in a BpiI-based level 2 Golden Gate cloning reaction. End-linkers can consist of any DNA sequence, and serve the purpose of joining two chosen type IIs enzyme cleavage sites. For example, the sequence of linker pELE-1 is (SEQ ID NO: 11) gaagac aa GCAA gaggatgcacatgtgaccga GGGA tt gtcttc (bold is the Bpi recognition sites, underlined are the cleavage sites, and in between is the joining linker sequence). The end linkers are cloned in a pUC19 based plasmid (but could also be cloned in other backbones).

At first glance the level 1 constructs designed for a defined position cannot be reused in a different context. For example, a level 1 construct made for subcloning at position three cannot be used without two other constructs for position 1 and 2. Placing the same transcriptional unit at position 1 could be done by recloning the same level 0 modules in a level 1 destination vector specific for position 1. However, a possibility to reduce the need for extensive recloning of the same construct for different positions is given by the periodical design of the level 1 overhangs. Here the relative position of, for example a level 1 position 3 construct, can easily be shifted to the relative first position, when the left overhang from the level 2 destination vector would read ACTA instead of TGCC. Here the first two positions would be virtually deleted, shifting position 3 to a relative position 1. A set of seven level 2 destination vectors created for this purpose is shown in FIG. 4 (pL2-1 to pL2-7). Together with the seven end-linker plasmids, these 14 plasmids allow to realize every overhang combination in a level 2 destination vector. The identical flexibility only based on level 2 destination vectors without the end-linkers would require 36 different plasmids.

To test cloning of several level 1 transcriptional units into level 2 constructs, 5 different restriction-ligation reactions were set up to clone from 2 up to 6 transcriptional units in a single step. The restriction-ligation reactions each contains from 2 to 6 level 1 transcriptional unit constructs (pICH50711, pICH50721, pICH49722, pICH49733, pICH50731, pICH50741 FIG. 10), one appropriate end-linker (pELE-2 to pELE-6), and the destination vector pL2-1.

The reaction was incubated for 5 hours at 37° C. and 10 min 80° C. The mix was added to 100 µl chemical competent DH10b cells, incubated for 30 min on ice and transformed by heat shock. The transformation was plated on LB agar plates containing kanamycin (100 µg/ml) and the plate incubated over night at 37° C.

Considering all level 1 cloning experiments, the number of white colonies obtained per transformation, which gives a measure of the cloning efficiency, decreased from approximately 33000 (for two level 1 modules plus end linker) to 150 (six modules plus end-linker), and the percentage of red colonies raised from 0.02% to 10% (FIG. 10). Six white colonies were tested from each level 2 assembly by an analytical endonuclease restriction digest and all were found to be correct.

Example 4: The Level 2i-1

As we have shown above, the assembly of up to six transcription units to produce a 24 kb construct (pICH51201) can be done in a one-step and one-tube level 2 reaction. However the final level 2 constructs are in a "closed" status and no additional genes can be inserted since no type IIS restriction sites are left in the construct. An entry option can be provided when modified end-linkers containing additional type IIS restriction sites (pELB-n) are used in the assembly of the level 2 constructs (FIG. 4). This type of construct was named level 2i since it is based on level 2 backbones but represents also an intermediate step to extend the number of genes in the construct beyond six. This intermediate construct can be used both as a destination vector for a final construct (level 2-2) or once again to construct the next level destination vector (level 2i-2), in case more than 6 more genes still need to be added to the construct. Given these alternative possibilities, the same visual selectable marker (such as LacZa for blue/white selection) cannot be used for all possible cloning steps. It is for this reason that we developed a second color selectable marker, that we developed based on carotenoid biosynthetic genes. With such marker, every cloning step can be performed using color selection, for example from red to white for level 2, red to blue for level 2i, blue to white for level 2-2, blue to red for level 2i-2, etc. . . . . .

As an example of end-linker sequence, we provide the sequence features of plasmid pELB-1. pELB-1 contains the sequence (SEQ ID NO: 12) gaagac aa tgcc t gagacc (bold BpiI recognition site, underlined cleavage site of BpiI and BsaI, italics BsaI recognition site) followed by a puc19 fragment containing the LacZ alpha fragment (gcagctggcacgacaggtttcccgactggaaagcgggcagt-gagcgcaacgcaattaatgtgagttagctcactcattaggcaccc caggcttta-cactttatgcttccggctcgtatgttgtgtggaattgtgagcggataacaattt-cacacaggaaacagctatgaccatgatta cgccaagcttgcatgcctgcaggtcgactctagag-gatccccgggtaccgagctcgaattcactggccgtcgttttacaacgtcgtgac tgggaaaaccctggcgttacccaacttaatcgccttgcagca-catcccccttttcgccagctggcgtaatagcgaagaggcccgcacc gatcgcccttcccaacagttgcgcagcctgaatggcgaatggcgcctgatgcggt-attttctccttacgcatctgtgcggtatttcacacc gcatatggtgcactctcagta-caatctgctctgatgccgcatagttaagccagccccgacacccgc-caacacccgctgacgcgccct gacgggcttgtctgctcccggcatccgcttacagacaagctgtgac (SEQ ID NO: 13), followed by sequence ggtctc a ggga tt gtcttca (SEQ ID NO: 14) (as before, bold BpiI recognition site, underlined cleavage site of BpiI and BsaI, italics BsaI recognition site). The sequence of the end-linker shown above is cloned in a pUC19-based vector (that does not contain additional LacZ fragment sequences), but can also be cloned in other plasmid backbones).

To test cloning of level 2i constructs, two restriction-ligations were set up as for level 2, except that the end-linker was replaced by an end-linker containing BsaI sites and a lacZ gene (constructs pICH51212 and pICH51226, FIG. 10). We provide here in more detail the set up for cloning of pICH51212 as an example. In order to create the level 2i construct pICH51212 by a BpiI dependent Golden gate cloning reaction, the following reaction mix was added into a single tube (FIG. 19 C):

| 2 µl | 10× T4-ligase buffer (Promega) |
|---|---|
| 1 µl | high concentrated T4-ligase (Promega; 10 U/µl) |
| 1 µl | BpiI restriction enzyme (Fermentas 10 U/µl) |
| 1 µl | 30 fmol pL2-1 (destination vector) |
| 1 µl | 30 fmol pICH50711 (level 1 construct for position 1, transcription unit with GFP) |
| 1 µl | 30 fmol pICH50721 (level 1 construct for position 2, transcription unit with p19) |
| 1 µl | 30 fmol pICH49722 (level 1 construct for position 3, transcription unit with VP2) |
| 1 µl | 30 fmol pICH49733 (level 1 construct for position 4, transcription unit with VP5) |
| 1 µl | 30 fmol pICH50731 (level 1 construct for position 5, transcription unit with VP7) |
| 1 µl | 30 fmol pELB-5 (end-linker for position 6) |
| 9 µl | water |
| 20 µl | total |

In contrast to previous constructs, red/blue selection is performed rather than red/white selection. In addition to red and blue colonies, a few colonies had a dark green color. These contain incorrect plasmids that have both the canthaxanthin operon and a lacZ gene. The number of colonies containing correctly assembled plasmids (blue colonies), and the ratio of red to blue colonies for pICH51212 and pICH51226 were comparable with the level 2 construct made from a similar number of entry clones, pICH51191 and pICH51201.

Example 5: The Level 2-2

As a starting point for the introduction of up to six further level 1 constructs, the level 2i-1 construct pICH51212 was chosen as a destination vector. This construct contains, beside five level 1 modules, a lacZa end-linker providing two BsaI restriction sites. In contrast to the previously described cloning of level 1, level 2 or level 2i constructs, which required either BsaI (level 1) or BpiI (level 2 and level 2i) alone, we have to use here both enzymes at the same time. BsaI allows reopening the level 2i backbone and provides defined overhangs which are compatible with the level 1 modules released by BpiI. Since two type IIS restriction enzymes have to be used at the same time and the target plasmid has already a size of 22 kb, we again tested the efficiency of the Golden Gate cloning for the introduction of either one to up to six level 1 modules simultaneously.

The results for the construction of plasmids pICH51761 to pICH51811 show that the cloning efficiency decreases dependent on the number of incorporated transcription unit fragment constructs (FIG. 10). Interestingly, the rate with which the cloning efficiency drops is similar to the earlier analyzed set of level 2-1 plasmids (pICH51161 to pICH51201) despite the different target plasmid size of 22 kb versus 4 kb. Since no positive clone was obtained for the largest construct, we repeated the cloning using different reaction conditions (FIG. 10, for pICH1811*).
The following reaction mix was set up (FIG. 19D):

| 2 µl | 10× T4-ligase buffer (Promega) |
|---|---|
| 1 µl | high concentrated T4-ligase (Promega; 10 U/µl) |
| 0.5 µl | BpiI restriction enzyme (Fermentas 10 U/µl) |
| 0.5 µl | BsaI restriction enzyme (NEB 10 U/µl) |
| 4.67 µl | 40 fmol pICH51212 level 2i-1 construct |
| 0.72 µl | 40 fmol pICH50741 (level 1 construct for position 1) |
| 0.75 µl | 40 fmol pICH50751 (level 1 construct for position 2) |
| 0.69 µl | 40 fmol pICH50761 (level 1 construct for position 3) |
| 0.75 µl | 40 fmol pICH50771 (level 1 construct for position 4) |
| 0.58 µl | 40 fmol pICH50781 (level 1 construct for position 5) |
| 1.17 µl | 40 fmol pICH50791 (level 1 construct for position 6) |
| 0.70 µl | 40 fmol pELE-4 (end linker) |
| 5.97 µl | water |
| 20 µl | total |

The mix was incubated in a thermocycler with the following parameters: incubation for 2 minutes at 37° C., 5 minutes at 16° C., both steps repeated 45 times, followed by incubation for 5 minutes at 80° C. and 10 minutes are 80° C. The reaction mix was transformed in E. coli chemically competent cells, and an aliquot of the transformation plated on a LB plate containing Kanamycing and X-gal. These parameters greatly increased cloning efficiency since 2685 white colonies were obtained (for the whole transformation) and no blue colony (FIG. 10). Plasmid DNA from 6 randomly picked colonies was analyzed. All were found to contain the expected correct construct.

We have therefore shown here that complex constructs containing many transcription units (eleven as shown here, consisting of 44 individual basic modules) can easily be assembled by a series of three easy-to-perform one-pot reactions, and with extremely high cloning efficiency. The largest construct made in this study (pICH51811) has a size of 34 kb. Considering the relative efficiency with which this construct and its precursors were obtained, it is likely that we have not yet reached the upper size limit for constructs that can be made using this technology. To make larger constructs starting from those that we have described here, the next step would be to remake the final construct (pICH51811), but using an end-linker that would add two restriction sites for the enzyme Esp3I (end-linker pELR-4, FIG. 4), and use the resulting plasmid as a destination vector to add one or several additional genes.

Example 6: Infiltration Tests

To check the constructs, at least for one of the transcriptional units (containing GFP), all level 2 constructs were introduced into Agrobacterium tumefaciens. Agrobacterium suspensions were infiltrated with a syringe without a needle into Nicotiana benthamiana leaves. GFP is expressed from all constructs (FIG. 21), as expected from expression cassettes driven by the 35S promoter. Interestingly, the level of GFP expression was found to decrease for the largest constructs. This can be explained by the fact that the GFP gene was always located at the left border in all constructs; since T-DNA transfer to plant cells occurs from the right to the left border, and is sometimes incomplete, plant cells will acquire the GFP cassettes from large constructs less frequently than from smaller constructs.

Example 7: Cloning of Bacterial Operons

Level 0 Modules:
As an example for cloning of bacterial operons, we chose to work with a carotenoid biosynthesis pathway since carotenoids are easily visible in the colonies, for example as a red color for lycopene. We chose the Pantoea ananatis Zeaxanthin biosynthesis pathway, since all genes of the pathway are known and sequenced (Misawa et al., Journal of Bacteriology, 1990, 172:6704-6712). Three genes of this pathway are required for lycopene biosynthesis crtE, crtI and crtB. We PCR-amplified all three genes and cloned them in vector pL0-SO (FIG. 18) as described for eukaryotic coding sequences. The resulting level 0 constructs are shown in FIG. 22. We also cloned several genes known to increase synthesis of lycopene when over-expressed in *E. coli* cells expressing the three crt genes necessary for lycopene production. These genes are dxs, ispA, idi and AppY. The genes for dxs and ispA were amplified and cloned from both *E. coli* strain K12 and from *Agrobacterium rhizogenes* strain K84. The genes for idi and AppY were cloned only from *E. coli* strain K12. In addition, the LacZ promoter present in pUC19 and the *Pantoea ananatis* promoter from the Zeaxanthin biosynthesis operon were also cloned as level 0 modules (FIG. 22).

Level 1 Destination Vectors for Cloning of Coding Sequences:

Level 1 destination vectors for cloning of bacterial coding sequences are different from destination vectors for cloning eukaryotic transcription units, since they are designed for cloning of individual coding sequences rather than complete transcription units. Moreover, they also provide a bacterial ribosome binding site (RBS) to the cloned coding sequence. Instead of making vectors with a defined RBS sequence, we made vectors with a degenerate RBS to provide a range of expression levels (FIG. 23A). For example, vector pICH4862L was made by PCR amplification of the LacZ fragment from pUC19 using primers prok1-1deg (SEQ ID NO: 15) (tttcgtctcattcagaagacat TGCC nv agga dnnnnnn AATG ggagaccttatgaccatgattacgccaagc, in bold is the core sequence of the RBS and flanking it is degenerate sequence, the underlined sequence is the cleavage sites of the BpiI or BsaI restriction sites) and prok1-2 (SEQ ID NO: 16) (tttcgtctcacttagaagacaa TTGC AAGC tgagaccttatgcggcatcagagcagattgt). In the above sequence, v stands for a, c or g; d stands for a, t or g; and n stands for a, t, g or c. This PCR product was cloned using DraIII in a pUC19-based plasmid backbone containing compatible DraIII sites. Single colonies were not picked since the result of this cloning is a library. Instead, the entire library was grown in *E. coli* and plasmid DNA prepared from the library. A similar procedure was repeated for the other 6 destination vectors, but using different primers for the different type IIs cleavage sites.

End Linkers:

Since for this experiment we are cloning carotenoid genes, end-linkers and level 2 destination vectors were made that do not already contain carotenoid genes. End linkers in particular were made in which the sequence of the linker consists of the Lac Z terminator sequences from plasmid pUC19. The two sets of end linkers are shown in FIG. 23B.

Level 1 Constructs:

A set of level 1 constructs was constructed from level 0 modules. Promoter modules were cloned in vector pL1F-1 (FIG. 12) and the coding sequences in vectors pICH5025L to pICH2030L for the different positions expected in the final construct (FIG. 24). Cloning was performed as a one-tube cloning reaction using the selected level 0 module and the chosen destination vector (or vector library) using the enzyme BsaI as described for cloning of level 1 eukaryotic transcription units. The 6 genes cloned as level 0 modules and known to increase lycopene production in *E. coli* were all cloned for positions 5, 6 and 7.

Level 2i-1 Constructs:

Two constructs were made containing the lycopene biosynthesis genes crtB, crtE and crtI and either the lac Z promoter or the *Pantoea ananatis* promoter. No terminator cloned as level 1 module was used since the terminator is provided here by the end-linker (FIG. 25). The resulting constructs, pICH5848L and pICH5850L are in fact two different libraries, in which all constructs have different RBS sequences for each of the three genes. The colonies displayed a wide variation in the amount of red color, as expected from such libraries. The libraries were grown and plasmid DNA prepared from them.

Level 2i-2 Constructs:

The next step consists of adding two or three genes to the previous constructs to try to increase the amount of lycopene produced. Since we have 6 genes available cloned at three different positions, there are too many possible combinations to test them all individually. Instead, libraries can be made in which any of the 6 genes will be cloned randomly at any of the two or three positions (position 5 and 6, or 5, 6 and 7, FIGS. 26 A and B). Four different libraries were made by setting up 4 reactions by adding into one tube all the constructs depicted in FIG. 26A (two reactions with either the LacZ promoter or the *Pantoea* promoter) or 26B (two reactions as well) and incubating the mixes in presence of BsaI and BpiI enzymes and ligase (as described previously for level 2i-2 for eukaryotic constructs). Colonies with a wide range of intensity for the red color were obtained (FIG. 26B), with many colonies having a stronger red that the parental 2i-1 constructs. To test that genes (from the 6 selected genes) had been cloned randomly at the three positions, 8 constructs from intense red colonies were sequenced. All constructs contained a different combination of genes. All sequenced constructs contained a dxs gene at least at one of the three positions; this is not surprising, since dxs is known to be the gene with the strongest effect on lycopene production among all enhancer genes tested as reported in the literature.

The invention claimed is:

1. System for producing a nucleic acid construct of interest, said system comprising:
a set of n entry DNAs numbered 1 to n, n being an integer of at least 3,
each of said n entry DNAs comprising in this order:
(i) a type IIs restriction endonuclease recognition site followed by the cleavage site thereof;
(ii) a sequence portion linking the cleavage site of said recognition site of item (i) with the cleavage site of the recognition site of the following item (iii), and
(iii) a cleavage site of a further type IIs restriction endonuclease recognition site followed by the recognition site of said cleavage site;
the cleavage sites of the type IIs restriction endonuclease recognition site(s) of item (iii) of entry DNA(s) 1 to n−1 is/are complementary to the cleavage site(s) of the type IIs restriction endonuclease recognition site(s) of item (i) of entry DNA(s) 2 to n, respectively;
the cleavage site of the type IIs restriction endonuclease recognition site of item (iii) of entry DNA n is complementary to the cleavage site of the type IIs restriction endonuclease recognition site of item (i) of entry DNA 1;
said system further comprising a destination vector comprising in this order:
(I) a type IIs restriction endonuclease recognition site followed by the cleavage site thereof;
(II) a vector backbone comprising a selectable marker gene, said vector backbone linking the cleavage sites of said recognition sites of items (I) and the following item (III);
(III) a further cleavage site of a type IIs restriction endonuclease recognition site followed by the recognition site of said cleavage site, and
(IV) optionally, an insert between the recognition sites of item (III) and item (I);
said system further comprising a nucleic acid linker comprising in the following order:
(a) a type IIs restriction endonuclease recognition site;
(b) a cleavage site of said recognition site of item (a);
(c) a cleavage site of a further type IIs restriction endonuclease recognition site of the following item (d);
(d) a type IIs restriction endonuclease recognition site defining the cleavage site of item (c) and being a recognition site of a type IIs restriction endonuclease different from that of item (a);
(e) a type IIs restriction endonuclease recognition site;
(f) a cleavage site of said recognition site of item (e);
(g) a cleavage site of a further type IIs restriction endonuclease recognition site of the following item (h);
(h) a type IIs restriction endonuclease recognition site defining the cleavage site of item (g);
said linker being capable of linking a cleavage site of item (iii) of one of a entry DNA numbered 1 to n to a cleavage site of item (III) of said destination vector.

2. The system according to claim 1, wherein a type IIs restriction endonuclease recognising the recognition site (I) of said destination vector can produce a single-stranded overhang from the cleavage site of item (I) that is complementary to the single-stranded overhang producible by the type IIs restriction endonuclease recognising the recognition site (i) of entry DNA numbered 1 for enabling annealing of said complementary single-stranded overhangs and ligation of said destination vector with the DNA segment of item (ii) from entry DNA numbered 1.

3. The system according to claim 1, wherein the cleavage site of item (iii) of one of said entry DNAs is complementary to the cleavage site of item (b) of said linker, and
the cleavage site of item (g) of said linker is complementary to the cleavage site of item (III) of said destination vector.

4. The system according to claim 1, comprising from 1 to n multiple destination vectors numbered 1 to n, each of said 1 to n destination vectors having segments (I) to (III) as defined in claim 1 and optionally a segment (IV) as defined in claim 1,
wherein the cleavage sites of item (III) of all n destination vectors are identical and all cleavage sites of item (I) of all n destination vectors are unique among the cleavage sites of item (I).

5. The system according to claim 1, comprising a set of n nucleic acid linkers numbered 1 to n, each n-th linker comprising items (a) to (h) as defined in claim 1,
the cleavage site of item (iii) of each n-th entry DNA is complementary to the cleavage site of item (b) of the n-th linker;
the cleavage site of item (g) of each n-th linker being complementary to the cleavage site of item (III) of the n-th destination vector;
whereby each n-th linker being capable of linking a cleavage site of item (iii) of the n-th entry DNA to a cleavage site of item (III) of each n-th destination vector.

6. The system according to claim 1, wherein each sequence portion of item (ii) of each entry DNA 1 to n comprises a further pair of two type IIs restriction endonuclease recognition sites oriented such that said further pair of recognition sites can be removed from said entry DNAs by treatment with type IIs restriction endonuclease(s) recognising said further pair of recognition sites, said further pair of recognition sites may flank a marker gene for enabling selection of cell clones for the presence or absence of said marker gene;
wherein said further pair of two type IIs restriction endonuclease recognition sites are recognition sites of endonucleases different from the recognition sites of item (i) and item (iii) of claim 1.

7. The system according to claim 1, wherein the cleavage sites of the recognition sites of item (i) are unique among the item (i) recognition sites of the set of n entry DNAs, and the cleavage sites of the recognition sites of item (iii) are unique among the item (iii) recognition sites within the set of n entry DNAs.

8. The system according to claim 1, wherein the type IIs restriction endonuclease recognition sites of items (i) and (iii) are recognition sites of the same type IIs restriction endonuclease.

9. The system according to claim 1, wherein the cleavage sites of the recognition sites of item (III) of all destination vectors are identical, and the cleavage sites of the recognition sites of item (I) of all destination vectors are non-identical.

10. System for producing a nucleic acid construct of interest, said system comprising:
a set of n entry DNAs numbered 1 to n, n being an integer of at least 3,
each of said n entry DNAs comprising in this order:
(i) a type IIs restriction endonuclease recognition site followed by the cleavage site thereof;
(ii) a sequence portion linking the cleavage site of said recognition site of item (i) with the cleavage site of the recognition site of the following item (iii), and (iii) a cleavage site of a further type IIs restriction endonuclease recognition site followed by the recognition site of said cleavage site;

the cleavage sites of the type IIs restriction endonuclease recognition sites of item (iii) of entry DNAs 1 to n−1 are complementary to the cleavage sites of the type IIs restriction endonuclease recognition sites of item (i) of entry DNAs 2 to n, respectively;

all cleavages sites of item (i) are unique among said n entry DNAs, and all cleavage sites of item (iii) are unique among said n entry DNAs;

said system further comprising a destination vector comprising in this order:

(I) a type IIs restriction endonuclease recognition site followed by the cleavage site thereof;

(II) a vector backbone comprising a selectable marker gene, said vector backbone linking the cleavage sites of said recognition sites of items (I) and the following item (III);

(III) a further cleavage site of a type IIs restriction endonuclease recognition site followed by the recognition site of said cleavage site, and (IV) optionally, a linker between the recognition sites of item (III) and item (I);

said system further comprising a nucleic acid linker comprising in the following order:

(a) a type IIs restriction endonuclease recognition site;

(b) a cleavage site of said recognition site of item (a);

(c) a cleavage site of a further type IIs restriction endonuclease recognition site of the following item (d);

(d) a type IIs restriction endonuclease recognition site defining the cleavage site of item (c) and being a recognition site of a type IIs restriction endonuclease different from that of item (a);

(e) a type IIs restriction endonuclease recognition site;

(f) a cleavage site of said recognition site of item (e);

(g) a cleavage site of a further type IIs restriction endonuclease recognition site of the following item (h);

(h) a type IIs restriction endonuclease recognition site defining the cleavage site of item (g);

said linker being capable of linking a cleavage site of item (iii) of one of a entry DNA numbered 1 to n to a cleavage site of item (III) of said destination vector.

11. The system according to claim 10, comprising the same number n of said linkers as the system comprises entry DNAs, said linkers being numbered 1 to n, wherein all linkers have the same cleavage site (g) that is complementary to the cleavage site of item (III) of said destination vector for linking each linker to the recognition site of item (III) of said destination vector, and wherein each of said n linkers has a different cleavage site (b) that is complementary to the cleavage site of item (iii) of one of said n entry DNAs.

12. The system according to claim 11, said system further comprising n different destination vectors, each destination vector being defined by items (I) to (IV) and having the same cleavage site of item (III) that is complementary to the cleavage site (g) of all linkers, each of said destination vectors having a different cleavage site if item (I) that is complementary to the cleavage site of item (i) of one of said n entry DNAs.

* * * * *